(12) United States Patent
Labrie et al.

(10) Patent No.: US 7,709,516 B2
(45) Date of Patent: May 4, 2010

(54) HELIX 12 DIRECTED NON-STEROIDAL ANTIANDROGENS

(75) Inventors: Fernand Labrie, Québec (CA); Rock Breton, Québec (CA); Shankar Mohan Singh, Québec (CA); René Maltais, Québec (CA)

(73) Assignee: Endorecherche, Inc. (CA)

( * ) Notice: Subject to any disclaimer, the term of this patent is extended or adjusted under 35 U.S.C. 154(b) by 186 days.

(21) Appl. No.: 11/452,545

(22) Filed: Jun. 14, 2006

(65) Prior Publication Data

US 2006/0287327 A1 Dec. 21, 2006

Related U.S. Application Data

(60) Provisional application No. 60/691,391, filed on Jun. 17, 2005.

(51) Int. Cl.
*A61K 31/45* (2006.01)
*A61K 31/4166* (2006.01)

(52) U.S. Cl. .................................. 514/389; 514/425

(58) Field of Classification Search .............. 514/237.2, 514/316, 389, 425
See application file for complete search history.

(56) References Cited

U.S. PATENT DOCUMENTS

| | | | |
|---|---|---|---|
| 5,411,981 A | 5/1995 | Gaillard-Kelly et al. | 514/386 |
| 5,556,983 A | 9/1996 | Claussner et al. | 548/300.7 |
| 6,071,957 A | 6/2000 | Miller et al. | 514/522 |
| 2004/0077605 A1 | 4/2004 | Salvati et al. | 514/81 |
| 2004/0077606 A1 | 4/2004 | Salvati et al. | 514/81 |
| 2005/0153968 A1 | 7/2005 | Bi et al. | 514/248 |
| 2005/0159468 A1 | 7/2005 | Cleve et al. | 514/389 |
| 2005/0187261 A1 | 8/2005 | Verner et al. | 514/350 |
| 2005/0250741 A1 | 11/2005 | Lanter et al. | 514/63 |
| 2006/0009529 A1 | 1/2006 | Dalton et al. | 514/620 |
| 2006/0014739 A1 | 1/2006 | Schlienger et al. | 514/231.2 |
| 2006/0063819 A1 | 3/2006 | Lanter et al. | 514/389 |

FOREIGN PATENT DOCUMENTS

| | | |
|---|---|---|
| CA | 2 526 540 | 12/2004 |
| EP | 0002892 | 7/1979 |
| EP | 0100172 | 2/1984 |
| EP | 0494819 | 7/1992 |
| EP | 0578516 | 1/1994 |
| EP | 0580459 | 1/1994 |
| FR | 2671348 A1 | 7/1992 |
| FR | 2693461 A1 | 1/1994 |
| JP | 2002088073 A | 3/2002 |
| WO | WO 95/18794 | 7/1995 |
| WO | WO 96/19458 | 6/1996 |
| WO | WO 97/00071 | 1/1997 |
| WO | WO 97/19064 | 5/1997 |
| WO | WO 97/23464 | 7/1997 |
| WO | WO 98/53826 | 12/1998 |
| WO | WO 99/46279 | 9/1999 |
| WO | WO 00/37430 | 6/2000 |
| WO | WO 01/16108 | 3/2001 |
| WO | WO 01/16133 | 3/2001 |
| WO | WO 02/00617 | 1/2002 |
| WO | WO 02/24702 | 3/2002 |
| WO | WO 03/022835 | 3/2003 |
| WO | WO 2004/099188 | 11/2004 |
| WO | WO 2004/111012 | 12/2004 |
| WO | WO 2004/113309 | 12/2004 |
| WO | WO 2005/066194 | 1/2005 |
| WO | WO 2005/040136 | 5/2005 |
| WO | WO 2005/120483 | 12/2005 |
| WO | WO 2006/133567 | 6/2006 |

OTHER PUBLICATIONS

International Search Report dated Oct. 17, 2006.
U.S. Appl. No. 11/030,850, filed Jan. 7, 2005 by Fernand Labrie et al., entitled "*Helix 12 Pharmaceutical Products*".
Office Action dated Mar. 10, 2009 issued in U.S. Appl. No. 11/030,850, filed Jan. 7, 2005.
U.S. Appl. No. 12/100,372, filed Apr. 9, 2008 by Fernand Labrie et al., entitled "*17Alpha Substituted Steroids as Systemic Antiandrogens and Selective Androgen Receptor Modulators*".
Patent Family Abstract of WO2006013887 filed Aug. 3, 2005 and entitled Preparation of Imidazolidine Derivatives as Androgen Receptor Antagonists.
Patent family search for JP 2002088073 (Dialog eLink 2/5/1 Dialog(R) File 351:Derwent WPI, New anti-androgen agent, containing cyanophenyl derivative, for prevention or treatment of prostatic cancer or prostatic hypertrophy, http://www.dialogclassic.com/mainframe.html Nov. 25, 2009.
Singh et al., Non-Steroidal Antiandrogens, Flutamide Derivatives as Antiandrogens, Current Medicinal Chemistry, 2000, vol. 7. No. 2.

*Primary Examiner*—Taofiq A Solola
(74) *Attorney, Agent, or Firm*—Ostrolenk Faber LLP

(57) ABSTRACT

Compounds having the structure (or their salts):

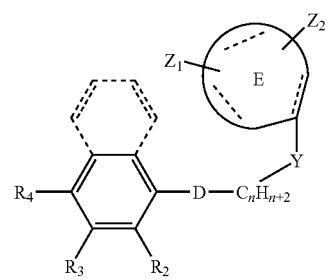

are used to treat or reduce the likelihood of acquiring androgen-dependent diseases, such as prostate cancer, benign prostatic hyperplasia, polycystic ovarian syndrome, acne, hirsutism, seborrhea, androgenic alopecia and male baldness. The compounds can be formulated together with pharmaceutically acceptable diluents or carriers or otherwise made into any pharmaceutical dosage form. Combinations with other active pharmaceutical agents are also disclosed.

42 Claims, 6 Drawing Sheets

A:

B:

HELIX 12 DIRECTED NON-STEROIDAL ANTIANDROGENS

CROSS-REFERENCE TO RELATED APPLICATIONS

This application claims the benefit of the priority of Provisional Application No. 60/691,391 filed Jun. 17, 2005, the contents of which are specifically incorporated by reference herein.

BACKGROUND OF THE INVENTION

This invention relates to novel inhibitors of sex steroid activity, for example to compounds having antagonistic activity on sex steroid receptors. More particularly, the invention relates to certain compounds having specified side-chains which interact with the helix 12 of the androgen receptor and metabolites thereof which block androgen action by acting, among other mechanisms, through the androgen receptors, while not activating such receptors in some or all androgen-sensitive tissues.

BRIEF DESCRIPTION OF THE PRIOR ART

During the treatment of certain androgen-dependent diseases, it is important to greatly reduce or, if possible, to eliminate androgen-induced effects. For this purpose, it is desirable to both block access to the androgen receptors with "antiandrogens", thus preventing androgens from binding and activating those receptors, and also to reduce the concentration of androgens available to activate the receptors. It is possible that, even in the absence of androgens, unoccupied androgen receptors may be biologically active. Hence, antiandrogens which bind and block the receptors may produce better therapeutic results than therapy which only inhibits androgen production.

Antiandrogens may have a significant therapeutic effect in slowing or stopping the progress of androgen-dependent diseases, e.g. diseases whose onset or progress is aided by androgen receptor or androgen receptor modulator activation.

It is desired that an antiandrogen used in therapy to reduce androgen receptor activation have both good affinity for the androgen receptor and a substantial lack of inherent androgenic activity in the tissue(s) of interest. The former refers to the ability of an antiandrogen to bind to the androgen receptor, and thus to block access to the receptor by androgens. The latter refers to the effect the antiandrogen has on the receptor once it binds thereto. Some antiandrogens may possess inherent androgenic activity ("agonistic activity") which undesirably activates the very androgen receptors whose activation they are intended to prevent the action. In other words, an antiandrogen with undesirable intrinsic androgenic activity may successfully bind to androgen receptors, desirably blocking access to those receptors by natural androgens, yet may undesirably itself activate the receptor in tissues where an exclusive antiandrogenic action is desired.

Known non-steroidal antiandrogens such as flutamide, casodex and anandron lack undesirable androgenic activity, but may have low receptor affinity compared to steroidal antiandrogens (i.e. androgen derivatives having a steroidal nucleus that is modified to provide antiandrogenic activity). Steroidal antiandrogens, however, are believed to more frequently possess undesirable agonistic characteristics, than non-steroidal antiandrogens. Recently, some new non-steroidal antiandrogens possessing long substituents and having a better activity than the above-mentioned non-steroidal antiandrogens were described (Kawaminami et al., 2005, Kinoyama et al., 2004, Tucker et al., 2004) disclosed (U.S. Pat. No. 5,411,981, U.S. Pat. No. 6,071,957, US 2004/0077605, US 2004/0077606, EP 0 100 172, FR 91 00185, FR 92 08431, EP 002 892, EP 0 494 819, EP 0 578 516, EP 0 580 459, WO 95/18794, WO 96/19458, WO 97/00071, WO 97/19064, WO 97/23464, WO 98/53826, Japanese P2002-88073A), WO 00/37430 WO 01/16108, WO 01/16133, WO 02/24702, WO 2004/099188, WO 2004/111012, WO 2004/113309, WO 2005/040136.

However, steroidal antiandrogens with very high affinity for the androgen receptor and lacking undesirable agonistic characteristic were disclosed in the U.S. patent application Ser. No. 11/030,850 based upon provisional application No. 60/535,121. These compounds possess specified side-chains at position 18 and which interact with helix 12.

Selective Androgen Receptor Modulators (SARMs) having antagonist activity in some tissues while exhibiting no activity or agonist activity in other tissues were reported in WO 02/00617, WO 2005/120483, US 2005/0033074, US 2005/0250741, US 2006/0014739, US 2006/0009529. Some of these SARMs are in clinical trials for building muscle and promoting bone (Ostarine developped by GTx in United States), hypogonadism, benign prostatic hyperplasia, osteoporosis and female sexual dysfunction (LGD 2226 2941 developed by Ligand in United States) or age-related decline (BMS 564929 developed by Bristol-Myers Squibb in United States).

There is thus a need in the art for non-steroidal antiandrogens having high affinity for the androgen receptor, while substantially lacking undesirable agonistic characteristics and having a good parenteral or oral bioavailability for systemic uses.

SUMMARY OF THE INVENTION

It is an object of the present invention to provide antiandrogens, having good affinity for the androgen receptor, while substantially lacking androgenic activity. These antiandrogens may be useful in the treatment and prevention of androgen-dependent diseases as described in more detail infra.

It is an object of the present invention to provide a compound which:

a) binds the androgen receptor;

c) interferes directly or indirectly with helix 12 of the androgen receptor by means of a chain sufficiently narrow and long to pass through the channel joining the steroid active site to helix 12;

d) and blocks normal helix 12-positioning when the androgen receptor is bound by an agonist.

In one embodiment, the present invention provides a compound of the following schematic molecular formula, or a salt of thereof:

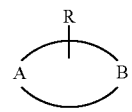

wherein

is a nucleus able to bind to the steroid active site of the androgen receptor;
and wherein R is a chain approximately perpendicularly positioned to the plane of the

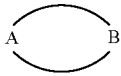

nucleus, containing an aromatic or heteroaryl ring, which is sufficiently narrow and long to pass through the channel joining the steroid active site to helix 12 having at least one polar functional group distanced from the

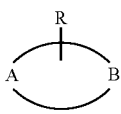

nucleus by 6 to 10 angstroms and selected from the list consisting of carbonyl, sulfone or sulfoxide, sulfimide, amine, amide, N-oxide, and quaternary ammonium salt.

It is an object of the present invention to provide a pharmaceutical composition comprising a pharmaceutically acceptable diluent or carrier and a therapeutically effective amount of at least one compound which:
a) binds the androgen receptor;
c) interferes directly or indirectly with helix 12 of the androgen receptor by means of a chain sufficiently narrow and long to pass through the channel joining the steroid active site to helix 12;
d) and blocks the normal helix 12-positioning when the androgen receptor is bound by an agonist.

In one embodiment, the invention provides a pharmaceutical composition comprising a pharmaceutically acceptable diluent or carrier and a therapeutically effective amount of at least one compound of the following molecular formula or a salt of thereof:

wherein

is a nucleus able to bind to the steroid active site of the androgen receptor;
and wherein R is a chain approximately perpendicularly positioned to the plane of the

nucleus, containing an aromatic or heteroaryl ring, being sufficiently narrow and long to pass through the channel joining the steroid active site to helix 12, having at least one polar functional group distanced from the

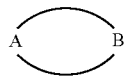

nucleus by 6 to 10 angstroms and being selected from the group consisting of carbonyl, sulfone or sulfoxide, sulfimide, amine, amide, N-oxide, and quaternary ammonium salt.

In one embodiment, the

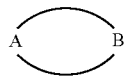

nucleus has the following structure:

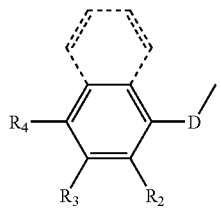

wherein dotted lines represent optional bonds;
wherein D is selected from the group consisting of an aromatic moiety, an heterocyclic moiety and a cyclic moiety;
wherein $R_2$ is selected from the group consisting of hydrogen and $(C_1-C_3)$ lower alkyl;
wherein $R_3$ and $R_4$ are independently selected from the group consisting of hydrogen, halogen, nitrile, —$COCH_3$, —$SO_2CH_3$, methyl, and halogenated methyl; wherein at least one of $R_3$ and $R_4$ is not hydrogen.

In another embodiment, R has the following structure:

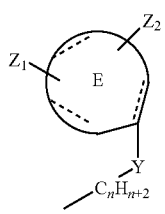

wherein n is an integer selected from 0 to 3;
wherein dotted lines represent optional bonds;

wherein E is selected from the group consisting of an aromatic moiety and a heteroaryl moiety;

wherein Y is a spacing group having one to four atoms;

wherein $Z_1$ is a hydrocarbon moiety additionally having at least one carbonyl, sulfone, or sulfoxide group or a nitrogen atom separated from E by none to four intervening atoms, and said nitrogen atom being an amine, an amide, an N-oxide, sulfimide or a quaternary ammonium salt, $Z_1$, optionally, having other oxygen, sulphur, or nitrogen atoms;

wherein $Z_2$ is selected from the group consisting of hydrogen, fluorine, chlorine, bromine, iodine, cyano, nitro, trifluoromethyl, alkoxy, $C_1$-$C_5$ straight or branched alkyl, $C_2$-$C_5$ straight or branched alkenyl, and $C_2$-$C_5$ straight or branched alkynyl.

In another embodiment, the invention provides a compound having the following schematic molecular formula or a salt of thereof:

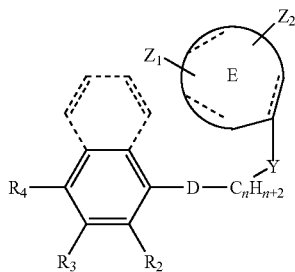

wherein n is an integer selected from 0 to 3;

wherein dotted lines represent optional bonds;

wherein D is selected from the group consisting of an aromatic moiety, an heterocyclic moiety and a cyclic moiety;

wherein E is selected from the group consisting of an aromatic moiety and a heteroaryl moiety;

wherein $R_2$ is selected from the group consisting of hydrogen or lower ($C_1$-$C_3$) alkyl;

wherein $R_3$ and $R_4$ are independently selected from the group consisting of hydrogen, halogen, nitrile, —$COCH_3$, —$SO_2CH_3$, —$NO_2$, —$OCH_3$, —$SCH_3$, methyl, and halogenated methyl; wherein at least one of $R_3$ and $R_4$ is not hydrogen;

wherein Y is a spacing group having one to four atoms;

wherein $Z_1$ is a hydrocarbon moiety additionally having at least a one carbonyl, sulfone or sulfoxide group or nitrogen atom separated from E by none to four intervening atoms, and said nitrogen atom being an amine, an amide, an N-oxide, or a quaternary ammonium salt, $Z_1$, optionally, having other oxygen, sulphur, or nitrogen atoms;

wherein $Z_2$ is selected from the group consisting of hydrogen, fluorine, chlorine, bromine, iodine, cyano, nitro, trifluoromethyl, alkoxy, $C_1$-$C_5$ straight or branched alkyl, $C_2$-$C_5$ straight or branched alkenyl, and $C_2$-$C_5$ straight or branched alkynyl.

wherein $R_2$ is selected from the group consisting of hydrogen or lower ($C_1$-$C_3$) alkyl;

wherein $R_3$ and $R_4$ are independently selected from the group consisting of hydrogen, halogen, nitrile, —$COCH_3$, —$SO_2CH_3$, $NO_2$, $OCH_3$, $SCH_3$, methyl, and halogenated methyl; wherein at least one of $R_3$ and $R_4$ is not hydrogen;

wherein Y is a spacing group having one to four atoms;

wherein $Z_1$ is a hydrocarbon moiety additionally having at least a one carbonyl, sulfone or sulfoxide group or nitrogen atom separated from E by one to four intervening atoms, and said nitrogen atom being an amine, an amide, an N-oxide, or a quaternary ammonium salt, $Z_1$, optionally, having other oxygen, sulphur, or nitrogen atoms;

wherein $Z_2$ is selected from the group consisting of hydrogen, fluorine, chlorine, bromine, iodine, cyano, nitro, trifluoromethyl, alkoxy, $C_1$-$C_5$ straight or branched alkyl, $C_2$-$C_5$ straight or branched alkenyl, and $C_2$-$C_5$ straight or branched alkynyl.

In another embodiment, the invention provides a pharmaceutical composition comprising a pharmaceutically acceptable diluent or carrier and a therapeutically effective amount of at least one compound of the following molecular formula, or a salt of thereof:

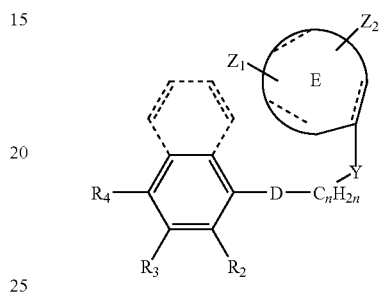

wherein n is an integer selected from 0 to 3;

wherein dotted lines represent optional bonds;

wherein D is selected from the group consisting of an aromatic moiety, an heterocyclic moiety and a cyclic moiety;

wherein E is selected from the group consisting of an aromatic moiety and a heteroaryl moiety;

wherein $R_2$ is selected from the group consisting of hydrogen and lower ($C_1$-$C_3$) alkyl;

wherein $R_3$ and $R_4$ are independently selected from the group consisting of hydrogen, halogen, nitrile, —$COCH_3$, —$SO_2CH_3$, —$NO_2$, —$OCH_3$, —$SCH_3$, methyl, and halogenated methyl; wherein at least one of $R_3$ and $R_4$ is not hydrogen;

wherein Y is a spacing group having one to four atoms;

wherein $Z_1$ is a hydrocarbon moiety additionally having at least a one carbonyl, sulfone or sulfoxide group or nitrogen atom directly linked or separated from E by none to four intervening atoms, and said nitrogen atom being an amine, an amide, an N-oxide, or a quaternary ammonium salt, $Z_1$, optionally, having other oxygen, sulphur, or nitrogen atoms;

wherein $Z_2$ is selected from the group consisting of hydrogen, fluorine, chlorine, bromine, iodine, cyano, nitro, trifluoromethyl, alkoxy, $C_1$-$C_5$ straight or branched alkyl, $C_2$-$C_5$ straight or branched alkenyl, and $C_2$-$C_5$ straight or branched alkynyl.

In another embodiment, the invention provides topical or systemic pharmaceutical compositions containing the compounds of the invention together with pharmaceutically acceptable diluents or carriers.

In another aspect, compounds of the invention, or pharmaceutical compositions containing them, are used in the treatment or prevention of androgen-exacerbated skin related diseases such as acne, hirsutism, seborrhea, androgenic alopecia, male baldness and the like.

In another embodiment, compounds of the invention are used in the treatment or prevention of androgen-exacerbated systemic diseases such as prostate cancer or benign prostatic hyperplasia, precocious puberty, polycystic ovarian syndrome, hyperrandrogenic syndromes, and the like.

In another embodiment, treatment and prevention regimens for androgen-exacerbated diseases include use of the compounds disclosed herein, as part of a combination therapy which further utilizes other active compounds selected from the group consisting of 5alpha-reductase inhibitor, 17beta-hydroxysteroid dehydrogenase type 5 and type 13 inhibitors, Prostate, and other inhibitors of androgen biosynthesis.

In another aspect, compounds of the present invention having tissue-specific antiandrogenic activity and tissue-specific androgenic activity can be used to treat or reduce the risk of developing diseases related to loss of androgenic stimulation.

It is another object to provide selective androgen receptor modulators for treatment (or reduction of the likelihood of acquiring) diseases related to loss of androgen stimulation.

In another aspect, compounds of the invention are used in the manufacture of a medicament for treatment of diseases discussed herein.

It is another object to provide pharmaceutical compounds with good systemic bioavailability.

DETAILED DESCRIPTION OF THE PREFERRED EMBODIMENTS

Figure 1:
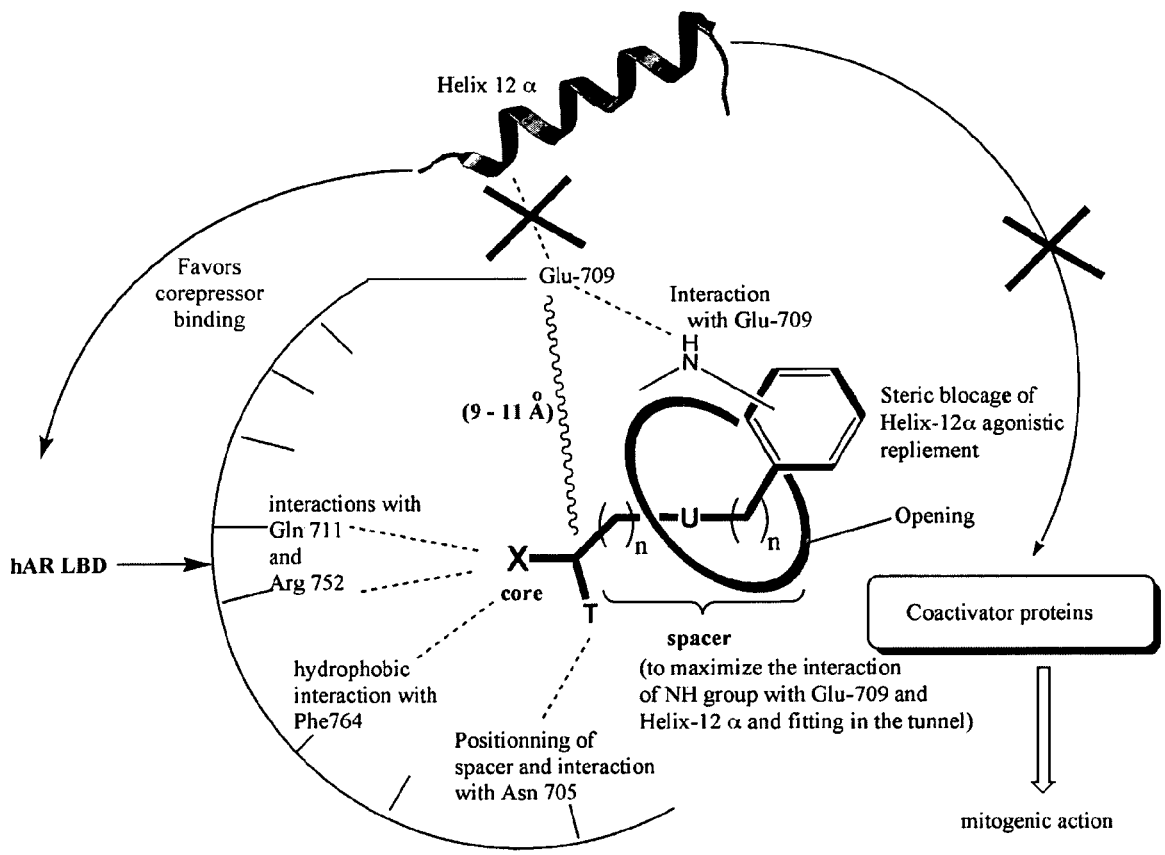
FIG. 1 shows a schematic representation of the principle of action of non steroidal androgen receptor antagonists of the invention.

Previous structural studies on the hERα(LBD)-raloxifene crystal complex have revealed the structural basis of the mechanism of antagonism by raloxifene. It was then shown that the antagonist binds at the same site where the agonist binds within the core of the LBD but the two ligands demonstrate different binding modes. Indeed, each class of ligand induces a distinct conformation in the transactivation domain which is characterized by the different positioning of helix 12. Our molecular modeling work based upon the crystallographic structure of the hAR(LBD)-R1881 complex (see Ishioka et al., Novel Non-Steroidal/Non-Anilide Type Androgen Antagonists with Isoxazolone Moiety, Bioorganic & Medicinal Chemistry 10 (2002) 1555-1566; Muddana et al. 11β-alkyl-$\Delta^9$-19-Nortestosterone Derivatives: High-Affinity Ligands and Potent Partial Agonists of the Androgen Receptor, J. Med. Chem. 2004, 47, 4985-4988) has discovered a narrow channel between the steroid binding site and the site occupied by helix 12. We discovered that this narrow channel, mainly formed by the side chains of 5 residues ($Asn_{705}$, $Trp_{741}$, $Met_{742}$, $Thr_{877}$, and $Phe_{891}$) of the androgen receptor could accommodate a side chain only if it is positioned on carbon 18 of an androgen steroid nucleus. From this position on the steroid nucleus, a thin side chain passing through this opening could reach the surface of the receptor and disturb helix 12 positioning. By extension to non-steroid compounds, we have found that compounds with a nucleus which are able to bind to some of aminoacid residues of the steroid active site of the hAR(LBD) and which possess a side chain in the right position to be able to pass through the above-described discovered channel can be good candidates to be good antagonist of the human androgen receptor. hERα(LBD) and hAR (LBD) mean human type α Estrogen Receptor Ligand Binding Domain and human Androgen Receptor Ligand Binding Domain, respectively.

Our invention is based on the above-summarized finding and provides compounds and pharmaceutical compositions containing such compounds. Accordingly, compounds which are able to bind the androgen receptor and which possess a chain sufficiently narrow and long to pass through this above-described channel must interfere with helix 12 and block its normal positioning, should be a good antagonist. All preferences stated herein may be used in combination. For example, preferred substituents at any position of the molecular structures described may be used with preferred substituents at any other position.

Many compounds with long substituents have been synthesized in our laboratory and tested for their capacities to bind the androgen receptor and to inhibit the DHT-stimulated growth of the androgen-sensitive mouse Shionogi mammary carcinoma cells. In the majority of cases, these molecules bind the receptor with high affinity but remain potent agonists. However, we have also obtained many very potent antagonists having a high affinity for the receptor, thus indicating that the structure of the side chain is of paramount importance. To understand the molecular basis of the agonistic and antagonistic properties of these different molecules, and to verify that a side chain positioned as predicted is really able to pass through the channel and reach helix 12, we have attempted to crystallize some of these molecules (androgens and antiandrogens) in complex with the human androgen receptor ligand binding domain (hAR(LBD)) in order to determine and compare the tridimensional structures of these complexes. We have now obtained the complete structure for one of them (hAR(LBD)-EM-5744) determined at a 1.75 Å resolution.

EM-5744 is a DHT-based ligand possessing a strong affinity for the human androgen receptor in spite of its long side chain substituent added to the carbon atom at position 18 (see structure below). Indeed, the ligand EM-5744 binds with a relative binding affinity of 540 to the wild-type hAR as compared with a value of 180 for DHT and 100 for R1881. This ligand could be considered as an agonist since it fails to inhibit the DHT-stimulated growth of Shionogi cells when added to the culture medium at a concentration of $10^{-6}$ M while it

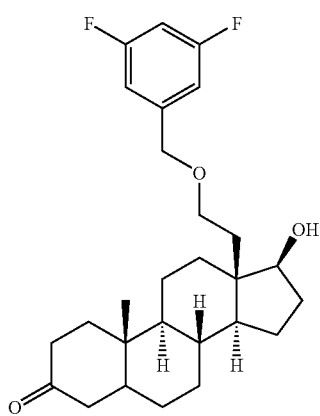

possesses a significant agonistic activity at $10^{-7}$ M.

Figure 2:
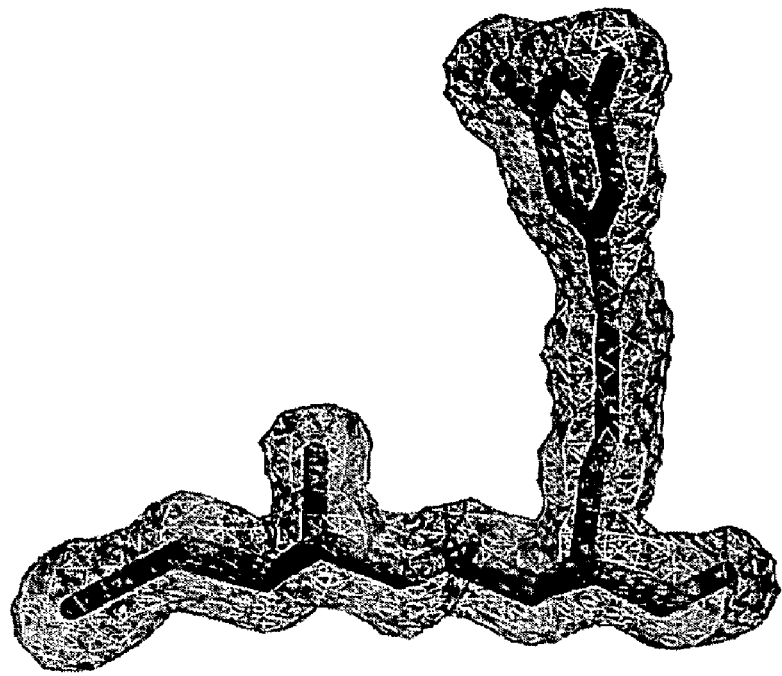
FIG. 2 (A: side-view, B: top-view) shows the electron density around the EM-5744 molecule. The 2Fo-Fc map, computed with 1.75 Å resolution data, is illustrated at a 1σ level.
Figure 2:
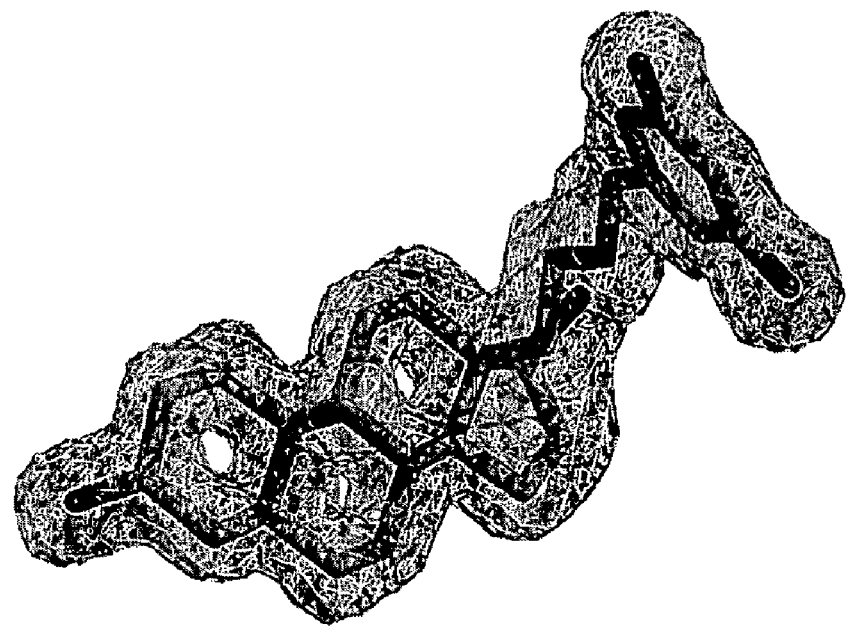
Figure 3:
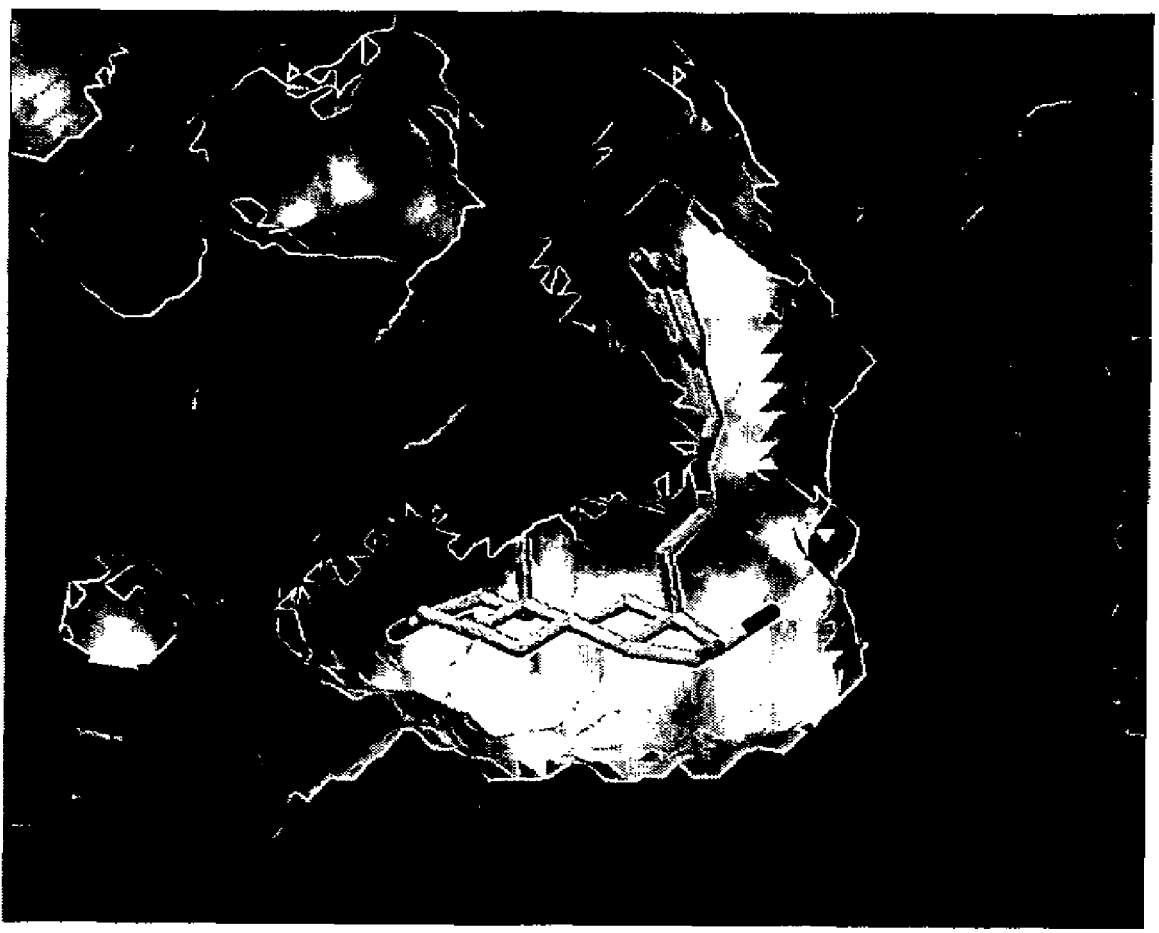
FIG. 3 shows the electrostatic surface representing the ligand binding cavity in the hAR(LBD)-EM-5744 complexed structure. The surface is colored according to the electrostatic potential: grey for positive or negative, white for neutral

As illustrated in FIGS. 2 and 3, in the crystallographic structure which has been determined, the steroid nucleus of EM-5744 is positioned within the ligand binding cavity and there are a total of 18 amino acid residues in hAR LBD that interact with the bound ligand (d≦3.9 Å). Most of these residues are hydrophobic and interact mainly with the steroid scaffold, whereas a few are polar and may form hydrogen bonds to the polar atoms on the ligand. The oxygen atom (O-3) of the A ring carbonyl group forms a hydrogen bond to $Arg_{752}$ (2.9 Å to $Arg_{752}$ $N^{\eta 2}$). There is also a water molecule near O-3 (3.2 Å) that is hydrogen-bonded to two other residues ($Arg752$ $N^{\eta 2}$ and $Met_{745}$). The 17β hydroxyl group of EM-5744 forms hydrogen bonds to $ASN_{705}$ $O^{\delta 1}$ (2.8 Å) and $Thr_{877}$ $O^{\gamma}$ (2.8 Å), this being the same pattern observed in the hAR(LBD)-R1881 complex structure. Finally, the C-18 side chain is also well stabilized, mainly by numerous contacts with hydrophobic residues, and, as predicted, exits the steroid binding pocket through the channel. However, the side chain of EM-5744 is not well positioned to reach the cavity occupied by helix 12 and, consequently, can not disturb its positioning. This observation explains very well why this compound acts as an agonist in spite of the presence of its C-18 bulky side chain. Interestingly, an unexpected interaction has been observed between one of the fluor atoms at the extremity of the side chain of EM-5744 and the $N^{\eta 2}$ atom of residue His874. A water molecule found at close proximity of these two atoms could also be involved. This interaction probably explains the higher affinity of EM-5744 for the hAR compared to DHT or R1881 which do not possess this third bond with the receptor. In order to accommodate the C-18 substituent of EM-5744 in a similar manner, the side chain of residue $Trp_{741}$, a residue forming the channel, is flipped 180° around its $C^{\gamma}$ and adopts a conformation which is very different from that observed with the same residue in the hAR(LBD)-R1881 complex structure. Other residues forming the ligand cavity also adopt different conformations, a possible consequence of the $Trp_{741}$ side chain movement. The present observations illustrate the remarkable plasticity of both, the ligand binding cavity and the narrow channel through which the C-18 side chain of EM-5744 exits from the pocket.

As presented in FIG. 1, binding of androgen receptors by the present compounds may modify the binding of co-activators and co-repressors to the androgen receptor, thus leading to accelerated apoptosis in androgen-sensitive tissues. Anti-androgens may even lead to cell death.

Figure 4:
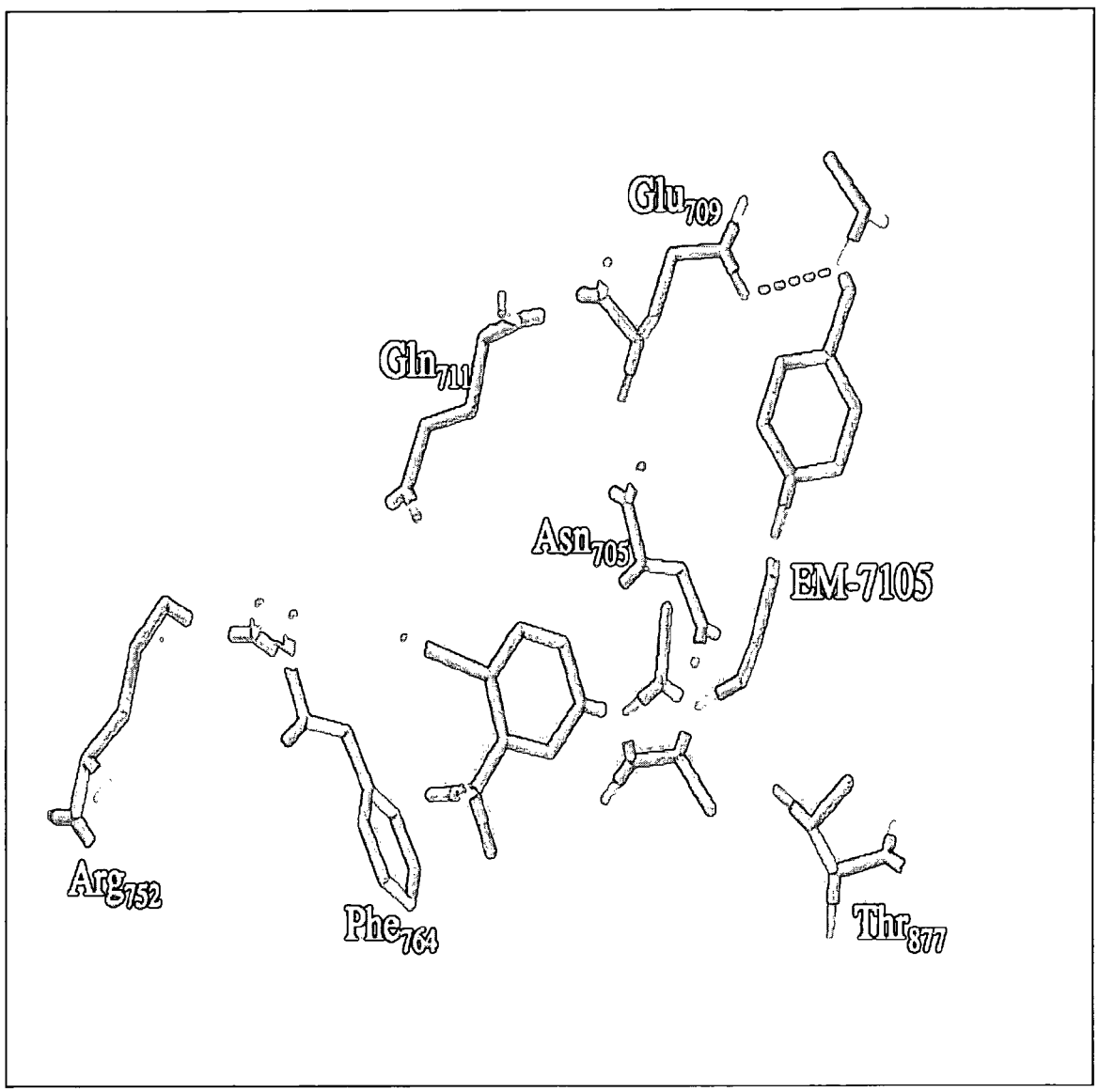
FIG. 4 shows the interactions of the antagonist EM-7105 with aminoacid residues of the ligand binding cavity in the hAR(LBD)-EM-7105 complexed structure.
Figure 5:
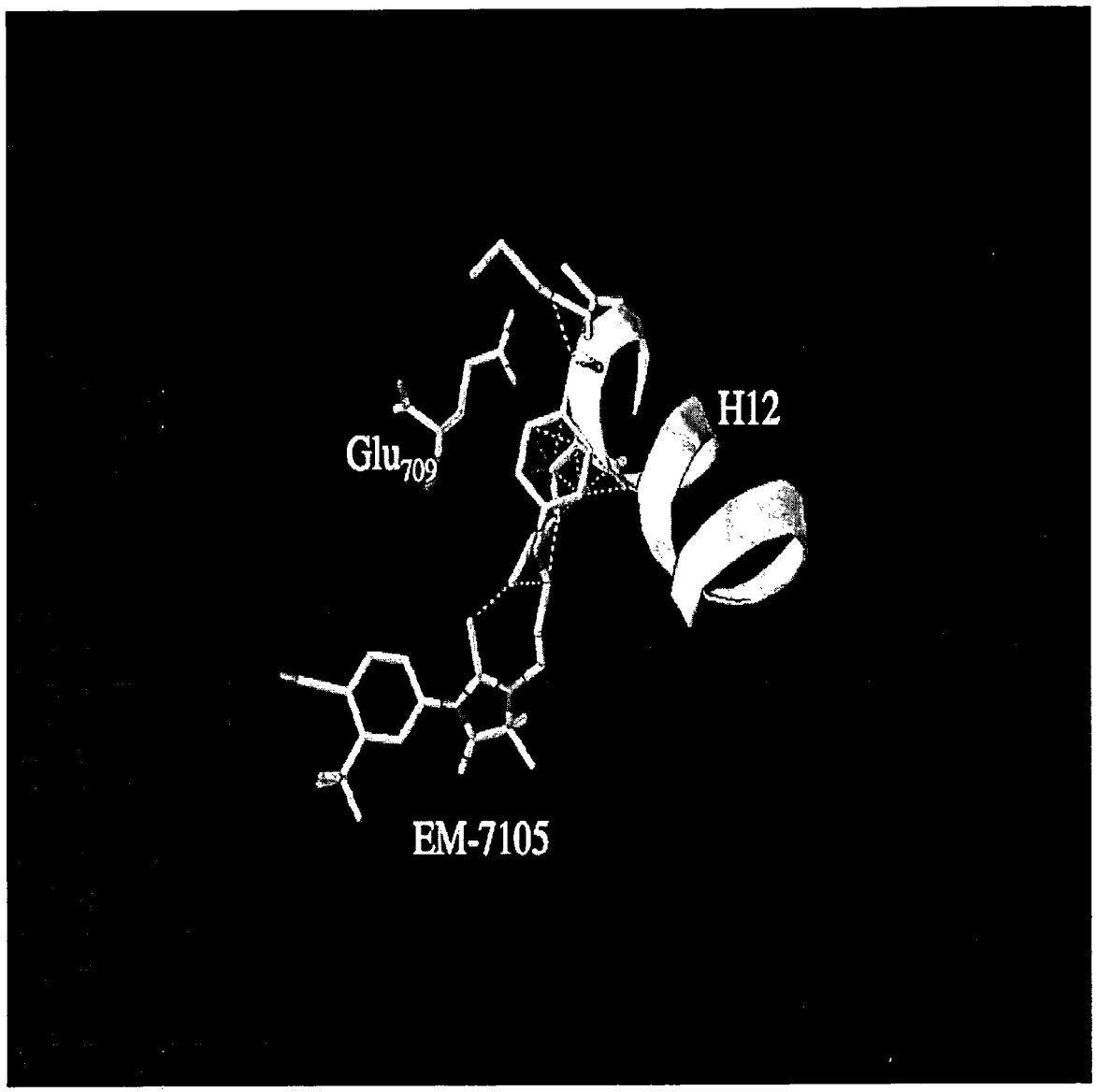
FIG. 5 shows the interactions of the side chain of the antagonist EM-7105 with the Helix 12α of the androgen receptor.
Figure 6:
FIG. 6 shows the electrostatic surface representing the channel joning the ligand binding cavity and the site occupied Helix 12α in the hAR(LBD)-EM-7105 complexed structure. The surface is colored according to the electostatic potential: grey for positive or negative, white for neutral. The interaction of nitrogen atom of the side chain of EM-7105 with the glutamide residue 709 is underlined. It can be seen that Helix 12α-repliement is blocked by the end of the side-chain.

FIGS. 4-6 show modelling of the hAR(LBD)-EM-7105 complex, wherein EM-7105 is a non-steroid antiandrogen of the invention. The nucleus of EM-7105 is positioned within the ligand binding cavity as shown in FIG. 4. Most of the hAR(LBD)-residues in this area are hydrophobic and interact mainly with the

nucleus, whereas the nitrogen on the side chain may form a hydrogen bond to the polar atoms on the glutamide 709 residue. It can be seen in FIGS. 5 and 6, that Helix 12α-repliement is blocked when this hydrogen bond takes place.

The present antiandrogens and pharmaceutical compositions containing them, may be utilized in accordance with the invention in the treatment of androgen-sensitive diseases whose progress is aided by activation of androgen receptors.

These include but are not limited to prostate cancer, benign prostatic hyperplasia, acne, seborrhea, hirsutism, androgenic alopecia, male baldness, precocious puberty, polycystic ovarian syndrome and the like.

In certain circumstances (e.g. at certain concentrations) the compounds of the invention, and pharmaceutical compositions containing them, can be androgenic and may be utilized in accordance with the invention in the prevention and treatment of diseases regarding which androgens are beneficial such as muscle atrophy, abdominal fat accumulation, skin atrophy, anemia, bone loss, osteoporosis, artherosclerosis, cardiovascular diseases, type 2 diabetes, loss of energy or well being.

It is preferred that the nucleus is selected from the following moieties:

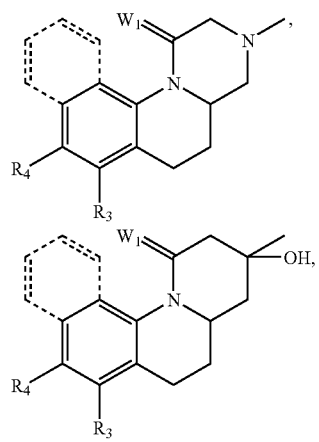

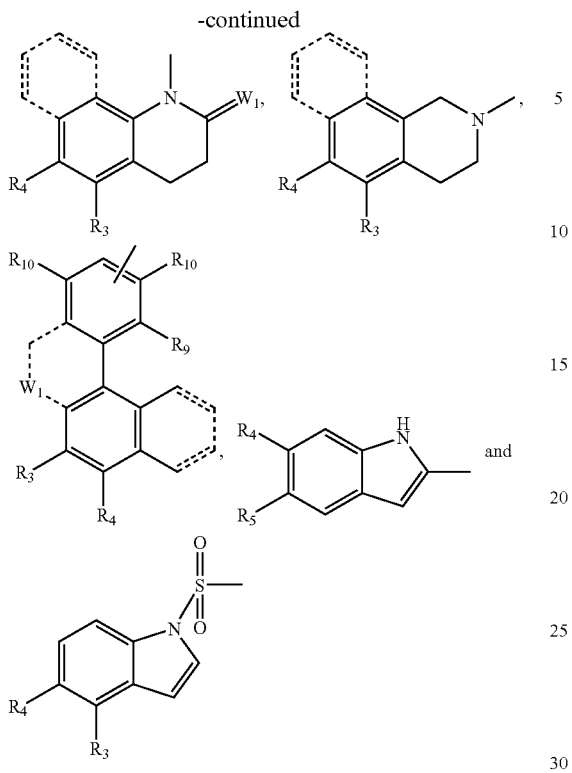

wherein dotted lines represent optional bonds;
wherein $R_3$ and $R_4$ are independently selected from the group consisting of hydrogen, halogen, nitrile, —$COCH_3$, —$SO_2CH_3$, —$NO_2$, —$OCH_3$, —$SCH_3$, methyl, and halogenated methyl; wherein at least one of $R_3$ and $R_4$ is not hydrogen;
wherein $R_9$ and $R_{10}$ are independently selected from the group consisting of hydrogen, hydroxyl, halogen and methyl;
wherein $W_1$ is selected from the group consisting of —$CH_2$—, oxygen and sulphur.

It is preferred that Y is selected from the group consisting of -$MCH_2CH_2$—, —$CH_2MCH_2$—, and —$CH_2CH_2M$- (M being selected from the group consisting of —O—, —S—, —$SO_2$—, and —$CH_2$—), more particularly —$CH_2CH_2O$—.

It is preferred that E is selected from the group consisting of phenylene and mono-substituted pyridyl and wherein Z1 is located in the para position with respect to the group Y and the nitrogen atom of Z1 is separated from the phenylene or mono-substituted pyridyl ring by one intervening atoms, more particularly Z1 is selected from the following moieties:

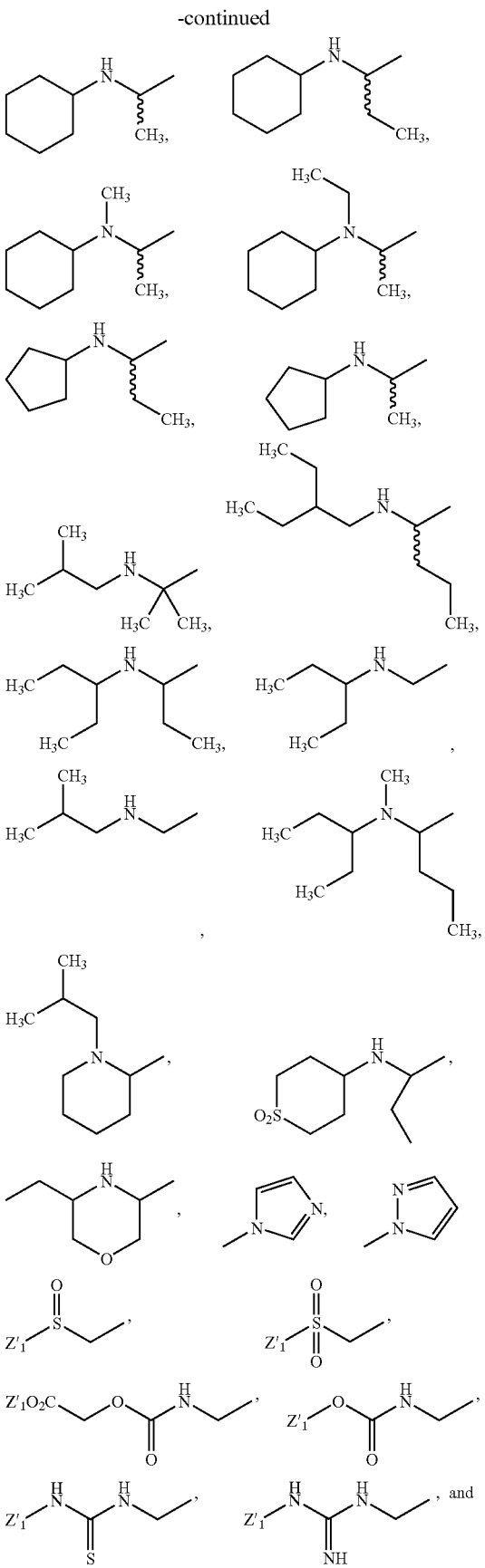

-continued

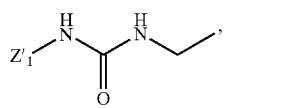

($Z'_1$ being hydrogen, lower $C_1$-$C_6$ alkyl, alkylene or aryl) or $Z_1$ fusioned with the Cycle B forms a bicycle moiety selected from the group consisting of:

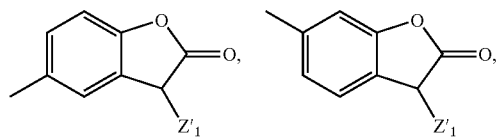

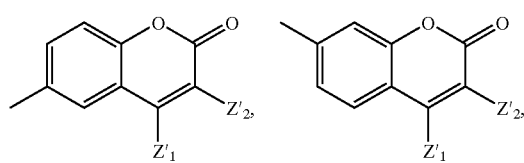

($Z'_1$ and $Z'_2$ being independently hydrogen, lower $C_1$-$C_6$ alkyl, alkylene or aryl)

It is preferred that D is selected from the group consisting of

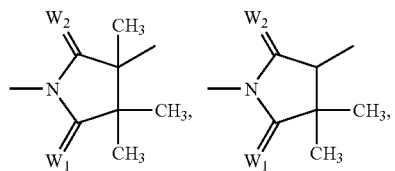

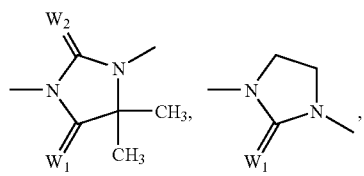

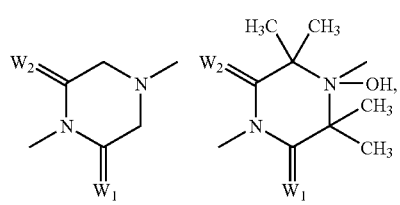

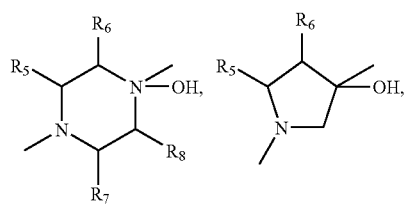

-continued

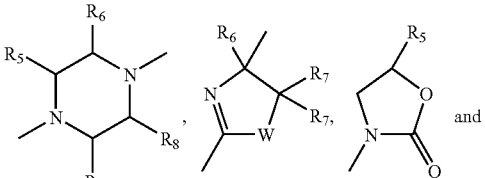

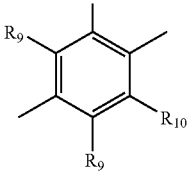

wherein $W_1$ and $W_2$ are independently selected from the group consisting of —$CH_2$—, oxygen and sulphur;

wherein $R_5$, $R_6$, $R_7$, and $R_8$ are independently selected from the group consisting of hydrogen and ($C_1$-$C_3$) lower alkyl; and wherein $R_9$ and $R_{10}$ are independently selected from the group consisting of hydrogen, hydroxyl, halogen and methyl.

Compounds of the following molecular formulae or a salt thereof, and pharmaceutical composition comprising them, are prefered:

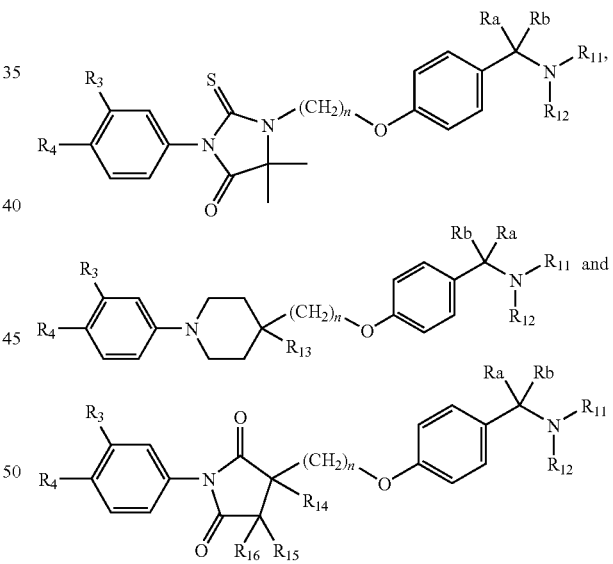

wherein n is an interger from 1 to 3;

wherein Ra and Rb are independently selected from the group consisting of hydrogen and C1-C6 alkyl, C2-C6 alkenyl; Ra and Rb together may form a ring;

wherein $R_3$ is selected from the group consisting of hydrogen, halogen, $OCH_3$, $SCH_3$, alkylsulfoxide, alkylsulfone sulfone, nitrile, $NO_2$, alkyl, methyl, and trifluoromethyl;

wherein $R_4$ is selected from the group consisting of halogen, nitrile, —$COCH_3$, —$SO_2CH_3$, and —$NO_2$;

wherein $R_{11}$ and $R_{12}$ are independently selected from the group consisting of hydrogen and $C_1$-$C_6$ lower alkyl or $R_{11}$ and $R_{12}$ together form a heterocycle optionally having another heteroatom selected from the group consisting of nitrogen, oxygen, selenium, silicium and sulphur;

wherein $R_{13}$ is selected from the group consisting of hydrogen, hydroxyl and $C_1$-$C_6$ lower alkyl;

wherein $R_{14}$ is selected from the group consisting of hydrogen, hydroxyl and $C_1$-$C_6$ lower alkyl; wherein $R_{14}$ and $R_{15}$ together may form a $C_4$-$C_8$ ring or $C_4$-$C_8$ heterocycle;

wherein $R_{15}$ is selected from the group consisting of hydrogen and $C_1$-$C_6$ lower alkyl. $R_{13}$ and $R_{14}$ together may form a $C_4$-$C_8$ ring or $C_4$-$C_8$ heterocycle; and wherein $R_{16}$ is selected from the group consisting of hydrogen and $C_1$-$C_6$ lower alkyl.

Compounds having a molecular structure selected from the group consisting of the following, or a salt of thereof, and pharmaceutical compositions comprising them, are particularly preferred:

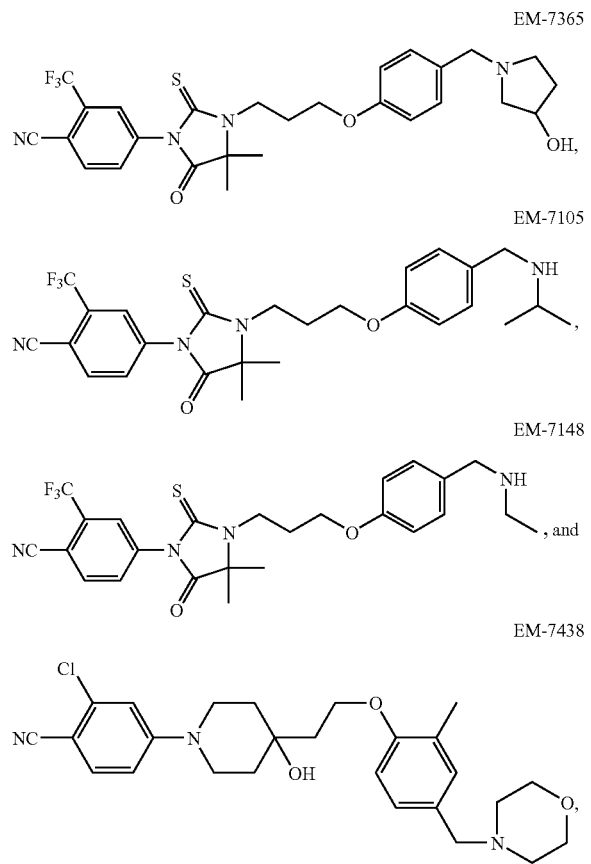

In some embodiments, it is preferred that $R_{11}$ or $R_{12}$ is a cyclopentyl, cyclohexyl or cycloheptyl radical.

In some embodiments, it is preferred that Ra and Rb are independently selected from the group consisting of hydrogen, methyl and ethyl.

It is preferred that $Z_2$ is selected from the group consisting of hydrogen, fluorine, chlorine and cyano.

It is preferred that n is 3.

In preferred embodiments two or preferably more of the preferences herein are used in combination.

The antiandrogens of the invention are preferably formulated together with pharmaceutically acceptable diluents, excipients or carriers (including capsules) into pharmaceutical compositions at conventional antiandrogen concentrations for antiandrogens used in the prior art. Taking into account the higher potency of the compounds of this invention, the attending clinician may elect to modify the concentration and/or dosage in order to adjust the dose to the particular response of each patient. Preferably, the attending clinician will, especially at the beginning of treatment, monitor an individual patient's overall response and serum levels of antiandrogen (in comparison to the preferred serum concentrations discussed below), and monitor the patient's overall response to treatment, adjusting dosages as necessary where a given patients' metabolism or reaction to treatment is atypical. As discussed in more detail below, carriers, excipients or diluents include solids and liquids. When a composition is prepared other than for immediate use, an art-recognized preservative is typically included (e.g. benzyl alcohol). The novel pharmaceutical compositions of the invention may be used in the treatment of androgen-related diseases, or to reduce the likelihood of acquiring such diseases. When administered systemically (e.g., for treatment of prostate cancer, benign prostatic hyperplasia, precocious puberty, polycystic ovarian syndrome and other diseases not primarily affecting the skin) conventional diluents or carriers which are known in the art to be pharmaceutically acceptable for systemic use are used, e.g., saline, water, aqueous ethanol, oil, etc. The carrier is often a mixture of ingredients.

When formulated for systemic use, the antiandrogens may be prepared for administration in conventional ways such as orally or by injection. The antiandrogen can be administered, for example, by the oral route. The compounds of the present invention may be formulated with conventional pharmaceutical excipients, (e.g. spray dried lactose and magnesium stearate) into tablets or capsules for oral administration. Of course, taste-improving substances can be added in the case of oral administration forms. When capsules for oral ingestion are desired, any pharmaceutical capsules known in the art may be filled with the active ingredients of the invention, with or without additional diluents and other additives discussed herein.

The active substance can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycol.

As further forms, one can use plug capsules, e.g., of hard gelatin, as well as closed soft-gelatin capsules comprising a softener or plasticizer, e.g., glycerine. The plug capsules contain the active substance preferably in the form of granulate, e.g., in mixture with fillers, such as lactose, saccharose, mannitol, starches, such as potato starch or amylopectin, cellulose derivatives or highly dispersed silicic acids. In soft-gelatin capsules, the active substance is preferably dissolved or suspended in suitable liquids, such as vegetable oils or liquid polyethylene glycols.

A dry delivery system, as described in U.S. Pat. Nos. 3,742, 951, 3,797,494 or 4,568,343 may be used.

Alternatively, the active ingredient may be placed into a transdermal patch having structures known in the art, for example, structures such as those set forth in E.P. Patent No. 0279982.

Solvents or devices as described in U.S. Pat. Nos. 5,064, 654, 5,071,644 or 5,071,657 can also be used to facilitate transdermal penetration when systemic effects are desired. When used to treat systemic diseases, the site of application on the skin should be changed in order to avoid excess local concentration of antiandrogens.

In some embodiments, the antiandrogens of the invention are utilized for the treatment of androgen-related diseases of the skin such as acne, seborrhea, hirsutism, androgenic alopecia and male baldness. When used for any of these purposes, the antiandrogens are preferably administered topically together with a conventional topical carrier or diluent. When used topically, it is preferred that the diluent or carrier does not promote transdermal penetration of the active ingredients into the blood stream or other tissues where they might cause unwanted systemic effects.

When the compound is administered in a cutaneous or topical carrier or diluent, the carrier or diluent may be chosen from any known in the cosmetic and medical arts, e.g. any gel, cream, lotion, ointment, liquid or non liquid carrier, emulsifier, solvent, liquid diluent or other similar vehicle which does not exert deleterious effect on the skin or other living animal tissue. The carrier or diluent is usually a mixture of several ingredients, including, but not limited to liquid alcohols, liquid glycols, liquid polyalkylene glycols, water, liquid amides, liquid esters, liquid lanolin, lanolin derivatives and similar materials. Alcohols include mono and polyhydric alcohols, including ethanol, glycerol, sorbitol, isopropanol, diethylene glycol, propylene glycol, ethylene glycol, hexylene glycol, mannitol and methoxyethanol. Typical carriers may also include ethers, e.g. diethyl and dipropyl ether, methoxypolyoxyethylenes, carbowaxes, polyethyleneglycerols, polyoxyethylenes and sorbitols. Usually, the topical carrier includes both water and alcohol in order to maximize the hydrophylic and lipophylic solubility, e.g. a mixture of ethanol or isopropanol with water.

A topical carrier may also include various other ingredients commonly used in ointments and lotions and well known in the cosmetic and medical arts. For example, fragrances, antioxidants, perfumes, gelling agents, thickening agents such as carboxymethylcellulose, surfactants, stabilizers, emollients, coloring agents and other similar agents may be present.

The concentration of active ingredient in the ointment, cream, gel or lotion is typically from about 0.1 to 20 percent, preferably between 0.5 and 5 percent and most preferably 2 percent (by weight relative to the total weight of the lotion, cream, gel or ointment). Within the preferred ranges, higher concentrations allow a suitable dosage to be achieved while applying the lotion, ointment, gel or cream in a lesser amount or with less frequency.

Several non-limiting examples infra describe the preparation of a typical lotion and gel, respectively. In addition to vehicles, one skilled in the art may choose other vehicles in order to adapt to specific dermatologic needs.

When antiandrogens are administered systemically, they are preferably administered orally or parenterally. Naturally, topical administration is preferred when the desired site of action is the skin.

Concentration of the active antiandrogen varies in a known manner depending upon the method of administering the pharmaceutical composition. A composition suitable for oral administration may preferably include at least one antiandrogen wherein the total concentration of all such antiandrogens in said pharmaceutical composition is from about 1% to 95% of the composition (by weight), and preferably from about 5% to about 20%. Where a combination of antiandrogens is used, the total dosage of the sum of all antiandrogens should be equal to the dosage range recited above. Blood level of the antiandrogen is a preferred criteria of adequate dosage which takes into account individual variation in absorption and metabolism.

When prepared for parental injection, the antiandrogen is preferably added at a concentration between about 0.1 mg/ml and about 100 mg/ml (preferably about 2.5 mg/ml to about 25 mg/ml).

When systemic activity is desired, it is necessary only that the antiandrogen be administered in a manner and at a dosage sufficient to allow blood serum concentration to obtain desired levels. Serum antiandrogen concentration should typically be maintained between 0.1 and 1000 micrograms per liter, preferably between 50 and 1000 micrograms per liter and most preferably between 50 and 500 micrograms per liter. Adequate serum levels may also be assessed by a patient's response to therapy.

For typical patients, the appropriate dosage of the antiandrogen to achieve desired serum concentration is between 10 and 2000 milligrams of active ingredient per day per 50 kg of body weight when administered orally. When administered by injection, about 2 to 1500 mg per day per 50 kg of body weight is recommended, preferably from 5 to 100.

For topical use lotion, ointment, gel or cream should be thoroughly rubbed into the skin so that no excess is plainly visible, and the skin is preferably not washed in that region for at least 30 minutes. The amount applied should provide at least 0.02 milligrams of antiandrogen per square centimeter (preferably from 0.1 to 1 mg/cm$^2$) per application. It is desirable to apply the topical composition to the effected region from 1 to 6 times daily, e.g. 3 times daily at approximately regular intervals.

In some embodiments of the invention, the antiandrogen of the invention is used in combination with another active ingredient as part of a combination therapy. For example, the novel antiandrogen may be utilized together with a separate 5α-reductase inhibitor, a type 5 or type 3 17β-hydroxysteroid dehydrogenase inhibitor, or a Prostate Short-Chain Dehydrogenase Reductase 1 inhibitor which may be incorporated into the same pharmaceutical composition as is the antiandrogen, or which may be separately administered. Combination therapy could thus include treatment with one or more compounds which inhibit the production of dihydrotestosterone or its precursors. In some preferred embodiments of the invention, the topical pharmaceutical composition further includes an inhibitor of steroid 5α-reductase activity. One such inhibitor ("Propecia or Proscar") is commercially available form Merck Sharp and Dohme. Another inhibitor "Dutasteride" which inhibits both 5α-reductase co-enzymes was registered by GlaxoSmithKline. Inhibitors of type 5 17β-hydroxysteroid dehydrogenase (more particularly compound EM-1404) are disclosed in the international publication WO 99/46279. EM-1792, one of inhibitors type 13 17β-hydroxysteroid dehydrogenase is described in WO 2005/000011.

When 5alpha-reductase inhibitors are used in combination therapies, in accordance with the invention described herein, oral dosage is preferably between 0.1 mg and 100 mg per day per 50 kg body weight, more preferably between 0.5 mg/day and 10 mg/day, for example 5.0 mg per day of finasteride.

When type 5 17beta-hydroxysteroid dehydrogenase inhibitors are used in combination therapies, in accordance with the invention described herein, oral dosage is preferably between 5 mg and 500 mg per day per 50 kg body weight, more preferably between 10 mg/day and 400 mg/day, for example 300 mg per day of EM-1404.

When 17β-hydroxysteroid dehydrogenease type 5 or type 13 inhibitors are used in combination therapies, in accordance with the invention described herein, oral dosage is preferably between 10 mg and 1000 mg per day per 50 kg body weight, more preferably between 25 mg/day and 1000 mg/day, for example 200 mg per day of EM-1404 or EM-2881.

A patient in need of treatment or reducing the risk of onset of a given disease is one who has either been diagnosed with such disease or one who is susceptible to acquiring such disease. The invention is especially useful for individuals who, due to heredity, environmental factors or other recognized risk factor, are at higher risk than the general population of acquiring the conditions to which the present invention relates.

Except where otherwise stated, the preferred dosage of the active compounds of the invention is identical for both therapeutic and prophylactic purposes. The dosage for each active component discussed herein is the same regardless of the disease being treated (or prevented).

Where two are more different active agents are discussed as part of a combination therapy herein (e.g. an enzyme inhibitor and an antiandrogen), a plurality of different compounds are administered rather than a single compound having multiple activities.

Except where otherwise indicated, the term "compound" and any associated molecular structure may include any possible stereoisomers thereof, in the form of a racemic mixture or in optically active form.

Except where otherwise noted or where apparent from context, dosages herein refer to weight of active compounds unaffected by pharmaceutical excipients, diluents, carriers or other ingredients, although such additional ingredients are desirably included, as shown in the examples herein. Any dosage form (capsule, tablet, injection or the like) commonly used in the pharmaceutical industry is appropriate for use herein, and the terms "excipient", "diluent" or "carrier" include such non-active ingredients as are typically included, together with active ingredients in such dosage forms in the industry.

All of the active ingredients used in any of the combination therapies discussed herein may be formulated in pharmaceutical compositions which also include one or more of the other active ingredients. Alternatively, they may each be administered separately but sufficiently simultaneous in time so that a patient eventually has elevated blood levels or otherwise enjoys the benefits of each of the active ingredients (or strategies) simultaneously. In some preferred embodiments of the invention, for example, one or more active ingredients are to be formulated in a single pharmaceutical composition. In other embodiments of the invention, a kit is provided which includes at least two separate containers wherein the contents of at least one other container with respect to active ingredients contained therein. Two or more different containers are used in the combination therapies of the invention. Combination therapies discussed herein also include use of one active ingredient of the combination in the manufacture of a medicament for the treatment (or prevention) of the disease in question where the treatment or prevention further includes another active ingredient or strategy of the combination. For example, in prostate cancer therapy an LHRH agonist or antagonist or an inhibitor of type 3 17β-hydroxysteroid dehydrogenase can be used.

Preferred Compounds

Set forth in the tables below are lists of preferred compounds and their properties and efficacy. The tables I and II only include in vitro determination of androgenic/antiandrogenic activity on mouse mammary carcinoma Shionogi cells and determination of the binding to Human Androgen Receptors in transfected cells and in vivo data determination of antiandrogenic activity on rats. Detailed explanations of how the data were collected and reported follow the tables.

TABLE 1

| | | IN VITRO | |
| --- | --- | --- | --- |
| | | Shionogi Anti-androgenic Activity $IC_{50}$ (nM) | Human Androgen Receptor Binding (%) RBA R1881 = 100 |
| Name 1 | Structure 2 | 3 | 4 |
| OH-FLU | 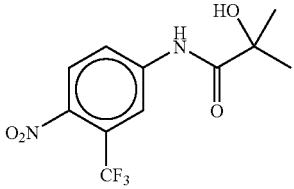 | 54.3 ± 4.8 (n = 39) | 0.29 0.1 |
| FLU | 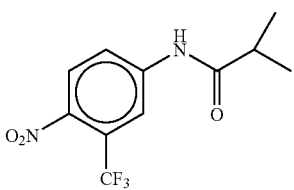 | | |

TABLE 1-continued
| | | | |
|---|---|---|---|
| EM-6936 | 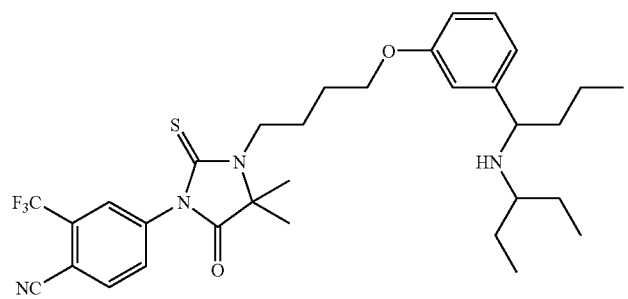 | 157 | 9.7 |
| EM-7065 | 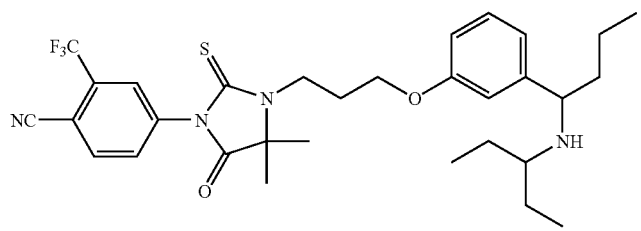 | 84.4 | 30.7 |
| EM-7088 | 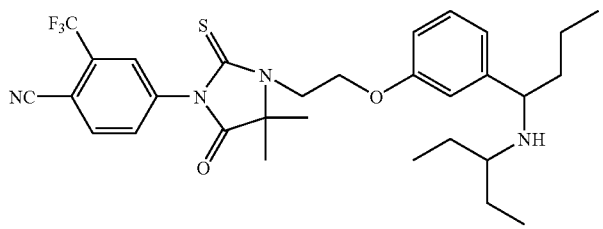 | 101 | 2.0 |
| EM-7096 | 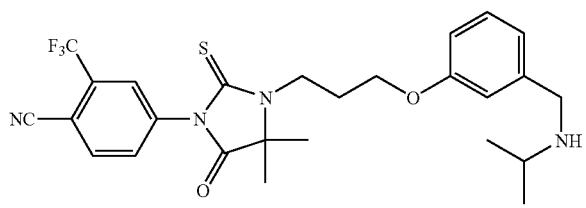 | 27.5 | 3.0 |
| EM-7105 | 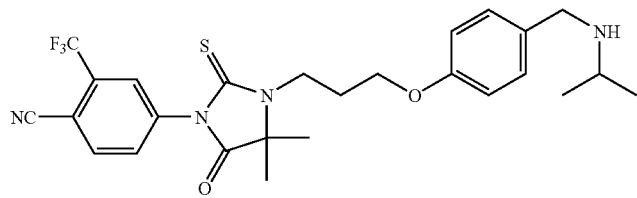 | 11.8 | 11.7 |
| EM-7113 | 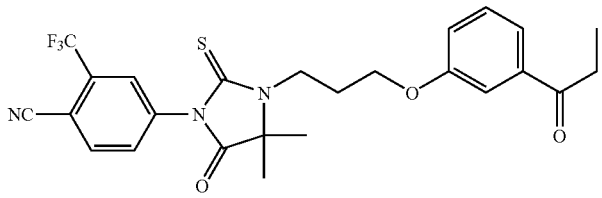 | 69 | 30.5 |

TABLE 1-continued

| Compound | Structure | Col1 | Col2 |
|---|---|---|---|
| EM-7154 | 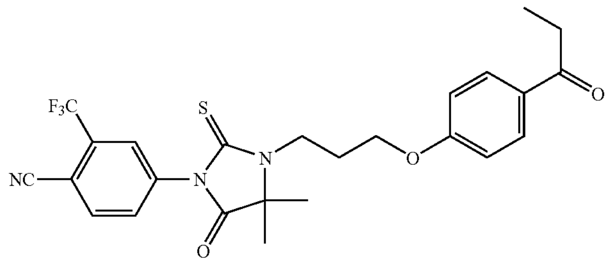 | 20 | 64.7 |
| EM-7168 | 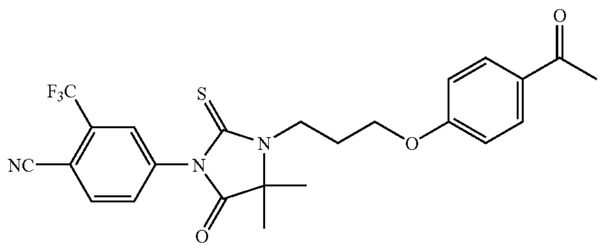 | 13 | 49.3 |
| EM-7144 | 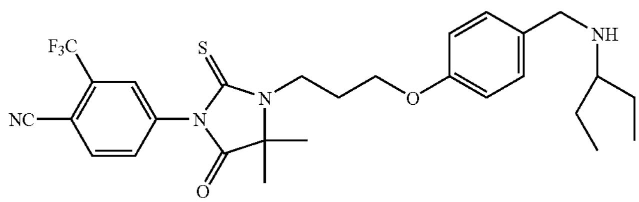 | 22.5 | 14.0 |
| EM-7148 | 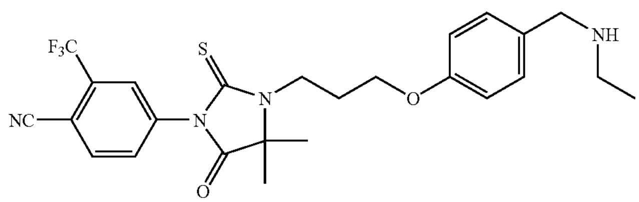 | 6.1 | 12.0 |
| EM-7169 | 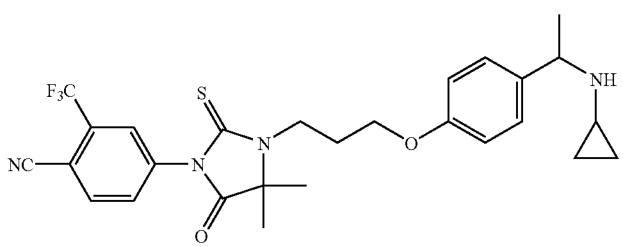 | 11 | 21.7 |
| EM-7192 | 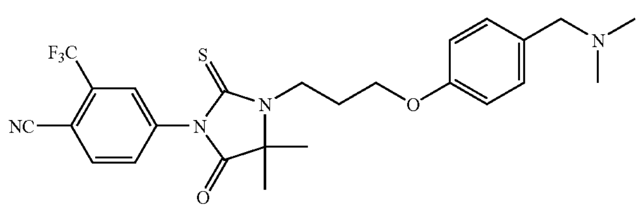 | 11.5 | 15.6 |
| EM-7202 | 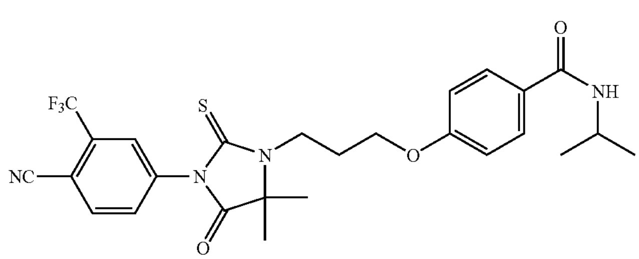 | 36.5 | 37.0 |

TABLE 1-continued

| ID | Structure | Val1 | Val2 |
|---|---|---|---|
| EM-7203 | (structure) | 8.9 | 48.4 |
| EM-7225 | (structure) | 12.5 | 15.3 |
| EM-7227 | (structure) | 10.8 | 18.0 |
| EM-7232 | (structure) | 7.6 | 19.0 |
| EM-7233 | (structure) | 12 | 15.0 |
| EM-7234 | (structure) | 6.2 | 30.4 |
| EM-7242 | (structure) | 9.8 | 18.0 |

TABLE 1-continued

| Compound | Structure | Col1 | Col2 |
|---|---|---|---|
| EM-7243 | 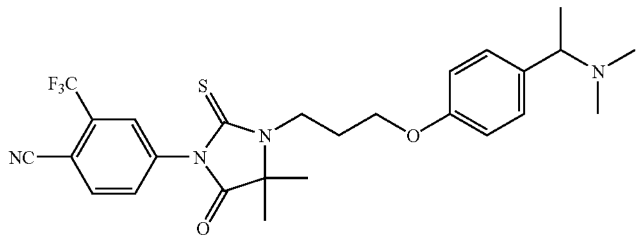 | 14 | 14.0 |
| EM-7248 | 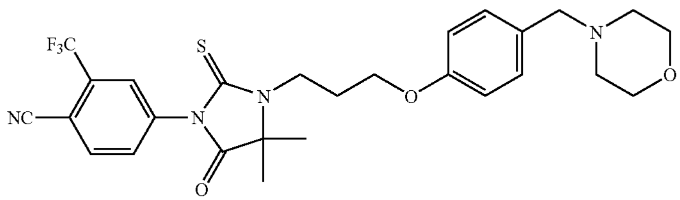 | 19 | 32.4 |
| EM-7260 | 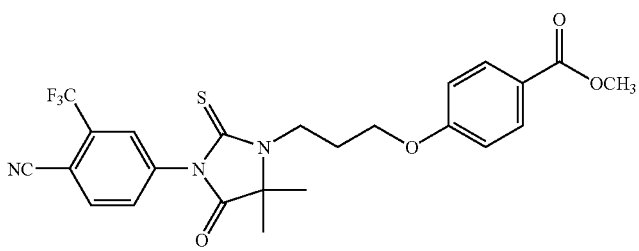 | 17 | 93.3 |
| EM-7297 | 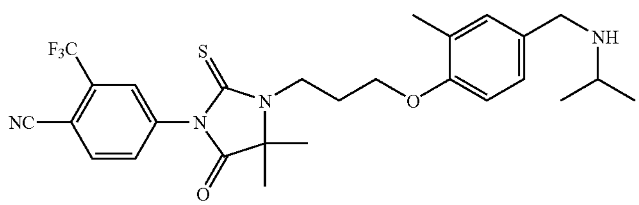 | 6.3 | 59.0 |
| EM-7334 | 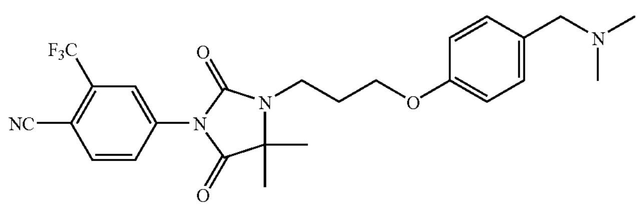 | 118 | 0.5 |
| EM-7365 | 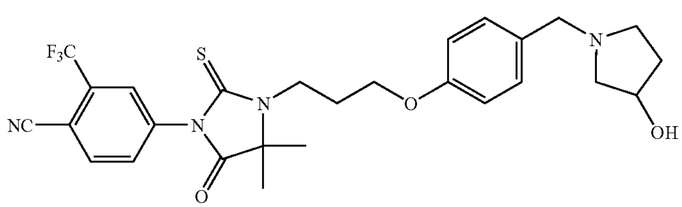 | 6 | 24.0 |
| EM-7366 | 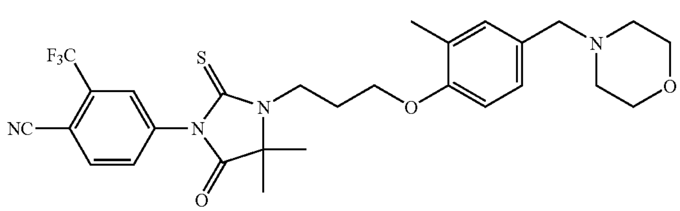 | 22 | 209.0 |

TABLE 1-continued

| Compound | Structure | Col1 | Col2 |
|---|---|---|---|
| EM-7371 | 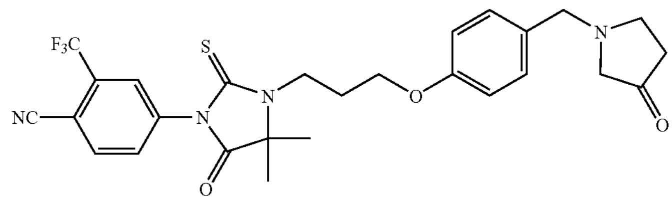 | 15 | 53.0 |
| EM-7612 | 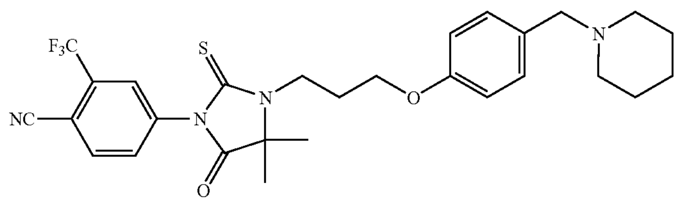 | 44.6 | 0.5 |
| EM-7775 | 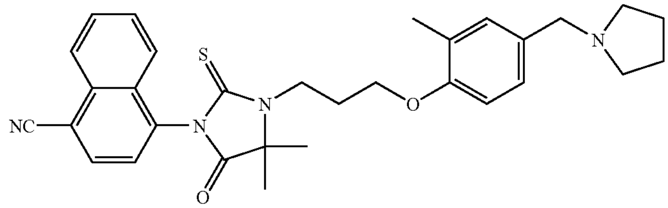 | 60.5 | 13.2 |
| EM-7819 | 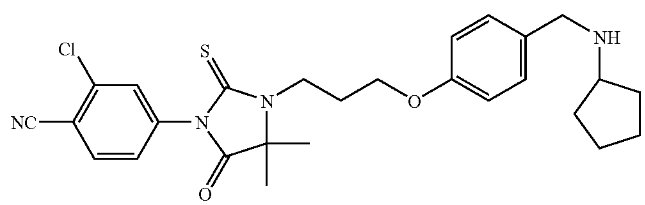 | 8.3 | 12.9 |
| EM-7821 | 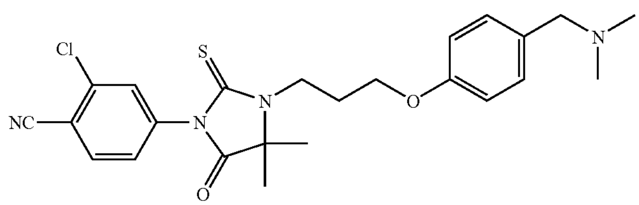 | 5.2 | 6.1 |
| EM-7822 | 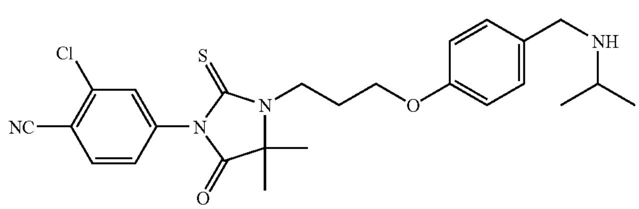 | 5.9 | 4.9 |
| EM-7848 | 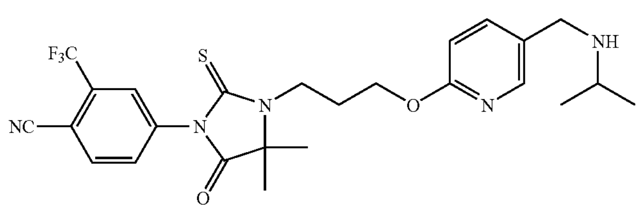 | 11.4 | 0.5 |

TABLE 1-continued

| ID | Structure | Val1 | Val2 |
|---|---|---|---|
| EM-7918 | 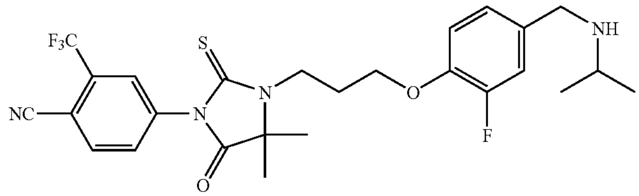 | 6.6 | 16.9 |
| EM-7919 | 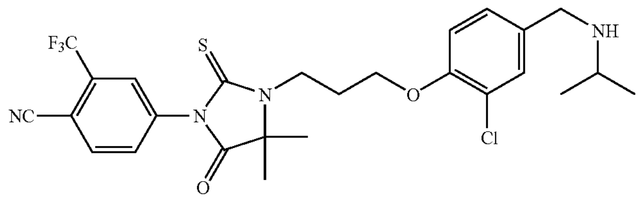 | 6.7 | 29.0 |
| EM-7926 | 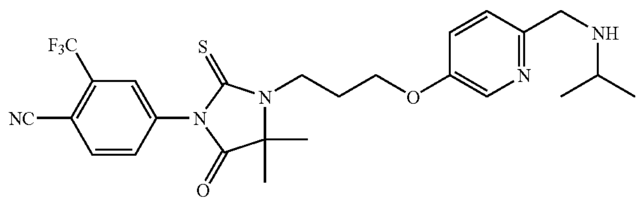 | 7.9 | 1.5 |
| EM-7927 | 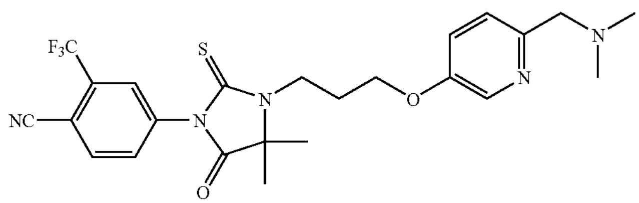 | 6.9 | 2.4 |
| EM-7930 | 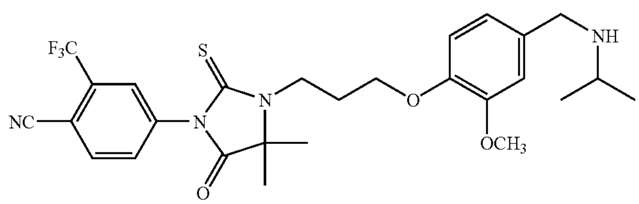 | 9.5 | 0.5 |
| EM-7957 | 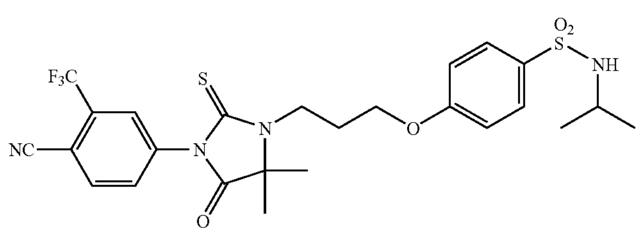 | 17.6 | 5.9 |
| EM-8056 | 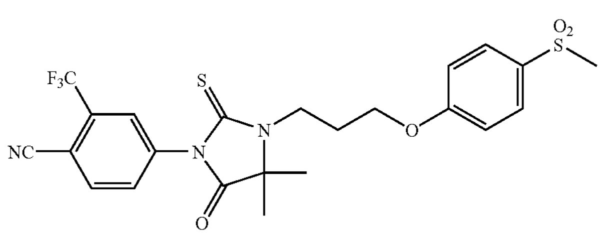 | 12.0 | 6.7 |

TABLE 1-continued
| | | | |
|---|---|---|---|
| EM-8062 | 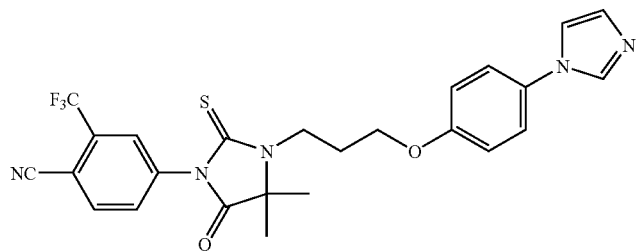 | 6.6 | 15.6 |
| EM-8101 | 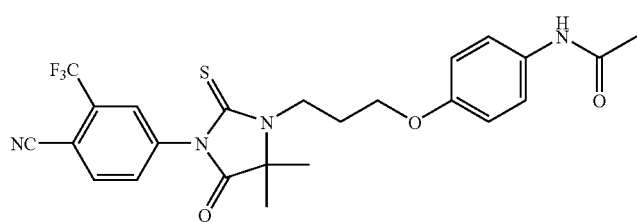 | 18.2 | 12.1 |
| EM-8103 | 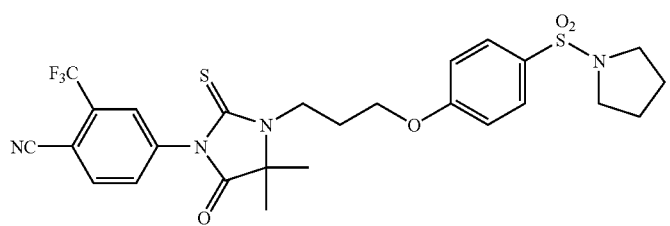 | 41.5 | 29.3 |
| EM-8131 | 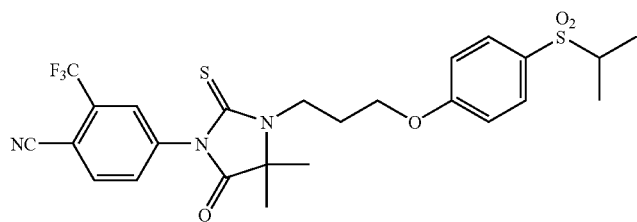 | 9.1 | 9.3 |
| EM-8132 | 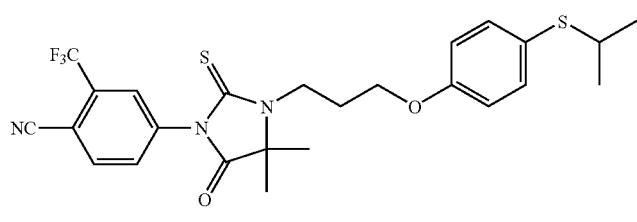 | 24.0 | 1.0 |
| EM-8154 | 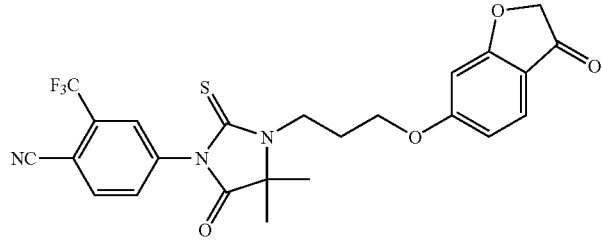 | 17.1 | 72.4 |

TABLE 1-continued

| Compound | Structure | Value 1 | Value 2 |
|---|---|---|---|
| EM-8156 | 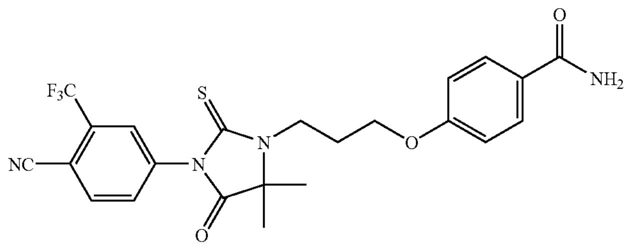 | 7.9 | 17.5 |
| EM-8158 | 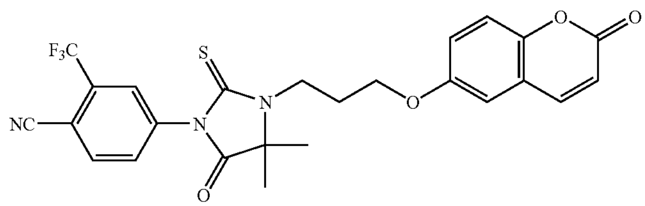 | 3.5 | 88.8 |
| EM-8188 | 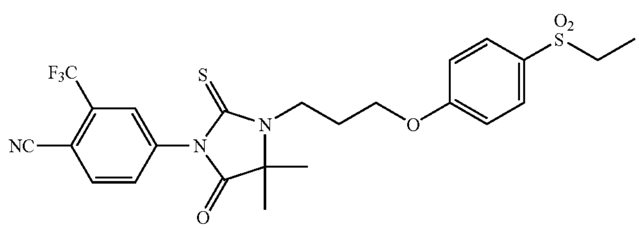 | 13.9 | 15.6 |
| EM-8225 | 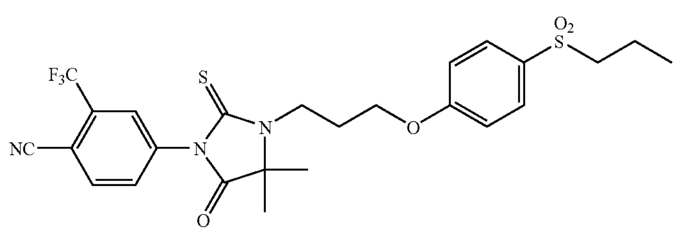 | 22.4 | 25.8 |
| EM-8259 | 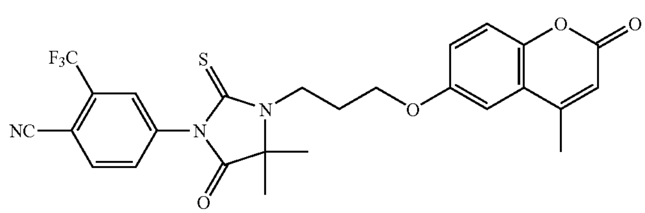 | 13.6 | 39.6 |
| EM-8329 | 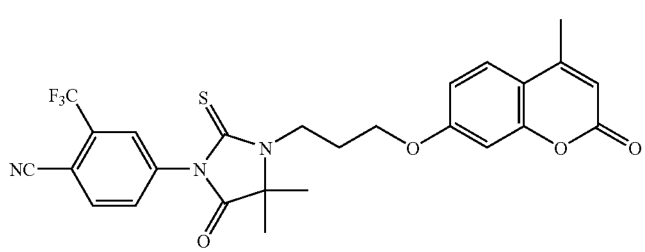 | 9.1 | 170.0 |
| EM-8342 | 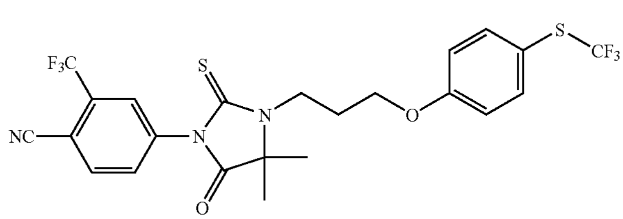 | 66.7 | 0.5 |

TABLE 1-continued

| | | | |
|---|---|---|---|
| EM-8344 | (structure) | 12.6 | 161.6 |
| EM-8360 | (structure) | 7.1 | 18.1 |
| EM-8385 | (structure) | Partial agonist | 50.5 |
| EM-8391 | (structure) | 13.1 | 61.8 |
| EM-8393 | (structure) | 44.5 | 7.7 |
| EM-8406 | (structure) | 73.9 | 2.0 |

TABLE 1-continued
| Name 1 | Structure 2 | | | |
|---|---|---|---|---|
| EM-6926 | 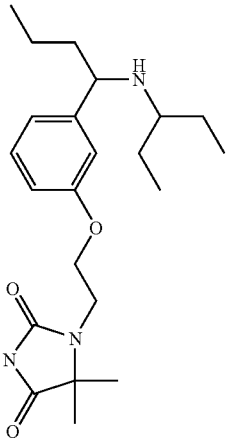 | 200 | | 1 |
| | | IN VIVO Rat Subcutaneous (s.c) or per os (p.o) (+DHT) | | |
|---|---|---|---|---|
| Name 1 | Structure 2 | Prostate % inhibition 5 | SV % inhibition 6 | Lev Ani % inhibition 7 |
| OH-FLU | 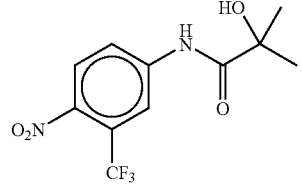 | | | |
| FLU | 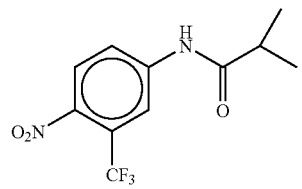 | 38-63 | 80-94 | 41-85 |
| EM-6936 | 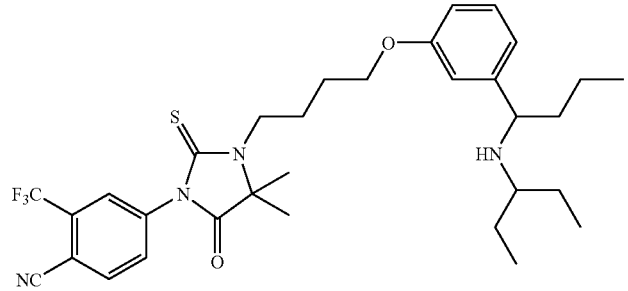 | ND | ND | ND |
| EM-7065 | 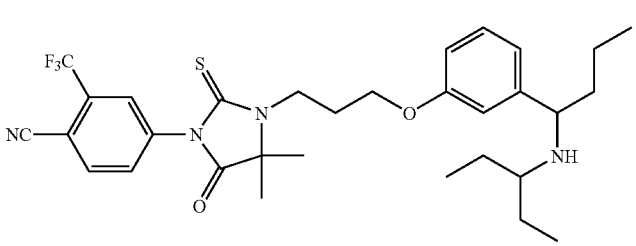 | ND | ND | ND |

TABLE 1-continued

| Compound | Structure | | | |
|---|---|---|---|---|
| EM-7088 | (structure) | ND | ND | ND |
| EM-7096 | (structure) | 42 | 64 | 50 |
| EM-7105 | (structure) | 60 | 81 | 45 |
| EM-7113 | (structure) | 42 | 70 | 58 |
| EM-7154 | (structure) | 8 | 31 | 6 |
| EM-7168 | (structure) | 14 | 54 | 0 |
| EM-7144 | (structure) | 45 | 61 | 41 |

TABLE 1-continued

| Compound | Structure | | | |
|---|---|---|---|---|
| EM-7148 | (structure) | 58 | 85 | 75 |
| EM-7169 | (structure) | 45 | 72 | 31 |
| EM-7192 | (structure) | 53 | 75 | 0 |
| EM-7202 | (structure) | 26 | 63 | 0 |
| EM-7203 | (structure) | 37 | 66 | 4 |
| EM-7225 | (structure) | 52 | 71 | 14 |
| EM-7227 | (structure) | 35 | 77 | 1 |

TABLE 1-continued

| ID | Structure | | | |
|---|---|---|---|---|
| EM-7232 | (structure) | 45 | 84 | 70 |
| EM-7233 | (structure) | 54 | 82 | 70 |
| EM-7234 | (structure) | 50 | 82 | 75 |
| EM-7242 | (structure) | 41 | 72 | 55 |
| EM-7243 | (structure) | 34 | 72 | 73 |
| EM-7248 | (structure) | 37 | 62 | 44 |
| EM-7260 | (structure) | 25 | 47 | 0 |

TABLE 1-continued

| Compound | Structure | | | |
|---|---|---|---|---|
| EM-7297 | 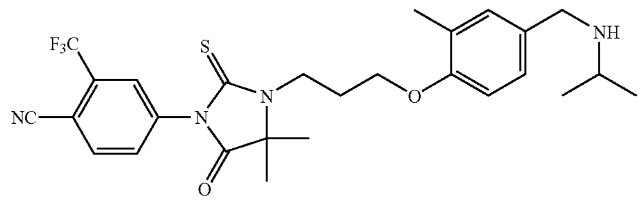 | 29 | 37 | 31 |
| EM-7334 | 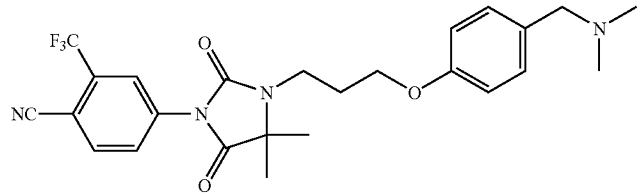 | 14 | 26 | |
| EM-7365 | 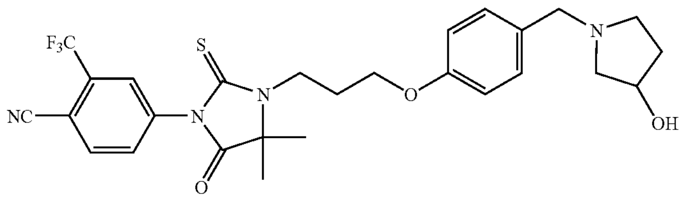 | 22 | 43 | 19 |
| EM-7366 | 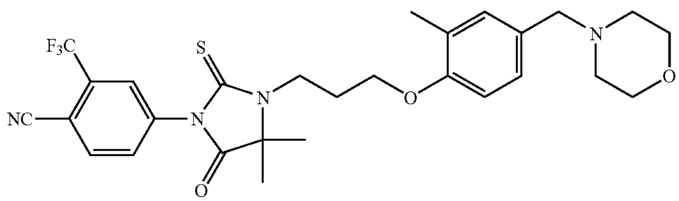 | 26 | 70 | 16 |
| EM-7371 | 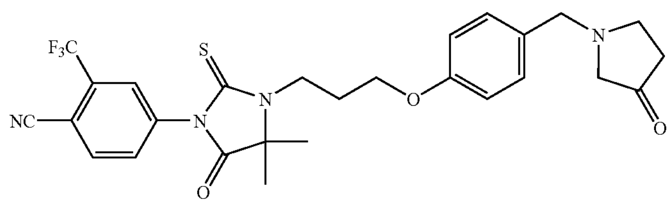 | 16 | 48 | 21 |
| EM-7612 | 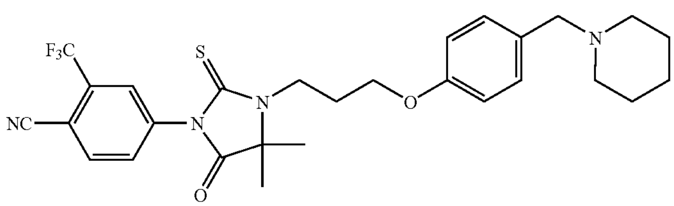 | ND | ND | ND |
| EM-7775 | 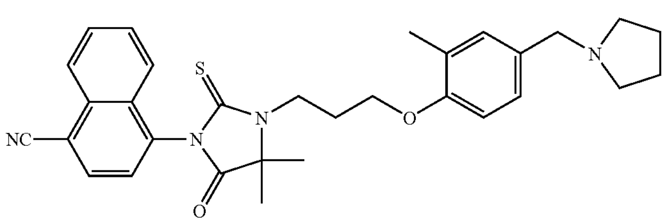 | 0 | 25 | 10 |

TABLE 1-continued
| | | | | | |
|---|---|---|---|---|---|
| EM-7819 | 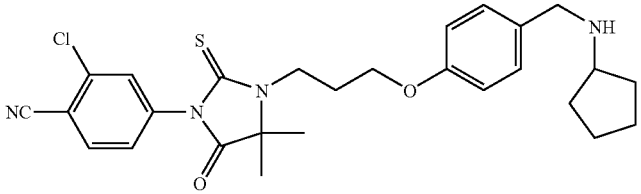 | 54 | 80 | 44 | |
| EM-7821 | 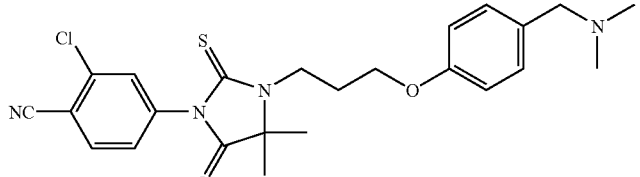 | 50 | 75 | 32 | |
| EM-7822 | 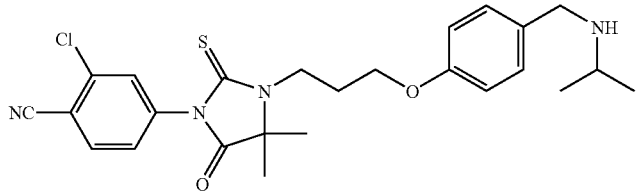 | 53 | 82 | 60 | |
| EM-7848 | 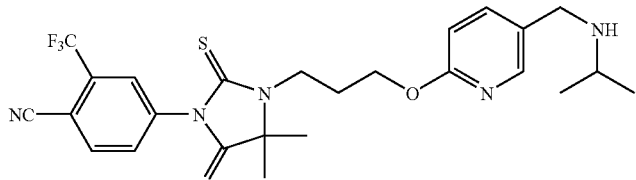 | 51 | 86 | 68 | |
| EM-7918 | 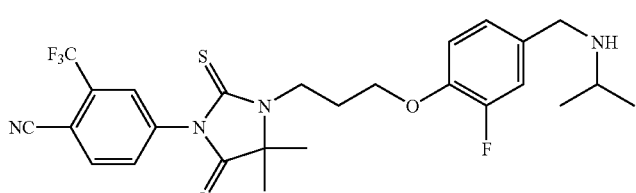 | 44 | 64 | 53 | |
| EM-7919 | 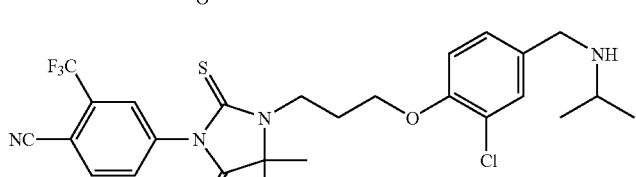 | 28 | 53 | 9 | |
| EM-7926 | 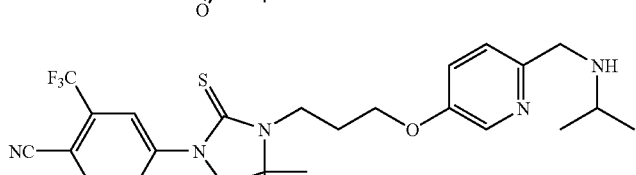 | 44 | 72 | 14 | |
| EM-7927 | 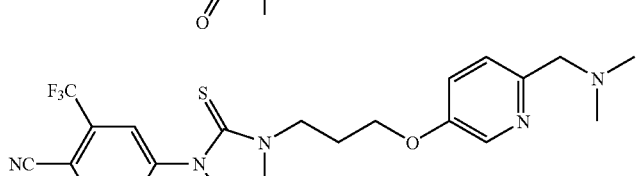 | 32 | 55 | 61 | |

TABLE 1-continued

| Compound | Structure | | | |
|---|---|---|---|---|
| EM-7930 | (structure) | 47 | 71 | 41 |
| EM-7957 | (structure) | 44 | 72 | 75 |
| EM-8056 | (structure) | 49 p.o | 91 | 80 |
| EM-8062 | (structure) | 37 p.o | 79 | 63 |
| EM-8101 | (structure) | 8 p.o | 41 | 43 |
| EM-8103 | (structure) | 18 p.o | 37 | 16 |
| EM-8131 | (structure) | 47 p.o | 84 | 47 |

TABLE 1-continued

| Compound | Structure | | | |
|---|---|---|---|---|
| EM-8132 | 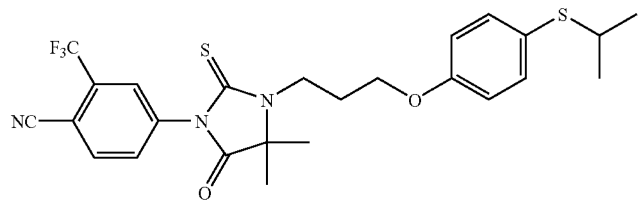 | 47 p.o | 86 | 67 |
| EM-8154 | 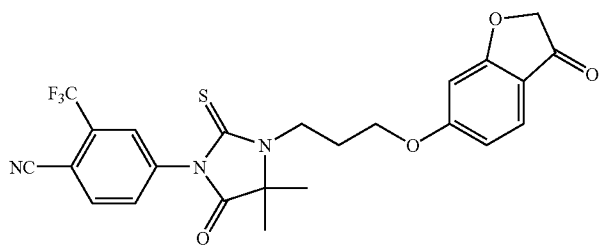 | 11 p.o | 42 | 41 |
| EM-8156 | 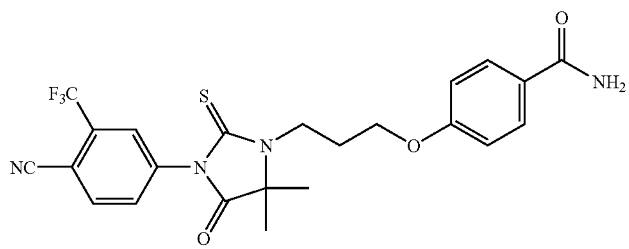 | 32 p.o | 65 | 47 |
| EM-8158 | 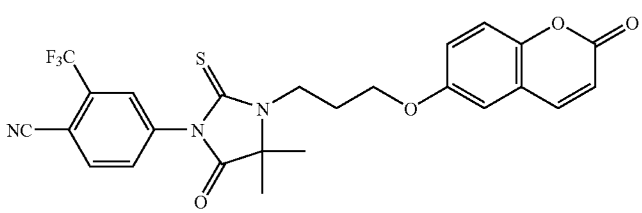 | 38 p.o | 70 | 32 |
| EM-8188 | 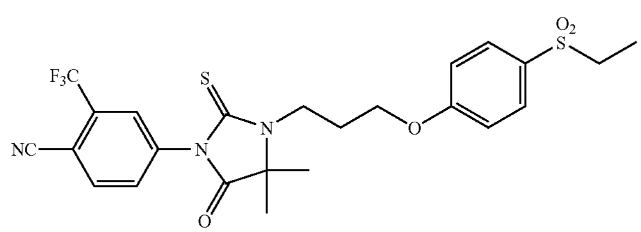 | 45 p.o | 85 | 68 |
| EM-8225 | 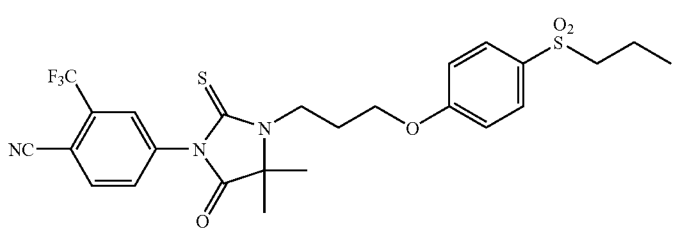 | 45 p.o | 79 | 53 |
| EM-8259 | 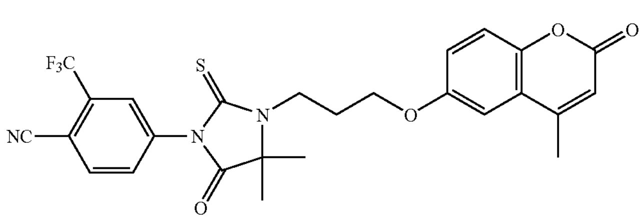 | 31 p.o | 53 | 53 |

TABLE 1-continued

| Code | Structure | Dose | Val1 | Val2 |
|---|---|---|---|---|
| EM-8329 | 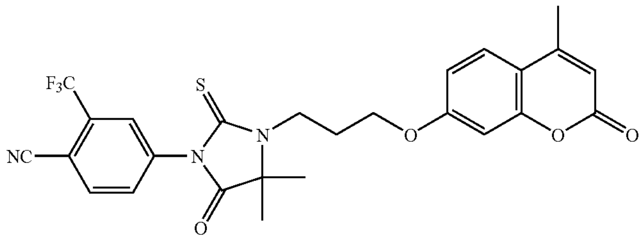 | 42 p.o | 58 | 17 |
| EM-8342 | 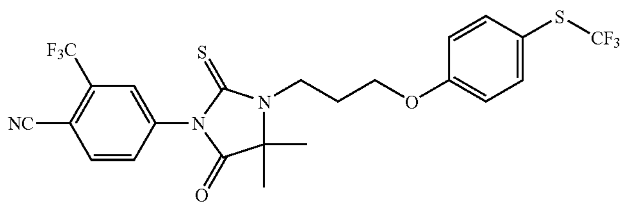 | 43 p.o | 79 | 53 |
| EM-8344 | 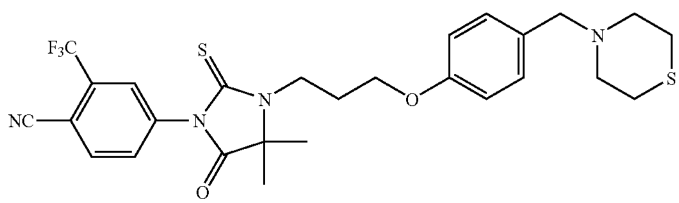 | 50 p.o | 77 | 51 |
| EM-8360 | 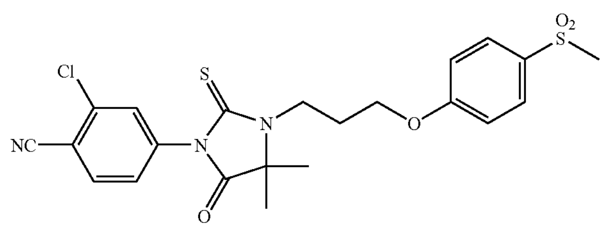 | 56 p.o | 88 | 82 |
| EM-8385 | 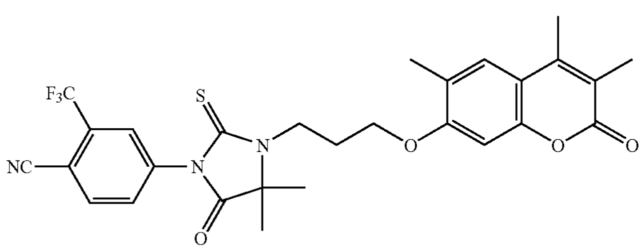 | 17 p.o | 41 | 20 |
| EM-8391 | 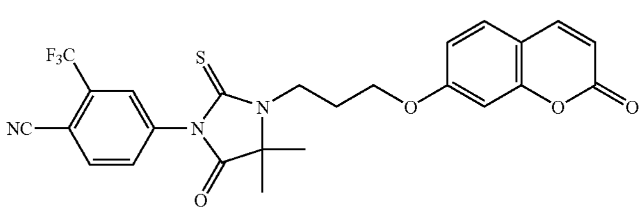 | ND | ND | ND |
| EM-8393 | 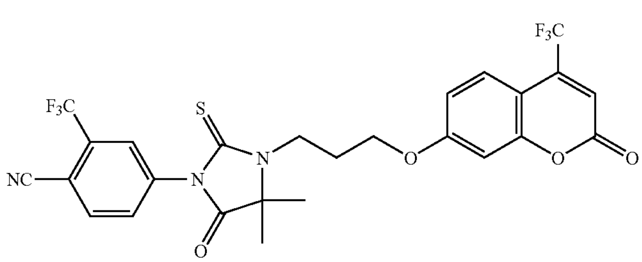 | 3 p.o | 60 | 35 |

TABLE 1-continued

| Name | Structure | | | |
|---|---|---|---|---|
| EM-8406 | (structure) | ND | ND | ND |
| EM-6926 | (structure) | ND | ND | ND |

TABLE 2

| | | IN VITRO | |
|---|---|---|---|
| Name 1 | Structure 2 | Shionogi Anti-androgenic Activity IC$_{50}$ (nM) 3 | Human Androgen Receptor Binding (%) RBA R1881 = 100 4 |
| OH-FLU | | 54.3 (n = 39) | |
| FLU | | | |
| EM-7321 | (structure) | 111.0 | 1.0 |
| EM-7332 | (structure) | 25.0 | 1.8 |

TABLE 2-continued

| Compound | Structure | | |
|---|---|---|---|
| EM-7363 | (structure) | 12.1 | 5.7 |
| EM-7421 | (structure) | 15.5 | 5.7 |
| EM-7429 | (structure) | 24.0 | 1.6 |
| EM-7430 | (structure) | 22.4 | 2.3 |
| EM-7438 | (structure) | 13.2 | 3.9 |
| EM-7439 | (structure) | 13.5 | 2.2 |

TABLE 2-continued

| ID | Structure | Col1 | Col2 |
|---|---|---|---|
| EM-7440 | (3-Cl, 4-CN-phenyl)-piperidine-4-OH-CH2CH2-O-(4-(morpholinomethyl)phenyl) | 18.2 | 2.4 |
| EM-7461 | (3-CF3, 4-CN-phenyl)-piperidine-4-OH-CH2CH2-O-(4-(2,6-dimethylpiperidin-1-ylcarbonyl)phenyl) | 13.2 | 2 |
| OH-FLU | | 54.3 (n = 39) | |
| FLU | | | |
| EM-7479 | (3-CF3, 4-CN-phenyl)-piperidine-4-OH-CH2CH2CH2-O-(4-(morpholinocarbonyl)phenyl) | 32.6 | 0.6 |
| EM-7491 | (3-CF3, 4-CN-phenyl)-piperidine-4-OH-CH2CH2-O-(4-(isopropylaminomethyl)phenyl) | 21.7 | 0.9 |
| EM-7492 | (3-CF3, 4-CN-phenyl)-piperidine-4-OH-CH2CH2-O-(2-F, 4-(morpholinomethyl)phenyl) | 15.4 | 1.6 |
| EM-7507 | (3-CF3, 4-CN-phenyl)-piperidine-4-OH-CH2CH2-O-(2,6-dimethyl-4-(morpholinomethyl)phenyl) | 132.0 | 0.3 |

TABLE 2-continued

| Compound | Structure | Value 1 | Value 2 |
|---|---|---|---|
| EM-7534 | 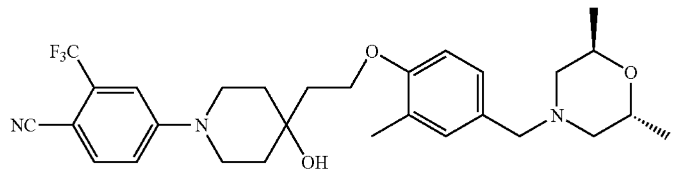 | 32.3 | 2.5 |
| EM-7535 | 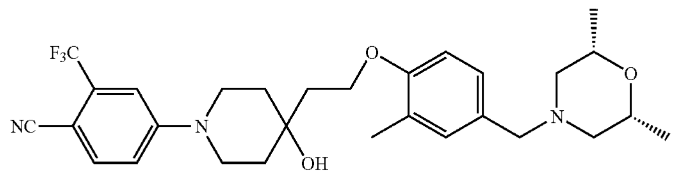 | 33.2 | 1.1 |
| EM-7564 | 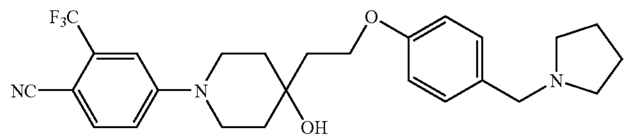 | 27.3 | 2.2 |
| EM-7565 | 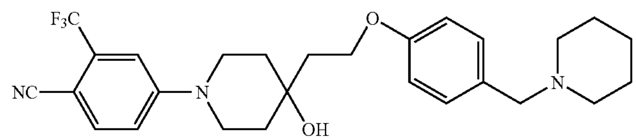 | 85.6 | 0.5 |
| EM-7575 | 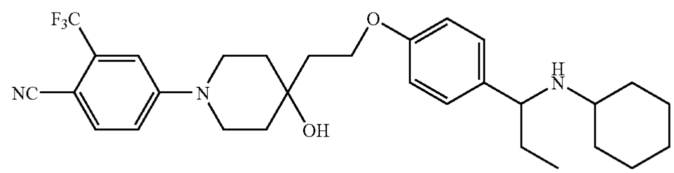 | 58.6 | 14.4 |
| EM-7627 | 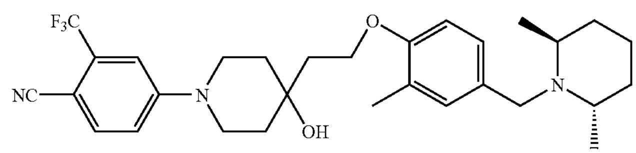 | 54.0 | 2.7 |
| EM-7657 | 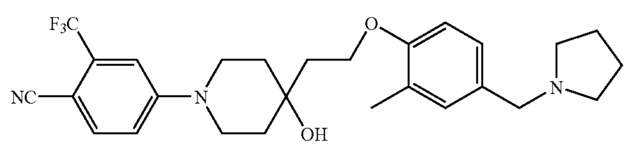 | 22.0 | 3.0 |
| EM-7676 | 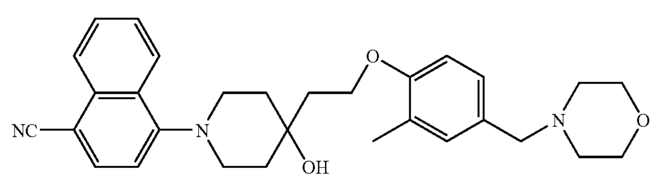 | 147.0 | 0.3 |
| OH-FLU | | 54.3 (n = 39) | |
| FLU | | | |
| EM-7678 | 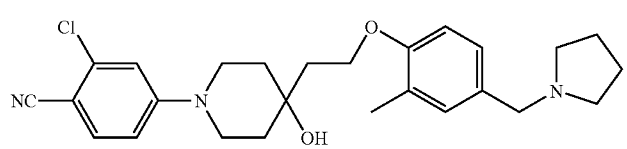 | 13.8 | 3.5 |

TABLE 2-continued
| | | | |
|---|---|---|---|
| EM-7735 | 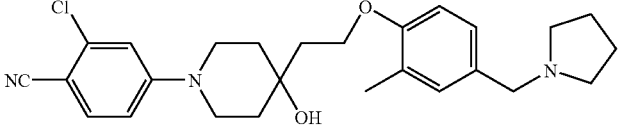 | 7.9 | 9.6 |
| EM-7738 | 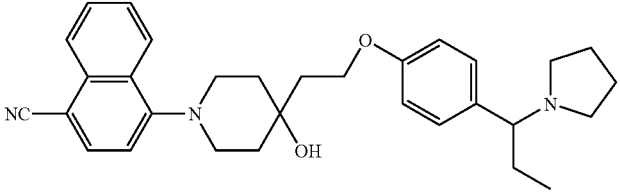 | 18.3 | 10.5 |
| EM-7791 | 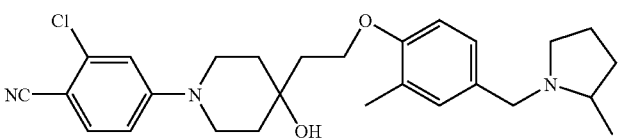 | 20.5 | 1.0 |
| EM-7809 | 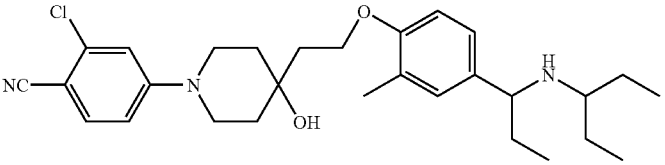 | 7.3 | 13.4 |
| EM-7892 | 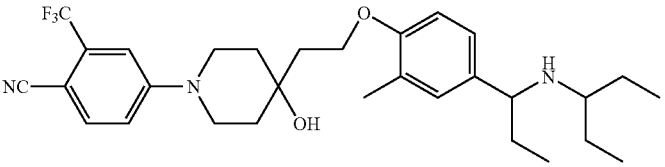 | 3.1 | 12.2 |
| EM-7893 | 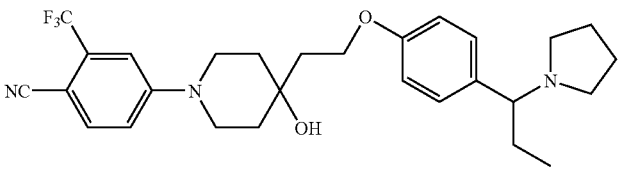 | 5.1 | 10.3 |
| EM-8003 | 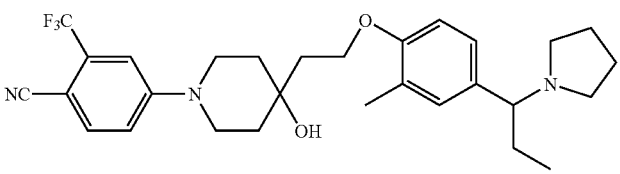 | 22.3 | 6.4 |
| EM-8006 | 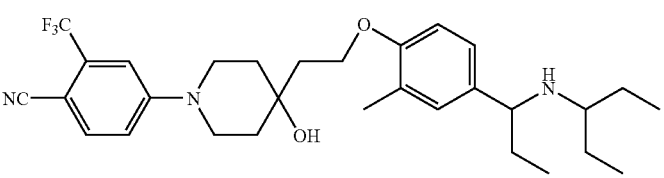 | 30.8 | 8.1 |
| EM-8026 | 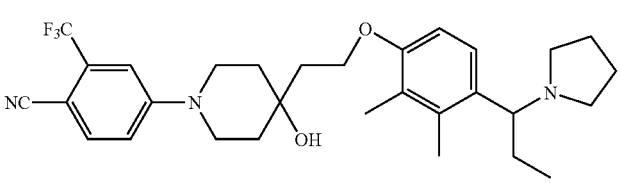 | 19.0 | 1.0 |

TABLE 2-continued
| EM-8058 |  | 56.5 | 1.5 |
| EM-8059 | 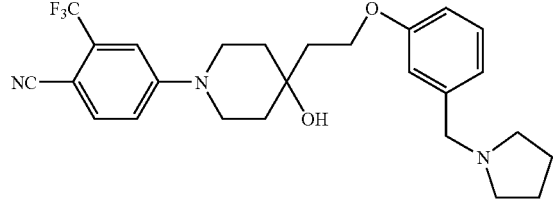 | 68.9 | 1.0 |
| EM-8096 | 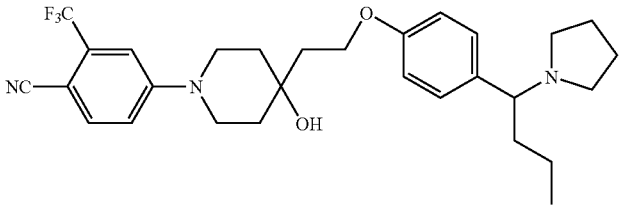 | 19.6 | 6.9 |
| EM-8130 | 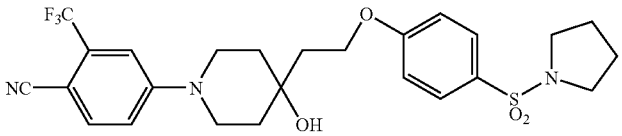 | 28.3 | 4.5 |
| EM-8157 | 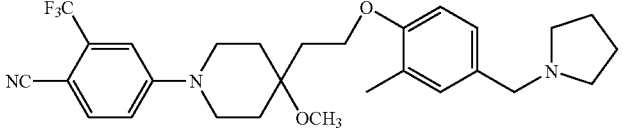 | 54.3 | <1.0 |
| EM-8159 | 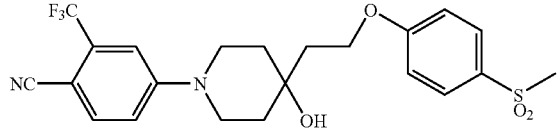 | 33.4 | <1.0 |
| EM-8228 | 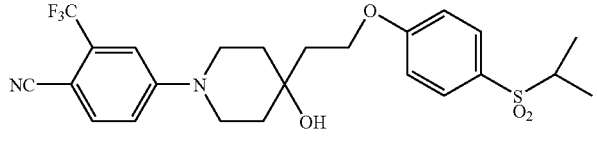 | 45.1 | <1.0 |
| EM-8229 | 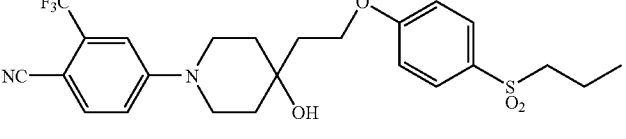 | 49.8 | <1.0 |
| EM-8230 | 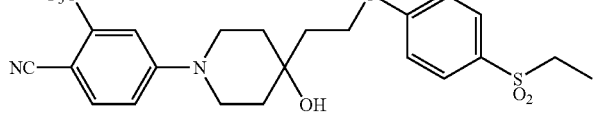 | 75.9 | <1.0 |

TABLE 2-continued

| Name | Structure | | |
|---|---|---|---|
| EM-8284 | (F₃C, NC-phenyl-piperidine(OH)-CH₂CH₂-O-coumarin) | 12.8 | <1.0 |
| EM-8285 | (F₃C, NC-phenyl-piperidine(OH)-CH₂CH₂-O-4-methylcoumarin) | 18.3 | <1.0 |
| EM-7727 | (F₃C, NC-phenyl-piperazine-CH₂CH₂-O-CH₂-phenyl-CH(Et)-NH-cyclohexyl) | 70.4 | <1.0 |
| EM-7792 | (F₃C, NC-phenyl-piperazine-CH₂CH₂-O-CH₂-phenyl-CH(Et)-NH-CH(Et)₂) | 82.9 | <1.0 |

| | | IN VIVO Rat Subcutaneous (s.c.) or per os (p.o) (+DHT) | | |
|---|---|---|---|---|
| Name 1 | Structure 2 | Prostate % inhibition 5 | SV % inhibition 6 | Lev Ani % inhibition 7 |
| OH-FLU FLU | | | | |
| | | 38-63 | 80-94 | |
| EM-7321 | (F₃C, NC-phenyl-piperidine(OH)-CH₂CH₂-O-phenyl-CH₂-NH-cyclohexyl) | ND | ND | ND |
| EM-7332 | (F₃C, NC-phenyl-piperidine(OH)-CH₂CH₂-O-phenyl-CH₂-NH-cyclohexyl) | ND | ND | ND |

TABLE 2-continued

| | | | | |
|---|---|---|---|---|
| EM-7363 | (structure) | ND | ND | ND |
| EM-7421 | (structure) | ND | ND | ND |
| EM-7429 | (structure) | ND | ND | ND |
| EM-7430 | (structure) | ND | ND | ND |
| EM-7438 | (structure) | ND | ND | ND |
| EM-7439 | (structure) | ND | ND | ND |

TABLE 2-continued

| Compound | Structure | | | |
|---|---|---|---|---|
| EM-7440 | (structure) | ND | ND | ND |
| EM-7461 | (structure) | ND | ND | ND |
| OH-FLU FLU | | 38-63 | 80-94 | |
| EM-7479 | (structure) | ND | ND | ND |
| EM-7491 | (structure) | ND | ND | ND |
| EM-7492 | (structure) | ND | ND | ND |
| EM-7507 | (structure) | ND | ND | ND |
| EM-7534 | (structure) | ND | ND | ND |

TABLE 2-continued

| Compound | Structure | | | |
|---|---|---|---|---|
| EM-7535 | [structure] | ND | ND | ND |
| EM-7564 | [structure] | ND | ND | ND |
| EM-7565 | [structure] | ND | ND | ND |
| EM-7575 | [structure] | ND | ND | ND |
| EM-7627 | [structure] | ND | ND | ND |
| EM-7657 | [structure] | 24 | 41 | 55 |
| EM-7676 | [structure] | 0 | 3 | 0 |
| OH-FLU | | | | |
| FLU | | 38-63 | 80-94 | |
| EM-7678 | [structure] | 7 | 10 | 9 |
| EM-7735 | [structure] | 0 | 23 | 29 |

TABLE 2-continued
| | | | | |
|---|---|---|---|---|
| EM-7738 | 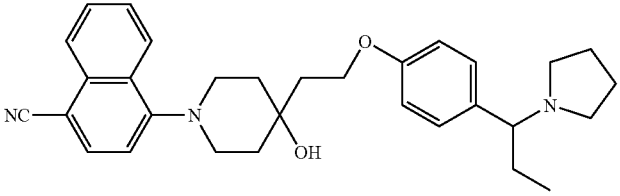 | 0 | 16 | 10 |
| EM-7791 | 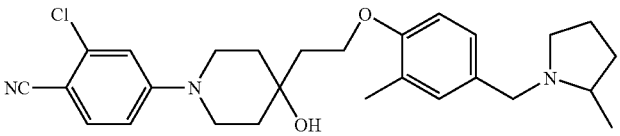 | 0 | 29 | 14 |
| EM-7809 | 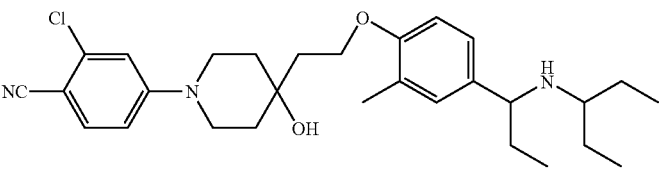 | ND | ND | ND |
| EM-7892 | 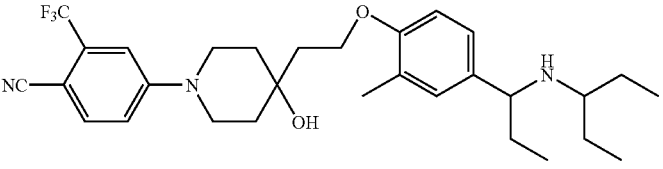 | 7 | 14 | 24 |
| EM-7893 | 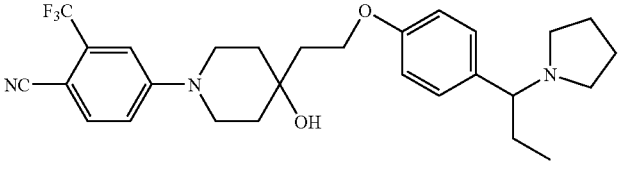 | 6 | 38 | 26 |
| EM-8003 | 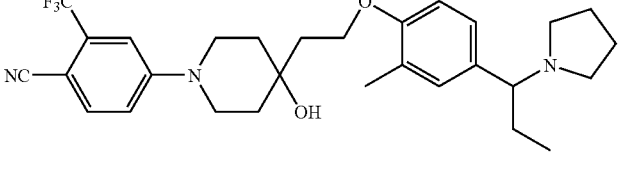 | 11 | 35 | 44 |
| EM-8006 | 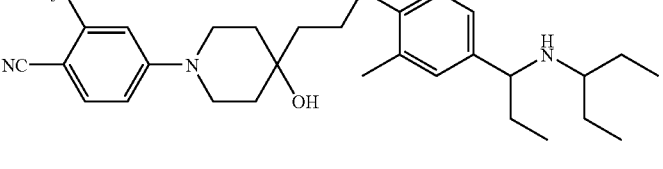 | 14 | 32 | 40 |
| EM-8026 | 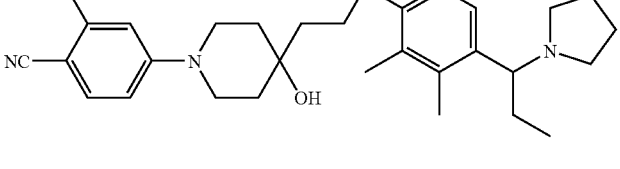 | ND | ND | ND |
| EM-8058 | 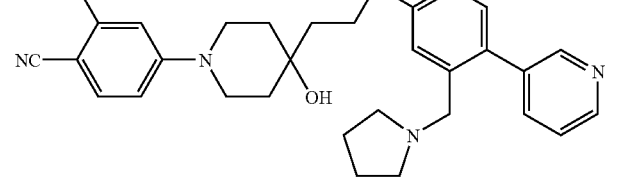 | 0 | 2 | 6 |

TABLE 2-continued

| | | | | |
|---|---|---|---|---|
| EM-8059 | | 1 | 21 | 0 |
| EM-8096 | | 8 | 55 | 50 |
| EM-8130 | | 15 | 20 | 8 |
| EM-8157 | | 25 | 56 | 28 |
| EM-8159 | | 24 | 51 | 23 |
| EM-8228 | | 32 | 0 | 55 |
| EM-8229 | | 3 | 19 | 16 |

TABLE 2-continued

| | | | | | |
|---|---|---|---|---|---|
| EM-8230 | 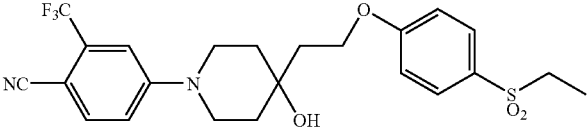 | | 0 | 23 | 35 |
| EM-8284 | 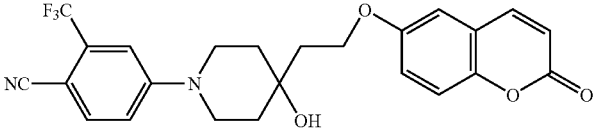 | | 0 | 0 | 21 |
| EM-8285 | 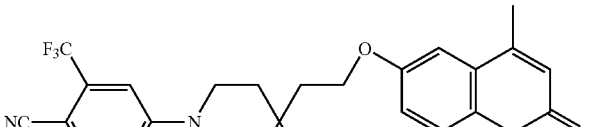 | | 0 | 0 | 0 |
| EM-7727 | 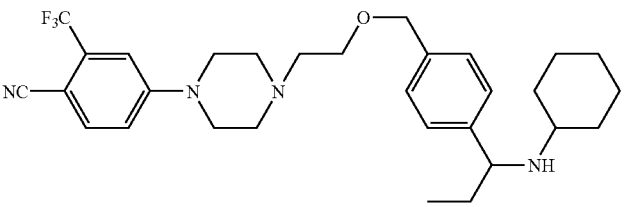 | | 0 | 8 | 0 |
| EM-7792 | 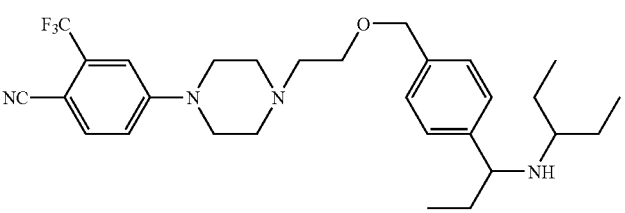 | | 21 | 0 | 7 |

Legend of the Tables 1 and 2:

In Column 1, the laboratory name of the antiandrogens is reported.

In Column 2, the molecular structure of the antiandrogens is reported.

Column 3 represents the dose (expressed in nM) that inhibits by 50% ($IC_{50}$) the DHT-stimulated Shionogi mouse mammary carcinoma cell number. Lower values are preferable.

Column 4 represents the Relative Binding Affinity (RBA) of the antiandrogen expressed as percentage (%) on Human Androgen Receptor in transfected cells relative to R1881 as calculated by the formula:

% RBA=100×$IC_{50}$R1881/$IC_{50}$ (compound)

Higher values are preferable

Column 5 represents the % of antiandrogenic efficacy in rat prostate, expressed in percentage of inhibition:

Where the percentage of inhibition (% inhib) is calculated by the following formula:

% Inhib=100−[W(compound)−W(control)/W(DHT)−W(control)]×100.

W is the weight of the prostate.

Higher values are preferable.

Column 6 represents the % of antiandrogenic efficacy in rat seminal vesicle, expressed in percentage of inhibition:

Where the percentage of inhibition (% inhib) is calculated by the following formula:

% Inhib=100−[W(compound)−W(control)/W(DHT)−W(control)]×100.

W is the weight of the seminal vesicle.

Higher values are preferable.

Column 7 represents the % of antiandrogenic efficacy in rat levator ani muscle, expressed in percentage of inhibition:

Where the percentage of inhibition (% inhib) is calculated by the following formula:

% Inhib=100−[W(compound)−W(control)/W(DHT)−W(control)]×100.

W is the weight of the seminal vesicle.

Higher values are preferable.

TABLE 3

| Structure and Name | IN VITRO | |
|---|---|---|
| | Shionogi Anti-androgenic Activity IC$_{50}$ (nM) | Human Androgen Receptor Binding (%) RBA R1881 = 100 |
| 1 | 2 | 3 |
| Testo | 23-107 | 10 |
| EM-7198 | 10.0 | 44 |
| EM-7298 | 8.2 | 61 |
| EM-8255 | Partial agonist | 76 |
| EM-8260 | Partial agonist | 17 |
| EM-8261 | Partial agonist | 32 |

TABLE 3-continued
| Structure and Name | | | | | | | |
|---|---|---|---|---|---|---|---|
| 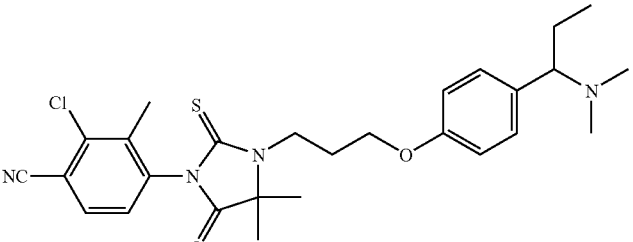 EM-8345 | Partial agonist | | | 68 | | | |
| 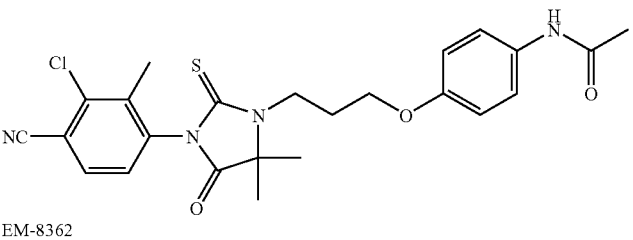 EM-8362 | Partial agonist | | | 66 | | | |
| 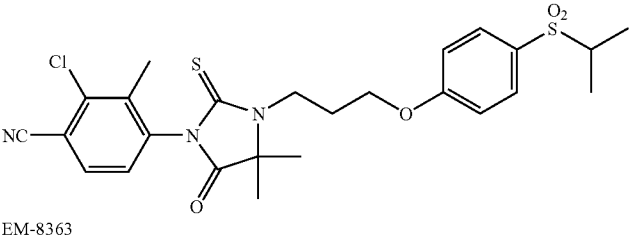 EM-8363 | Partial agonist | | | 52 | | | |
| 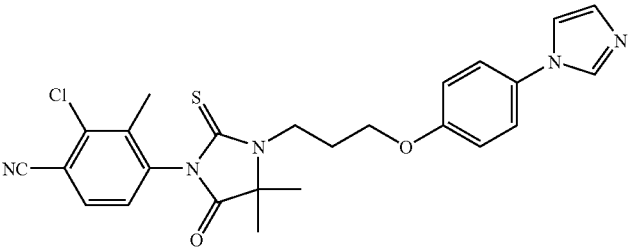 EM-8346 | Partial agonist | | | 125 | | | |
| | IN VIRO Rat | | | | | |
|---|---|---|---|---|---|---|
| | Subcutaneous (s.c.) or per os (p.o) (+DHT) % Inhibition | | | Subcutaneous (s.c.) or per os (p.o) % Stimulation | | |
| Structure and Name 1 | Prostate 4 | SV 5 | Lev.Ani 6 | Prostate 7 | SV 8 | Lev.Ani 9 |
| Testo | | | | 99 | 115 | 171 |
| 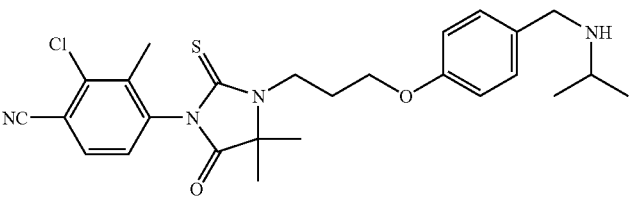 EM-7198 | 15 s.c | | | 65 s.c | 106 | 182 |

TABLE 3-continued
| Structure | | | | | |
|---|---|---|---|---|---|
|  EM-7298 | 36 s.c | 14 | 33 s.c | 29 | 103 |
| 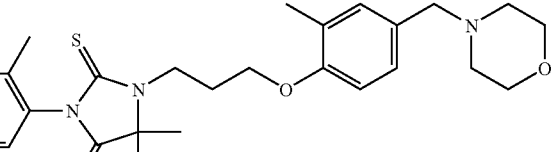 EM-8255 | 17 s.c | | 32 s.c | 31 | 80 |
| 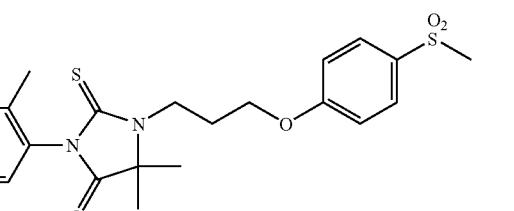 EM-8260 | 40 p.o | 54 | 24 | 27 p.o | 28 | 74 |
| 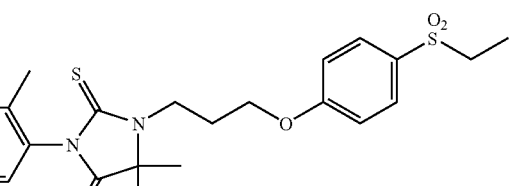 EM-8261 | 38 p.o | 25 | 8 | 41 p.o | 26 | 82 |
| 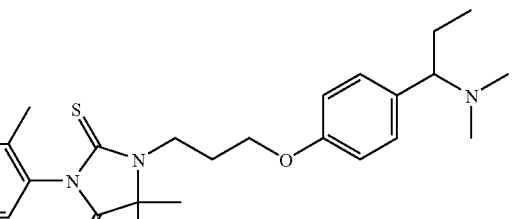 EM-8345 | ND | ND | ND | 42 p.o | 18 | 77 |
| 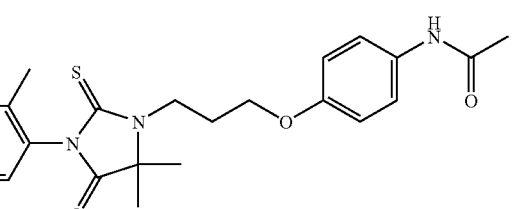 EM-8362 | ND | ND | ND | 33 p.o | 43 | 105 |

TABLE 3-continued

| Structure | | | | | | | | |
|---|---|---|---|---|---|---|---|---|
| EM-8363 | ND | ND | ND | 29 p.o | 24 | 85 | | |
| EM-8346 | ND | ND | ND | 47 p.o | 40 | 128 | | |

Legend of the Table 3:

In Column 1, the molecular structure and the laboratory name of the antiandrogens is reported.

Column 2 represents the dose (expressed in nM) that inhibits by 50% ($IC_{50}$) the DHT-stimulated Shionogi mouse mammary carcinoma cell number. When the compound stimulates Shionogi mouse mammary carcinoma cell the term agonist is reported. Lower values are preferable.

Column 3 represents the Relative Binding Affinity (RBA) of the antiandrogen expressed as percentage (%) on Human Androgen Receptor in transfected cells relative to R1881 as calculated by the formula:

% RBA=100×$IC_{50}$R1881/$IC_{50}$ (compound)

Higher values are preferable.

Column 4 represents the % of antiandrogenic efficacy in rat prostate, expressed in percentage of inhibition:

Where the percentage of inhibition is calculated by the following formula:

% Inhib=100−[$W$(compound)−$W$(control)/$W$(DHT)−
$W$(control)]×100.

W is the weight of the prostate.

Higher values are preferable.

Column 5 represents the % of antiandrogenic efficacy in rat seminal vesicle, expressed in percentage of inhibition:

Where the percentage of inhibition is calculated by the following formula:

% Inhib=100−[$W$(compound)−$W$(control)/$W$(DHT)−
$W$(control)]×100.

W is the weight of the seminal vesicle.

Higher values are preferable.

Column 6 represents the % of antiandrogenic efficacy in rat levator ani muscle, expressed in percentage of inhibition:

Where the percentage of inhibition is calculated by the following formula:

% Inhib=100−[$W$(compound)−$W$(control)/$W$(DHT)−
$W$(control)]×100.

W is the weight of the seminal vesicle.

Lower values are preferable.

Column 7 represents the % of androgenic efficacy in rat prostate, expressed in percentage of stimulation:

Where the percentage of stimulation is calculated by the following formula:

% stimulation=[$W$(compound)−$W$(control)/$W$(DHT)−
$W$(control)]×100.

W is the weight of the prostate.

Lower values are preferable.

Column 8 represents the % of androgenic efficacy in rat seminal vesicle, expressed in percentage of stimulation:

Where the percentage of stimulation is calculated by the following formula:

% stimulation=[$W$(compound)−$W$(control)/$W$(DHT)−
$W$(control)]×100.

W is the weight of the seminal vesicle.

Lower values are preferable.

Column 9 represents the % of androgenic efficacy in rat levator ani muscle, expressed in percentage of stimulation:

Where the percentage of stimulation is calculated by the following formula:

% stimulation=[$W$(compound)−$W$(control)/$W$(DHT)−
$W$(control)]×100.

W is the weight of the seminal vesicle.

Higher values are preferable.

TABLE 4

| | | IN VITRO | | IN VIVO |
| | | Shionogi Anti-androgenic Activity $IC_{50}$ (nM) | Human Androgen Receptor Binding (%) RBA R1881 = 100 | Hamster Topical 3 µg dose % inhibition vs cx |
| Name 1 | Structure 2 | 3 | 4 | 5 |
|---|---|---|---|---|
| EM-7893 | [structure] | 5.1 | 10.3 | 47 |

Legend of Table 4:

In Column 1, the laboratory name of the antiandrogens is reported.

In Column 2, the molecular structure of the antiandrogens is reported.

Column 3 represents the dose (expressed in nM) that inhibits by 50% ($IC_{50}$) the DHT-stimulated Shionogi mouse mammary carcinoma cell number. Lower values are preferable.

Column 4 represents the Relative Binding Affinity (RBA) of the antiandrogen expressed as percentage (%) on Human Androgen Receptor in transfected cells relative to R1881 as calculated by the formula:

% RBA=100×$IC_{50}$R1881/$IC_{50}$ (compound)

Higher values are preferable.

Column 5 represents the percentage of inhibition of the area of the sebaceous glands of the left ear of the treated animals versus the area of the sebaceous glands of the left ear of the control animals. A 3 µg-daily dose for 14 days of tested compound dissolved in ten µL solution of ethanol: propylene Glycol (1:1; v: v) applied onto a region between the two cartilage ridges of the ventral surface of left pinna.

Efficacy of the Preferred Inhibitors

A In vitro Assays of Androgenic/Antiandrogenic Activity of Antiandrogens

Androgenic/antiandrogenic activity of preferred compounds has been measured using the Shionogi mouse mammary carcinoma cells.

1. Materials

Minimal essential culture medium (MEM), non-essential amino acids, and fetal calf serum were purchased from Flow Laboratories. In order to remove endogenous steroids, serum was incubated overnight at 4° C. with 1% activated charcoal (Norit A, Fisher) and 0.1% Dextran T-70 (Pharmacia). A 2-h supplementary adsorption was performed at 25° C. in order to further remove protein-bound steroids. Serum was also inactivated by a 20-min incubation at 56° C.

5α-dihydrotestosterone (DHT) was obtained from Steraloids. The antiandrogen hydroxyflutamide (OH-FLU) was kindly supplied by Drs. T. L. Nagabuschan and R. Neri (Schering Corporation, Kenilworth, U.S.A.).

2. Cell Dispersion, Culture and Cloning

Shionogi male mice bearing androgen-sensitive mammary tumors were obtained from Drs. Keishi Matsumoto, Osaka, Japan, and Yvonne Lefebvre, Ottawa, Canada. For primary culture, tumors were excised and washed in ice-cold sterile 25 mM Hepes buffer (137 mM NaCl; 5 mM KCl; 0.7 mM $Na_2HPO_4$; 10 mM glucose, pH 7.2). After mincing with scissors, the tumor minces were digested for 2 h at 37° C. in Hepes buffer containing 3.8 mg/ml collagenase (Clostridium, Boehringer), 1.5 mg/ml hyaluronidase II (Sigma), and 3% bovine serum albumin fraction V (Schwartz-Mann). Dispersed cells were collected by centrifugation (500×g for 10 min), washed twice by suspension in minimal essential medium (MEM) containing 5% dextran-coated charcoal-treated fetal calf serum (DCC-FCS), 1% non-essential amino acids, 10 IU/ml penicillin, 50 µg/ml streptomycin, and 100 nM dihydrotestosterone (DHT) (Steraloids).

Cells were plated in the same medium at a density of 75 000 cells/ml in 75 $cm^2$ flasks under an atmosphere of 5% carbon dioxide in air at 37° C. The medium was changed weekly. Antiandrogens were dissolved in ethanol and kept in stock solutions chosen to yield final ethanol concentrations less than 0.01% in the culture medium. Such a concentration of ethanol does not affect cell growth.

Cells were subcultured at near-confidence by gentle digestion in a solution of 0.1% pancreatin (Flow Laboratories) in Hepes buffer containing 3 mM ethylenediaminetetraacetic acid (EDTA) (pH 7.2). Cells were pelleted by centrifugation, resuspended in culture medium, counted in a Coulter counter, and replated as described above. Soft agar cloning was performed as described (Stanley et al., Cell 10: 35-44, 1977) in the presence of 100 nM DHT.

3. Measurement of Cell Growth

Cells were plated in 24-well plates at a density of 20 000 cells/well. The indicated increasing concentrations of agents were added to triplicate dishes, and cells were grown for 10-12 days with changes of medium every 3-4 days. Cell number was measured by direct counting in a Coulter counter.

4. Calculations and Statistical Analysis $IC_{50}$ values of antiandrogens were calculated according to a least-square regression as described by Rodbard, Endocrinology. Statistical significance was calculated according to Kramer multiple-range test.

B Androgen Receptor (AR) Assays

1. Tissue Preparation

Preparation of Human Embryonic Kidney (HEK-293) Cells Transfected with Human Androgen Receptor (hAR): Cells were cultured in 6-well Falcon flasks to approximately 3×$10^5$ cells/well in Dulbecco's modified Eagle's medium (DMEM) supplemented with 10% fetal calf serum at 37° C. under a 95% air, 5% $CO_2$ humidified atmosphere. Five µg of pCMVneo-hAR plasmid were transfected using the lipofectin transfection kit (Life Technologies, Ontario, Canada). After 6 h of incubation at 37° C., the transfection medium was removed and 2 ml of DMEM were added. Cells were further cultured for 48 h and then transferred into 10 cm petri dishes and cultured in DMEM containing 700 µg/ml of G-418 in order to inhibit the growth of non-transfected cells. Medium containing G-418 was changed every two days until resistant colonies were observed. Positive clones were selected by PCR. HEK 293 cells transfected with hAR were amplified and frozen until being used for the binding assay.

HEK-293 hAR-expressing Cells Cytosol Preparation: On the morning of the binding assay, a pellet of HEK-293 hAR cells was thawed and suspended in buffer A (25 mM Tris-HCl, 1.5 mM EDTA disodium salt, 10 mM α-monothioglycerol, 10% glycerol, and 10 mM sodium molybdate, pH 7.4; 625 000 cells/0.1 ml). The cell suspension was sonicated for three periods of 30 sec (with intervals for cooling) and then centrifuged at 105 000×g for 90 min.

2. Androgen Receptor Assay

Androgen binding was measured using the hydroxylapatite (HAP) assay. In brief, the radioactive steroid [$^3$H]R1881 solubilized in ethanol was diluted into buffer B (10 mM Tris-HCl, 1.5 mM EDTA disodium salt, 10 mM α-monothioglycerol, pH 7.4). Aliquots of the cell cytosol preparation (0.1 ml) were then incubated with 5 nM [$^3$H]R1881 (0.1 ml, ~100 000 cpm) in the presence or absence of the indicated concentrations of unlabeled compounds (0.1 ml, prepared in buffer B containing 30% ethanol) for 16-18 h at 0-4° C. Triamcinolone acetonide (TAC; 100 nM) was added to mask progesterone receptors. Unbound steroids were separated by incubation for 40 min at 0-4° C. with 0.3 ml HAP prepared in buffer P (50 mM Tris-HCl, 10 mM KH2PO4, pH 7.4). After incubation with HAP and 10 min of centrifugation at 1000×g, the pellet was washed 3 times with 1 ml of buffer P. Thereafter, the radioactivity was extracted from the pellet by incubation at room temperature for 60 min with 1 ml of ethanol. After centrifugation, the supernatant was decanted into a scintillation vial and the pellet was extracted again with ethanol. After the addition of scintillation liquid, the radioactivity was measured in a liquid scintillation counter.

3. Calculations and Statistical Analysis $IC_{50}$ values of antiandrogens were calculated according to a least-square regression as described by Rodbard, Endocrinology. Statistical significance was calculated according to Kramer multiple-range test. Relative Binding Affinity (RBA) of the antiandrogen in percentage relatively to R1881 is calculated by the formula:

% RBA=100×$IC_{50}$R1881/$IC_{50}$ (compound)

C Systemic Antiandrogenic/Androgenic Activity (Immature Male Rats)

1. Animals

Immature male rats (Crl:CD(SD)Br) 22 to 24-day old were obtained from Charles-River, Inc. (St-Constant, Quebec, Canada) and housed up to 5 per cage in plastic bins in a temperature (23±1° C.)— and light (12 h light/day, lights on at 7h15)— controlled environment. The rats were fed rodent chow and tap water ad libitum. The day following their arrival, the animals were orchidectomized (CX) under Isoflurane anesthesia via scrotal route and randomly assigned to groups of 5 animals. For antiandrogenic activity, one silastic implant of dihydrotestosterone (DHT; length of implant: 1 cm) was inserted subcutaneously in the dorsal area of animals at the time of orchidectomy. One group of 5 animals was CX only as control (no DHT implant inserted).

2. Treatments

To evaluate the antiandrogenic activity, tested compounds were administered subcutaneously or orally once daily at a dose of 0.5 mg/animal for antiandrogenitic activity or 0.2 mg/animal for androgenic activity for 7 days (SD 1 to 7). Compounds were solubilized (when possible) in dimethylsulfoxide (DMSO, 10% final concentration) and administered as suspension in 0.4% methylcellulose. Rats in CX control and CX+DHT control groups received the vehicle alone during the 7-day period. One group of animals received the antiandrogen Flutamide as reference. The animals were killed by cervical dislocation under isoflurane anesthesia on the 8th morning following castration. The ventral prostate and seminal vesicles were rapidly dissected and weighed.

3. Calculations and Statistical Analysis

For antiandrogenic activity, the percentage of inhibition (% inhib) is calculated by the following formula:

% Inhib=100−[$W$(compound)−$W$(control)/$W$(DHT)−$W$(control)]×100.

For androgenic activity, the percentage of stimulation is calculated by the following formula:

% stimulation=[$W$(compound)−$W$(control)/$W$(DHT)−$W$(control)]×100.

W is the weight of the prostate, the seminal vesicle or levator ani.

D—In vivo Assessment of Topical Antiandrogenic Activity

The antiandrogenic activity of compounds for topical use was determined using the ear sebaceous glands model in the male hamster.

1. Animals

Male Golden Syrian Hamsters (SYR) of 110-120 g were obtained from Harlan Sprague-Dawley (Madison, USA) and housed up to 2 per plastic cage in a temperature (22±3° C.) and light (12 h light/day, lights on at 7h15)-controlled environment. The hamsters were fed with Certified Rodent Diet 5002 (pellet) and had access to tap water ad libitum. The animals were acclimatized for at least five days prior to beginning the study. Animals were randomly assigned to groups of eight hamsters. One group of hamsters were castrated under isoflurane-induced anesthesia on the day of dosing initiation (SD 1) and used as control group.

2. Treatments

To evaluate the antiandrogenic activity, the tested compounds were applied topically on the inner part of the left ear, once daily, for 14 days. A ten-µL solution of acetone: ethanol: propylene Glycol (1:1:2; v: v:v) containing 0.1, 0.3 or 1.0 mg/mL of the tested compound was carefully applied onto a region between the two cartilage ridges of the ventral surface of the left pinna. For animals of the castrated and intact control groups, one ten-µL vehicle was applied onto the left ear. No solution was applied on the right ear.

3. Post-Mortem Observations and Measurements

On Study Day 15, the hamsters were euthanized by cervical dislocation under isoflurane anesthesia. The left and right ears were collected attached together by the head skin, flat fixed on a paper and then immersed in 10% neutral buffered formalin. Punctures making a circular hole of 6 mm were made on the flat fixed ear in the region where the solution has been applied. These punch-made specimens were collected from each ear. Using a scalpel blade, the collected 6 mm round ear specimens were cut in the middle between the two cartilage ridges. The two equal parts of the ear round specimens were embedded in paraffin. After processing the tissue, the two parts were vertically embedded parallel to each other in such a way that the flat 6 mm area was facing out. From each paraffin block, one section (5 µm thick) was cut and collected on a glass slide. Thus, each slide contained two elongated sections of 6 mm length. Slides were stained with hematoxylin and eosin.

4. Analysis of Sebaceous Gland Area

Using the video camera and the lens number X5 of the light microscope, the resulting field appearing on the screen has a length of 0.953 mm. When the first 6 mm long section was examined from the left to the right, the first and second fields were ignored and the third and fourth fields were captured for analysis by the image analyzer. Each field has the length of 0.953 mm. With the help of the screen mouse, the sebaceous glands within the whole field length (0.953 mm) were marked. Also, an area having the length of the whole field and the height between stratum granulosum and the upper edge of the cartilage was drawn.

The total area of the sebaceous glands ($\mu m^2$) in each examined field was calculated by the Image Analyser. We also measured the total area, which has the length of 0.953 mm and the height between stratum granulosum and the cartilage. In addition, the percentage of the area occupied by the glands was obtained. Thus, for each ear, two sections were cut and two fields from each section were analyzed. The total of the four readings was averaged and the mean standard error of the mean was calculated by the image analyzer. The results were expressed in $\mu m^2$ as the total surface of glands per field and also as percentage of the area occupied by the glands in the tissue.

Some non-limiting examples of preferred active compounds are discussed below together with preferred synthesis techniques.

Examples of Synthesis of Preferred Inhibitors

Proton NMR spectra were recorded on a Brucker AC-F 300 instrument or a Brucker Avance 400 MHz. The following abbreviations have been used: s, singlet; d, doublet; dd, doublet of doublet; t, triplet; q, quadruplet; and m, multiplet. The chemical shifts (δ) were referenced to chloroform (7.26 ppm for $^1H$ and 77.00 ppm for $^{13}C$) or Acetone (2.01 ppm for $^1H$) and were expressed in ppm. Thin-layer chromatography (TLC) was performed on 0.25 mm Kieselgel 60F254 plates (E. Merck, Darmstadt, FRG). For flash chromatography, Merck-Kieselgel 60 (230-400 mesh A.S.T.M.) was used. Unless otherwise noted, starting material and reactant were obtained commercially and were used as such or purified by standard means. All solvents and reactants purified and dried were stored under argon. Anhydrous reactions were performed under an inert atmosphere, the set-up assembled and cooled under argon. Organic solutions were dried over magnesium sulfate, evaporated on a rotatory evaporator and under reduced pressure. Starting materials and reagents were available from Aldrich Chemical Company, Inc. (Milwaukee, Wis.).

Preparation of Thiohydantoins Derivatives (Table 1 and Table 3)

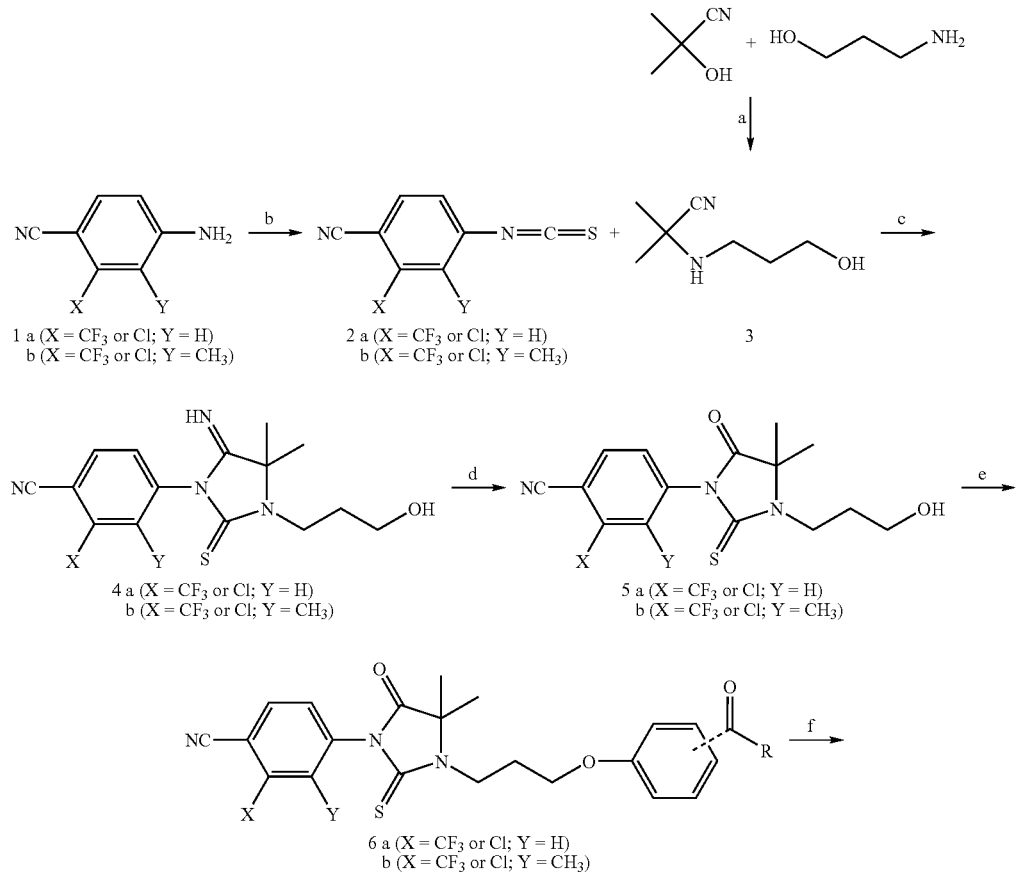

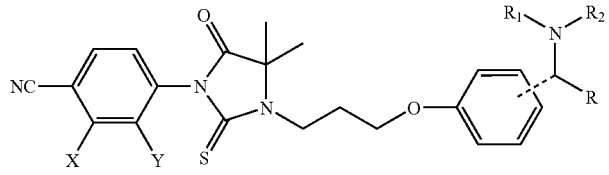

7 a (X = CF₃ or Cl; Y = H)
b (X = CF₃ or Cl; Y = CH₃)

Reagents and condtions: (a) 0° C. to rt, neat (b) CSCl₂, H₂O, rt; (c) TEA, THF, reflux; (d) 2 M aq HCl, MeOH, reflux; (e) phenol-CO—R, DIAD, PPh₃, THF; (f) NR₁R₂, NaBH₃CN, AcOH, ACN or EtOH.

5-Amino-2-cyanobenzotrifluoride (1a): commercially available (Matrix Scientific)

3-Chloro-4-cyano-2-methyl aniline (1b): synthesized as described in WO 03/096980 A2

4-Isothiocanato-2-trifluoromethyl-benzonitrile (2a): To a solution of thiophosgene (203 mg, 1.8 mmol) in demineralized water (3.0 mL) was added 5-amino-2-cyanobenzotrifluoride (1a) (300 mg, 1.6 mmol) in a small portion and the reaction was stirred at room temperature for 1 hr. The resulting solution was diluted with water (50 mL), extracted with chloroform (3×20 mL) and then filtered over a cotton plug. The resulting solution was evaporated under reduce pressure to give a crude pale brown solid (334 mg, 90%) which was directly used for the next step.

2-(3-Hydroxy-propylamino)-2-methyl-proprionitrile (3): To a neat solution of acetone cyanohydrin (930 mg, 10.9 mmol) at 0° C. was slowly added the 3-amino-1-propanol (861 mg, 11.5 mmol). The resulting solution was stirred at room temperature for 3 hrs and then evaporated under reduce pressure to give the desired compound 3 (1.1 g, 71%) which was directly used for the next step without purification.

4-[4,4-dimethyl-3-(3-hydroxypropyl)-5-imino-2-thioxo-1-imidazolidinyl]-2-trifluoromethyl-benzonitrile (4a): To a solution of compound 2a (500 mg, 2.2 mmol) in anhydrous THF (20 mL) under argon were added triethylamine (22 mg, 0.22 mmol) and 2-propylamino-2-cyano-propane (3) (328 mg, 2.3 mmol). The solution was then stirred at reflux for 1 hr. The resulting solution was evaporated to dryness and purified by flash chromatography using dichloromethane/acetone (8:2) as an eluant to give 627 mg (77%) of desired compound 4a.

4-[4,4-dimethyl-3-(3-hydroxypropyl)-5-oxo-2-thioxo-1-imidazolidinyl]-2-trifluoromethyl-benzonitrile (5a): To a solution of compound 4a (627 mg, 1.7 mmol) in methanol (27 mL) was added 2N aqueous hydrogen chloride (5.2 mL). The solution was refluxed for 90 min and then poured in an ice/water solution. The solution was extracted with ethyl acetate (3×30 mL), washed with brine, and dried over magnesium sulphate to give 428 mg (68%) of desired compound 5a. ¹H NMR (400 MHz, Acetone-d₆) δ: 1.65 (s, 6H), 3.67 (q, 2H, J=5.7 Hz), 3.75 (t, 1H, J=5.01 Hz), 3.90 (m, 2H), 8.03 (d, 1H, J=6.4 Hz), 8.18 (s, 1H), 8.26 (d, 1H, J=8.26 Hz).

General Procedure for the Synthesis of Compounds 6a:

Typically, to a stirred solution of compound 5a (0.40 mmol), triphenylphosphine (0.80 mmol) and the appropriate phenol (0.80 mmol) in anhydrous THF (0.05 M) at 0° C. was slowly added diisopropylazodicarboxylate (DIAD) (0.80 mmol) over 10 min. The solution was stirred at 0° C. for 1 hr and allowed to return at room temperature to be stirred for an additional 3 hrs. The resulting solution was diluted with ethyl acetate (60 mL), washed with a 10% NaOH solution (100 mL) and dried over sodium sulphate. Purification of the resulting crude compound by flash chromatography using CH₂Cl₂/acetone (95:5) gave compounds of general structure 6a with moderate to good yields (30 to 70%).

4-{4,4-dimethyl-5-oxo-3-[3-(3-propionyl-phenoxy)-propyl]-2-thioxo-imidazolidin-1-yl}-2-trifluoromethyl-benzonitrile (EM-7113): ¹H NMR (400 MHz, Acetone-d₆) δ: 1.15 (t, 3H, J=7.20 Hz), 1.68 (s, 6H), 2.07 (m, 2H), 3.06 (q, 2H, J=7.20 Hz), 4.05 (m, 2H), 4.24 (t, 2H, 6.13 Hz), 7.22 (m, 1H), 7.45 (t, 1H, J=7.92 Hz), 7.53 (s, 1H), 7.61 (d, 1H, 7.69 Hz), 8.03 (dd, 1H, J₁=6.45; J₂=1.81 Hz), 8.17 (s, 1H), 8.26 (d, 1H, J=8.27 Hz).

General Procedure for the Synthesis of Compounds 7a:

Typically, to a solution of compound 6a (0.15 mmol) in anhydrous acetonitrile (1 mL) were added the appropriate amine (0.60 mmol), sodium cyanoborohydride (0.23 mmol) and acetic acid (0.75 mmol). The solution was then stirred ranging from 4 to 12 hours, under argon at room temperature. The resulting solution was diluted with ethyl acetate (15 mL) and washed successively with a 10% aqueous sodium bicarbonate and a brine solution. The organic phase was dried over sodium sulphate, and evaporated under reduce pressure to give the crude amine. The crude compound was then purified by flash chromatography using ethyl acetate or acetone as an eluant to give compounds of general structure 7 with yields ranging from 35 to 60%.

Note: Thiohydantoins (1b-7b) were obtained by the same synthetic pathway, as were used for compounds (1a-7a).

4-(3-{3-[4-Isopropylamino-methyl)-phenoxy]-propyl}-4,4-dimethyl-5-oxo-2-thioxo-imidazolidin-1-yl)-2-trifluoromethyl-benzonitrile (EM-7105): ¹H NMR (400 MHz, Acetone-d₆) δ: 1.04 (d, 6H, J=6.22 Hz), 1.67 (s, 6H), 2.36 (m, 2H), 2.78 (m, 1H), 3.70 (s, 2H), 4.02 (m, 2H), 4.13 (t, 2H, J=6.16 Hz), 6.91 (d, 2H, J=4.7 Hz), 7.28 (d, 2H, J=8.6 Hz), 8.03 (dd, 1H, J₁=6.46 Hz, J₂=1.80 Hz), 8.18 (s, 1H), 8.26 (d, 1H, J=8.25 Hz).

4-(3-{3-[4-Ethylaminomethyl)-phenoxy]-propyl}-4,4-dimethyl-5-oxo-2-thioxo-imidazolidin-1-yl)-2-trifluoromethyl-benzonitrile (EM-7148): ¹H NMR (400 MHz, Acetone-d₆) δ: 1.07 (t, 3H, J=7.12 Hz), 1.67 (s, 6H), 2.36 (m, 2H), 2.60 (m, 2H), 3.70 (s, 2H), 4.02 (m, 2H), 4.13 (t, 2H, J=6.17 Hz), 6.91 (d, 2H, J=4.90 Hz), 7.27 (d, 2H, J=8.61 Hz), 8.03 (dd, 1H, J₁=6.53 Hz, J₂=1.73 Hz), 8.18 (s, 1H), 8.26 (d, 1H, J=7.95 Hz).

4-(3-{3-[4-Dimethylaminomethyl)-phenoxy]-propyl}-4,4-dimethyl-5-oxo-2-thioxo-imidazolidin-1-yl)-2-trifluoromethyl-benzonitrile (EM-7192): ¹H NMR (400 MHz, Acetone-d₆) δ: 1.67 (s, 6H), 2.16 (s, 6H), 2.36 (m, 2H), 3.32 (s, 2H), 4.02 (m, 2H), 4.14 (t, 2H, J=6.16 Hz), 6.92 (d, 2H, J=4.7 Hz), 7.23 (d, 2H, J=8.6 Hz), 8.03 (dd, 1H, J₁=6.47 Hz, J₂=1.77 Hz), 8.18 (d, 1H, J=1.71 Hz), 8.26 (d, 1H, J=8.27 Hz).

2-Chloro-4-(3-{3-[4-isopropylamino-methyl)-phenoxy]-propyl}-4, 4-dimethyl-5-oxo-2-thioxo-imidazolidin-1-yl)-3- methyl-benzonitile(EM-7198): ¹H NMR (400 MHz, Acetone-d₆) δ: 1.04 (d, 6H, J=6.22 Hz), 1.67 (s, 3H), 2.27 (s, 3H), 2.36 (m, 2H), 2.78 (m, 1H), 3.70 (s, 2H), 4.00, (m, 2H), 4.13 (t, 2H, J=6.17 Hz), 6.90 (d, 2H, J=8.60 Hz), 7.27 (d, 2H, J=8.60 Hz), 7.55 (d, 1H, J=8.27 Hz), 7.90 (d, 1H, J=8.27 Hz).

4-{4,4-Dimethyl-5-oxo-3-[3-(4-pyrrolidin-1-ylmethyl-phenoxy)-]-2-thioxo-imidazolidin-1-yl}-2-trifluoro-benzonitrile (EM-7232): ¹H NMR (400 MHz, Acetone-d₆) δ: 1.66 (s, 6H), 1.73 (m, 4H), 2.36 (m, 2H), 2.44 (broad s, 4H), 3.53 (s, 2H), 4.01 (m, 2H), 4.14 (t, 2H, J=6.16 Hz), 6.90 (d, 2H, J=8.63 Hz), 7.26 (d, 2H, J=8.56 Hz), 8.03 (dd, 1H, J₁=6.58 Hz, J₂=1.70 Hz), 8.18 (d, 1H, J=1.72 Hz), 8.26 (d, 1H, 8.27 Hz).

4-[3-(3-{4-[(Isopropyl-methyl-amino)methyl]-phenoxy}-propyl-4,4-dimethyl-5-oxo-2-thioxo-imidazolidin-1-yl)-2-tifluoromethyl-benzonitile (EM-7233): ¹H NMR (400 MHz, Acetone-d₆) δ: 1.04 (d, 6H, J=6.60 Hz), 1.67 (s, 6H), 2.09 (s, 3H), 2.36 (m, 2H), 2.88 (m, 1H), 3.47 (s, 2H), 4.02 (m, 2H), 4.13 (t, 2H, J=6.16 Hz), 6.91 (d, 2H, J=8.60 Hz), 7.26 (d, 2H, J=8.57 Hz), 8.03 (dd, 1H, J₁=6.64 Hz; J₂=1.63 Hz), 8.17 (s, 1H), 8.26 (d, 1H, J=8.27 Hz).

4-(3-{3-[4-(1-Isopropylamino-ethyl)-phenoxy]-propyl}-4,4-dimethyl-5-oxo-2-thioxo-imidazolidin-1-yl)-2-tifluoromethyl-benzonitile (EM-7234): ¹H NMR (400 MHz, Acetone-d₆) δ: 0.99 (m, 6H), 1.26 (d, 3H, J=6.60 Hz), 1.67 (s, 6H), 2.37 (m, 2H), 2.61 (m, 1H), 3.90 (m, 1H), 4.02 (m, 2H), 4.14 (t, 2H, J=6.17 Hz), 6.92 (d, 2H, J=8.60 Hz), 7.30 (d, 2H, J=8.59 Hz), 8.03 (dd, 1H, J₁=6.57 Hz; J₂=1.60 Hz), 8.17 (s, 1H), 8.26 (d, 1H, J=8.24 Hz).

4-(3-{3-[4-(1-methylsulfonyl)-phenoxy]-propyl}-4,4-dimethyl-5-oxo-2-thioxo-imidazolidin-1-yl)-2-chloro-3-methyl-benzonitrile (EM-8260): ¹H NMR (400 MHz, Acetone-d₆) δ: 1.67 (d, 6H, J=3.7 Hz), 2.26 (s, 3H), 2.43 (m, 2H), 3.07 (s, 3H), 4.04 (m, 2H), 4.30 (t, 2H, J=6.17 Hz), 7.19 (d, 2H, J=8.92 Hz), 7.53 (d, 2H, J=8.32 Hz), 7.88 (m, 3H).

Preparation of Hydantoins Derivatives (Table 1)

Scheme 2

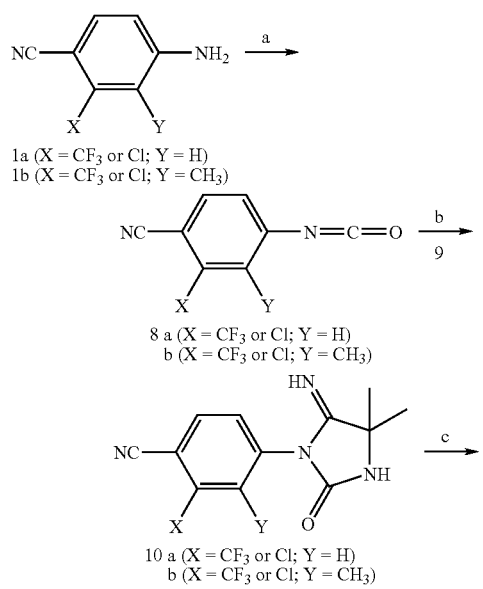

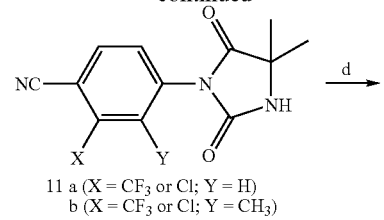

11 a (X = CF₃ or Cl; Y = H)
b (X = CF₃ or Cl; Y = CH₃)

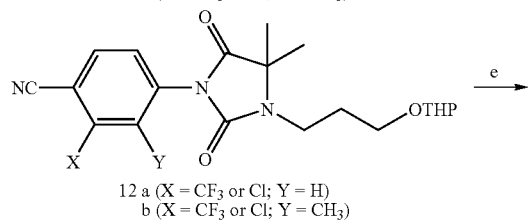

12 a (X = CF₃ or Cl; Y = H)
b (X = CF₃ or Cl; Y = CH₃)

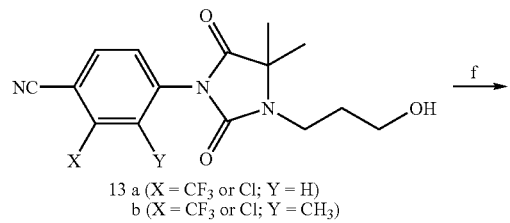

13 a (X = CF₃ or Cl; Y = H)
b (X = CF₃ or Cl; Y = CH₃)

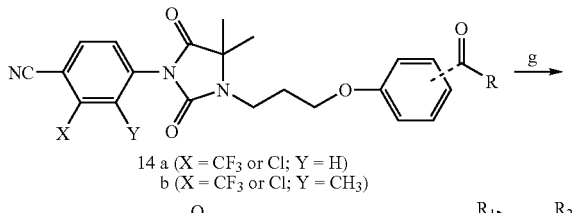

14 a (X = CF₃ or Cl; Y = H)
b (X = CF₃ or Cl; Y = CH₃)

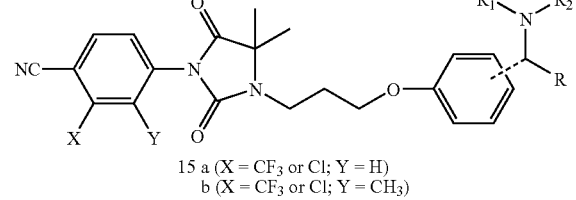

15 a (X = CF₃ or Cl; Y = H)
b (X = CF₃ or Cl; Y = CH₃)

Reagents and condtions: (a) phosgene/toluene, toluene, reflux; (b) 9, TEA, 1,2 dichloroethane, 0° C. to rt; (c) 6 N HCl, reflux; (d) NaH, 1-chloropropyl-3-OTHP, DMF, 50° C.; (e) p-TSA, MeOH; (f) Phenol-R, PPh₃, DEAD, THF, 0° C. to rt; (g) NR₁R₂, NaBH₃CN, AcOH, ACN or EtOH.

4-Isocyanato-2-trifluoromethyl-benzonitrile (8a)

To a solution of 5-amino-2-cyanobenzotrifluoride (1a) (2.0 g, 10.7 mmol) in ethyl acetate (6 mL) at 0° C. under argon, was added dropwise a 2.0 M solution of phosgene in toluene (6.5 mL, 12.9 mmol). The solution was stirred 30 min at 0° C. and allowed to return at room temperature. Toluene (3 mL) was then added to the ethyl acetate and the resulting solution was refluxed for 3 hrs using a Dean-Stark apparatus, equipped with an HCl trap (solid NaOH). The first 6 mL of distilled solvent was removed and replaced by toluene (6 mL). The solution was then filtrated and evaporated to give compound 8a (1.6 g) as an orange oil which was directly used for the next step. IR: 2268 (strong), 2232 (weak) cm⁻¹.

2-Amino-2-methyl-proprionitrile (9)

To a stirred solution of aqueous ammonium hydroxide (25%) (120 mL, 0.85 mol), NaCN (15.34 g, 0.31 mol) and ammonium chloride (19.75 g, 0.37 mol) was added dropwise acetone (14.52 g, 0.25 mol) at room temperature. The solution was stirred for 3 days at room temperature. The resulting solution was extracted with dichloromethane (3×50 mL) and filtered over a cotton plug. Sodium sulphate was added to the combined organic phase and stirred for 3 hrs. Finally the solution was filtered and evaporated under reduce pressure to give the desired compound 9 (7.80 g, 45%). $^1$H NMR (400 MHz, CDCl$_3$) δ: 1.48 (s, 6H), 1.64 (broad s, 2H).

4-(4,4-Dimethyl-5-imino-2-oxo-1-imidazolidinyl)-2-trifluoromethyl-benzonitrile (10a)

To a solution of compound 9 (641 mg, 7.62 mmol) and triethylamine (168 mg, 1.66 mmol) in 1,2 dichloroethane (8.4 mL) at 0° C. under argon was dropwise added a solution of the isocyanate 8a (1.54 g, 7.28 mmol) in 1,2 dichloroethane (3.5 mL). The solution was stirred at 0° C. for 35 min and the ice bath was then removed and stirred at room temperature for an additional 30 min. The solution was then evaporated to dryness and purified by flash chromatography using EtOAc/Hexane (6:4) as an eluant to give pure compound 10a (1.02 g, 47%). $^1$H NMR (300 MHz, Acetone-d$_6$) δ: 1.54 (m, 6H), 7.45 (broad s, 1H), 8.12 (d, 1H, J=8.46 Hz), 8.29 (dd, 1H, J$_1$=6.90 Hz, J$_2$=1.61 Hz), 8.46 (s, 1H), 8.51 (s, 1H).

4-(4,4-Dimethyl-2,5-dioxo-1-imidazolidinyl)-2-trifluoromethyl-benzonitrile (11a)

A suspension of the compound 10a in 6N HCl (25 mL) was refluxed for 35 min. The cooled solution was poured in a 10% bicarbonate solution, extracted using ethyl acetate (3×25 mL). The organic layer was washed with brine, and finally dried over magnesium sulphate to give of desired compound 11a (950 mg, 95%) which was used as such in the next step. $^1$H NMR (300 MHz, Acetone-d$_6$) δ: 1.54 (s, 6H), 7.81 (broad s, 1H), 8.17 (m, 2H), 8.26 (s, 1H).

4-{4,4-Dimethyl-2,5-dioxo-3-[3-(tetrahydro-furan-2-yloxy)-propyl]-imidazolidin-1-yl}-2-trifluoromethyl-benzonitrile (12a):

To a solution of compound 11a (950 mg, 3.20 mmol) in anhydrous DMF (10 mL) under argon at room temperature was carefully added sodium hydride (60% suspension in oil) (140 mg, 3.50 mmol). The solution was stirred for 30 min and 2-(3-chloropropoxy)-tetrahydro-2H-pyran (656 mg, 3.66 mmol) was dropwise added. Finally, sodium iodide (480 mg, 3.20 mmol) was added and the solution was heated at 50° C. for 36 hrs. The resulting solution was diluted with diethyl ether (75 mL), washed successively with a 10% potassium phosphate and brine solution, and finally dried with magnesium sulphate. The crude compound was purified by flash chromatography using EtOAc/Hexane (3:7) as an eluant to give pure compound 12a (1.03 g, 73%). $^1$H NMR (300 MHz, Acetone-d$_6$) δ: 1.51 (m, 4H), 1.57 (s, 6H), 1.6-1.9 (m, 2H), 2.04 (m, 2H), 3.50 (m, 4H), 3.80 (m, 2H), 4.59 (t, 1H, J=3.42 Hz), 8.18 (m, 2H), 8.27 (s, 1H).

4-[3-(3-Hydroxy-propyl)-4,4-dimethyl-2,5-dioxo-imidazolidin-1-yl]-2-trifluoromethyl-benzonitrile (13a):

To a solution of compound 12a (1.03 g, 2.33 mmol) in methanol (10 mL) at room temperature was added p-TSA (88 mg, 0.46 mmol). The solution was stirred for 3 hrs at room temperature. The reaction was then diluted with ethyl acetate (50 mL), washed successively with a 10% bicarbonate and brine solution and finally dried over magnesium sulphate to give compound 13a (786 mg, 95%) which was directly used as such in the next step. $^1$H NMR (300 MHz, Acetone-d$_6$) δ: 1.57 (s, 6H), 1.92 (m, 2H), 3.54, (t, 2H, J=7.38 Hz), 3.51-3.63 (m, 2H), 8.18 (m, 2H), 8.27 (s, 1H).

General Procedure for the Synthesis of Compounds 14a:

Typically, to a stirred solution of alcohol 13a (0.70 mmol), triphenylphosphine (1.50 mmol) and the appropriate phenol (1.40 mmol) in anhydrous THF (0.05 M) at 0° C. was slowly added diethylazodicarboxylate (DEAD) (1.40 mmol) over 10 min. The solution was stirred at 0° C. for 1 hr and allowed to return at room temperature to be stirred for an additional 3 hrs. The resulting solution was diluted with ethyl acetate (120 mL), washed with a 10% NaOH solution (200 mL) and dried over sodium sulphate. Purification of the resulting crude compound by flash chromatography using CH$_2$Cl$_2$/acetone (99:1) gave compounds of general structure 14a with moderate to good yields (45 to 70%).

General Procedure for the Synthesis of Compounds 15a:

Typically, to a solution of compound 14a (0.11 mmol) in anhydrous acetonitrile (2.5 mL) were added the appropriate amine (0.45 mmol), sodium cyanoborohydride (0.17 mmol) and acetic acid (0.55 mmol). The solution was then stirred ranging from 4 to 12 hours, under argon at room temperature. The resulting solution was diluted with ethyl acetate (15 mL) and washed successively with a 10% aqueous sodium bicarbonate and a brine solution. The organic phase was dried over sodium sulphate, and evaporated under reduced pressure. The crude compound was then purified by flash chromatography using ethyl acetate and acetone as an eluant to give compounds of general structure 15a with good yields (60-70%).

4-{3-[3-(4-Dimethylaminomethyl-phenoxy)-propyl]-4,4-dimethyl-2,5-dioxo-imidazolidin-1-yl}-2-trifluoromethyl-benzonitrile (EM-7334): $^1$H NMR (400 MHz, Acetone-d$_6$) δ: 1.57 (s, 6H), 2.14 (s, 6H), 2.23 (m, 2H), 3.31 (s, 2H), 3.64 (t, 2H, J=7.30 Hz), 4.12 (t, 2H, J=6.07 Hz), 6.88 (d, 2H, J=8.60 Hz), 7.21 (d, 2H, J=8.55 Hz), 8.16 (m, 2H), 8.27 (s, 1H).

Note: The hydantoins derivatives of type 15b could be obtained by the same synthetic pathway, as were used for compounds 15a.

Preparation of Succinimide Derivatives (Table 1)

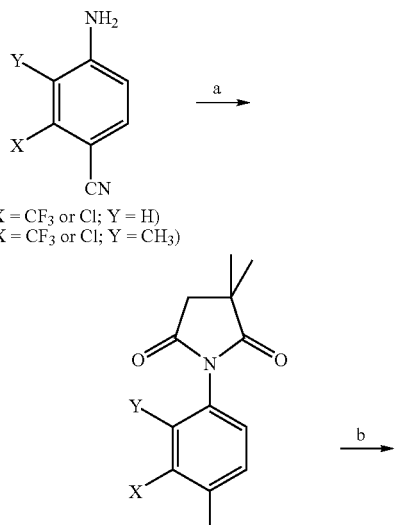

Scheme 3

1 a (X = CF$_3$ or Cl; Y = H)
 b (X = CF$_3$ or Cl; Y = CH$_3$)

16 a (X = CF$_3$ or Cl; Y = H)
  b (X = CF$_3$ or Cl; Y = CH$_3$)

103

-continued

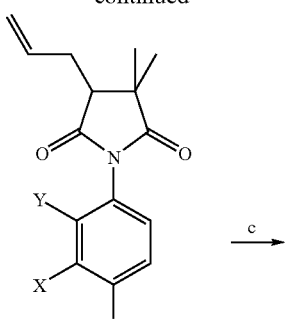

17 a (X = CF₃ or Cl; Y = H)
  b (X = CF₃ or Cl; Y = CH₃)

c →

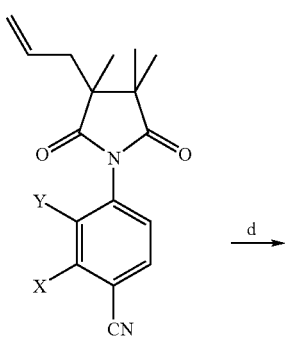

18 a (X = CF₃ or Cl; Y = H)
  b (X = CF₃ or Cl; Y = CH₃)

d →

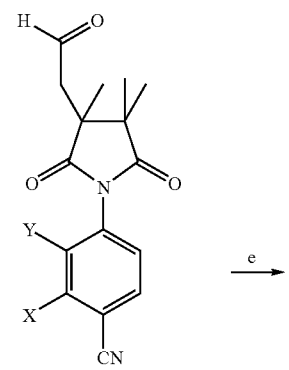

19 a (X = CF₃ or Cl; Y = H)
  b (X = CF₃ or Cl; Y = CH₃)

e →

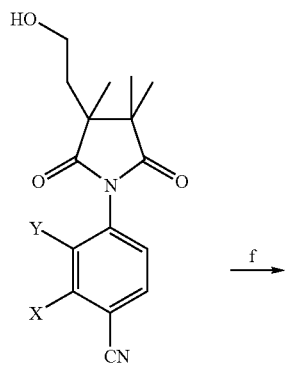

20 a (X = CF₃ or Cl; Y = H)
  b (X = CF₃ or Cl; Y = CH₃)

f →

104

-continued

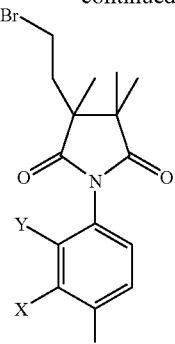

21 a (X = CF₃ or Cl; Y = H)
  b (X = CF₃ or Cl; Y = CH₃)

g →

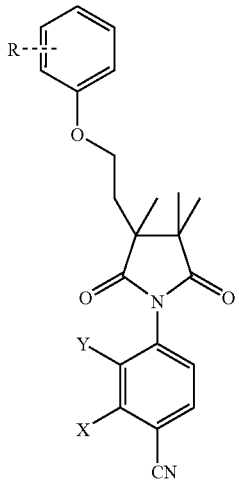

22 a (X = CF₃ or Cl; Y = H)
  b (X = CF₃ or Cl; Y = CH₃)

Reagents and conditions: (a) 2,2 dimethyl succinic anhydride, 220° C.; (b) LiHMDS, allyl bromide, THF, -78° C. to rt.; (c) LiHMDS, MeI, THF, -78° C. to rt.; (d) RuCl₃—H₂O, NaIO₄, CH₃CN/H₂O (6:1), rt.; (e) NaBH₄, AcOH, rt.; (f) PPh₃, CBr₄, CH₂Cl₂, 0° C. to rt.; (g) Phenol-R, Cs₂CO₃, DMF, 70° C.

4-(3,3-dimethyl-2,5-dioxo-1-pyrrolidinyl)-2-trifluoromethyl-benzonitrile (16a):

2,2 Dimethyl succinic anhydride (2.0 g, 15.6 mmol) and 4-amino-2-trifluoromethyl-benzonitrile 1a (2.91 g, 15.6 mmol) was heated at 220° C. for 2 hrs. The resulting solid (4.59 g, 99%) was used as such in the next step. $^1$H NMR (400 MHz, Acetone-$d_6$) δ: 1.44 (s, 6H), 2.84 (s, 2H), 7.97 (dd, 1H, $J_1$=6.74 Hz, $J_2$=1.63 Hz), 8.08 (s, 1H), 8.24 (d, 1H, J=8.32 Hz).

4-[3,3,dimethyl-2,5-dioxo-4-(2-allyl)-1-pyrrolidinyl]-2-trifluoromethyl-benzonitrile (17a):

To a solution of compound 16a (500 mg, 1.69 mmol) in anhydrous THF (20 mL) under argon was added LiHMDS (1.90 mL, 1.94 mmol) (1.0 M in THF) at −78° C. The solution was stirred for 30 min before the dropwise addition of allyl bromide (245 mg, 2.03 mmol). The resulting solution was allowed to return to room temperature and was stirred for an additional 90 min. The solution was then diluted with ethyl acetate (75 mL), washed successively with water and brine, dried over magnesium sulphate and finally evaporated. Purification of the resulting crude product by flash chromatography using ethyl acetate/hexane (1:9) as an eluant gave the desired compounds 17a in moderate yields (120 mg, 32%). $^1$H NMR (400 MHz, Acetone-$d_6$) δ: 1.38 (s, 3H), 1.43 (s, 3H), 2.45 (m, 1H), 2.80 (m, 1H), 3.06 (m, 1H), 5.12 (d, 1H, J=10.21 Hz), 5.24 (d, 1H, J=17.15 Hz), 6.05 (m, 1H), 7.98 (d, 1H, J=8.29 Hz), 8.08 (s, 1H), 8.24 (d, 1H, J=8.33 Hz).

4-[3,3,4-trimethyl-2,5-dioxo-4-(2-allyl)-1-pyrrolidinyl]-2-trifluoromethyl-benzonitrile (18a):

To a solution of compound 17a (100 mg, 0.296 mmol) in anhydrous THF (5 mL) under argon was added LiHMDS (0.31 mL, 0.326 mmol) (1.0 M in THF) at −78° C. The solution was stirred for 30 min before the dropwise addition of methyl iodide (126 mg, 0.887 mmol). The resulting solution was allowed to return to room temperature and was stirred for an additional 60 min. The solution was then diluted with ethyl acetate (30 mL), washed successively with water and brine, dried over magnesium sulphate and finally evaporated to give compound 18a (94 mg, 90%) used as such in the next step. $^1$H NMR (400 MHz, Acetone-$d_6$) δ: 1.30 (s, 3H), 1.34 (s, 3H), 1.38 (s, 3H), 2.51 (m, 2H), 5.17 (m, 2H), 5.89 (m, 1H), 7.98 (dd, 1H, $J_1$=6.40 Hz, $J_2$=1.90 Hz), 8.07 (s, 1H), 8.24 (d, 1H, J=8.39 Hz).

4-[3,3,4-trimethyl-2,5-dioxo-4-(2-acetaldehyde)-1-pyrrolidinyl]-2-trifluoromethyl-benzonitrile (19a):

To a solution of compound 18a (94 mg, 0.267 mmol) in acetonitrile/H$_2$O (6:1) (5 mL) under argon was added ruthenium (III) chloride hydrate (2 mg, 0.01 mmol), and the solution was stirred for 5 min. After then, small portions of sodium periodate (171 mg, 0.799 mmol) was added and stirred for an additional 2 hrs at room temperature. The resulting solution was diluted with ethyl acetate (25 mL), washed successively with a sodium bisulfite solution and brine, dried over sodium sulphate and finally evaporated under reduce pressure. Purification of the resulting crude product by flash chromatography using ethyl acetate/hexane (4:6) as an eluant gave the desired compounds 19a in moderate yields (39 mg, 40%).

4-[3,3,4-trimethyl-2,5-dioxo-4-(2-hydroxy-ethyl)-1-pyrrolidinyl]-2-trifluoromethyl-benzonitrile (20a):

To a solution of compound 19a (39 mg, 0.115 mmol) in acetic acid (2 mL) at room temperature was added sodium borohydride (8.5 mg, 0.230 mmol) and the solution was then stirred at room temperature for 1 hr. The resulting solution was diluted with ethyl acetate (25 mL), washed successively with a 10% sodium bicarbonate solution and brine, dried over magnesium sulphate, and finally evaporated under reduce pressure to give crude compound 20a which was used as such in the next step.

4-[3,3,4-trimethyl-2,5-dioxo-4-(2-bromo-ethyl)-1-pyrrolidinyl]-2-trifluoromethyl-benzonitrile (21a):

To a solution of compound 20a (33 mg, 0.097 mmol) in anhydrous dichloromethane (2 mL) at 0° C. under argon were added triphenylphosphine (50 mg, 0.194 mmol) and carbontetrabromide (64 mg, 0.194 mmol). The solution was allowed to return to room temperature and stirred for 1 hr. The resulting solution was diluted with dichloromethane (25 mL) and filtered on a cotton plug. Purification of the resulting crude product by flash chromatography using a gradient of ethyl acetate/hexane (3:97 to 3:7) as an eluant gave the desired compound 21a (15 mg, 40% for 2 steps). $^1$H NMR (400 MHz, Acetone-$d_6$) δ: 1.36 (s, 3H), 1.39 (s, 3H), 1.40 (s, 3H), 2.28 (m, 2H), 3.68 (m, 2H), 8.03 (dd, 1H, $J_1$=6.57 Hz, $J_2$=1.84 Hz), 8.14 (d, 1H, J=1.45 Hz), 8.24 (d, 1H, J=8.40 Hz).

General Procedure for the Synthesis of Compounds 22a:

To a solution of appropriate phenol (0.055 mmol) in dimethylformamide (1 mL) was added cesium carbonate (0.055 mmol). The solution was heated at 70° C. under argon and stirred for 30 min, before the addition of compound 21a (0.037 mmol). The resulting solution was stirred for an additional 60 min. The solution was then poured in water (20 mL), extracted with diethyl ether (3×10 mL), washed with brine, dried with magnesium sulphate and finally evaporated under reduce pressure. Purification of the resulting crude product by flash chromatography using a gradient of ethyl acetate/hexane (3:7 to 100:0) as an eluant gave the desired compounds 22a in moderate yields (15-33%).

4-[3-(2-{3-[1-(1-Ethyl-propylamino)-butyl]-phenoxy}-ethyl)-3,4,4-trimethyl-2,5-dioxo-pyrrolidin-1-yl]-2-trifluoromethyl-benzonitrile (EM-6926):

$^1$H NMR (400 MHz, Acetone-$d_6$) δ: 0.74-0.87 (m, 9H), 1.16-1.50 (m, 8H), 1.38 (s, 3H), 1.42 (s, 3H), 1.45 (s, 3H), 2.08-2.34 (m, 3H), 3.67 (t, 1H, J=6.81 Hz), 4.22 (m, 2H), 6.71 (m, 1H), 6.89 (m, 2H), 7.18 (m, 1H), 7.96 (m, 1H), 8.07 (d, 1H, J=1.67 Hz), 8.19 (m, 1H).

Note: The succinimide derivatives of type 22b could be obtained by the same synthetic pathway, as were used for compounds 22a.

Preparation of Piperidine Derivatives (Table 3)

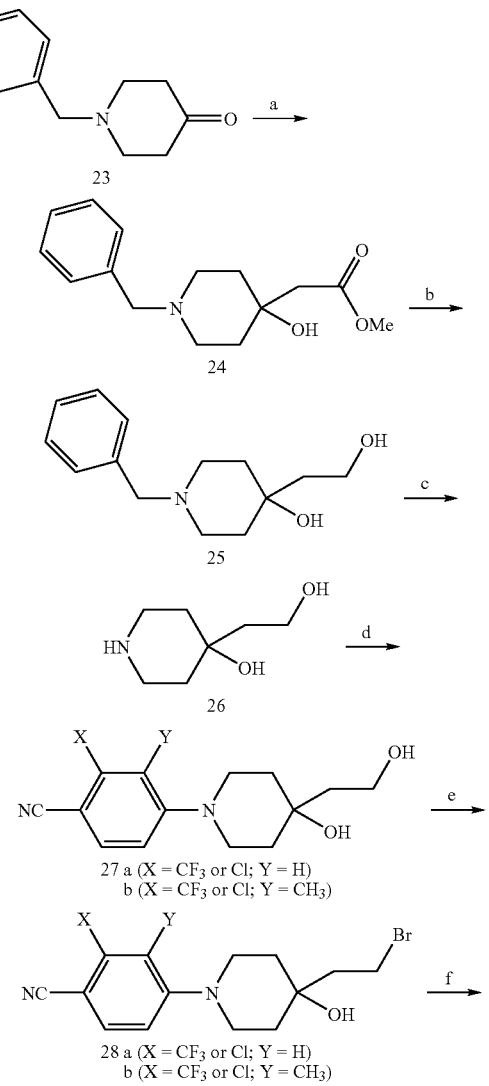

Scheme 4

-continued

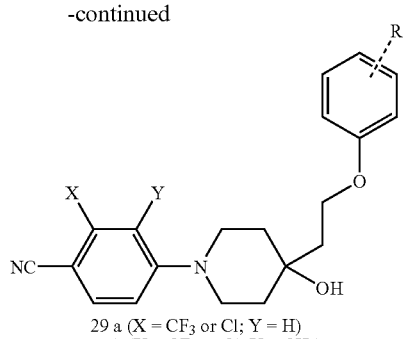

29 a (X = CF₃ or Cl; Y = H)
b (X = CF₃ or Cl; Y = CH₃)

Reagents and condtions: (a) BrCH₂CO₂Me, Zn/Cu, TMSCl, THF, rt.; (b) LiAlH₄, THF, 0° C.; (c) Pd—OH/C (20%), MeOH, 60° C.; (d) 4-fluoro-2(trifluoromethyl))benzonitrile or 2-chloro-4-fluoro-benzonitrile, TEA, DMF, 80° C.; (e) PPh₃, CBr₄, K₂CO₃, CH₂Cl₂, rt; (f) Phenol-R, CS₂CO₃, DMF, 80° C.

(1-Benzyl-4-hydroxy-piperidin-4-yl)-acetic acid methyl ester (24): To a freshly prepared solution of methylester methylzinc bromide (4.43 g, 20.2 mmol) in THF (16 mL) was slowly added the 1-benzyl-4-piperidone (23, Aldrich) (2.10 g, 10.1 mmol) at room temperature. The solution was then stirred overnight at room temperature under argon. The resulting solution was poured in water (100 mL) and extracted with diethyl ether (3×30 mL). The combined organic phases were washed with a 0.2 N HCl solution and then neutralised with 0.2 N NaOH solution. The organic phase was finally washed with brine solution, dried with magnesium sulphate and evaporated under reduce pressure. Purification of the resulting crude compound by flash chromatography using ethyl acetate/hexane (7:3) as an eluant gave the desired compound 24 (1.70 g, 60%). $^1$H NMR (400 MHz, Acetone-$d_6$) δ: 1.3-1.55 (m, 2H), 1.6-1.7 (m, 2H), 2.2-2.7 (m, 6H), 2.45-2.65 (m, 5H), 7.31 (m, 5H).

1-Benzyl-4-(2-hydroxy-ethyl)-piperidin-4-ol (25): To a solution of compound 24 (1.70 g, 6.07 mmol) in anhydrous THF (40 mL) at 0° C. was slowly added a solution of lithium aluminium hydride (1.0M in THF) (12.1 mL, 12.1 mmol). The solution was then stirred at 0° C. for 1 hr and allowed to return to room temperature to be stirred for an additional 2 hrs. The resulting solution was poured in a cold 10% solution of sodium sulphate (300 mL), extracted with diethyl ether (3×75 mL), washed with brine and finally dried over magnesium sulphate to give the crude compound 25 (1.32 g, 87%) which was used as such in the next step. $^1$H NMR (400 MHz, MeOD) δ: 1.65 (m, 4H), 1.72 (t, 2H, J=7.06 Hz), 2.45 (m, 2H), 2.62 (m, 2H), 3.56 (s, 2H), 3.76 (t, 2H, J=7.06 Hz), 7.31 (m, 5H).

4-(2-Hydroxy-ethyl)-piperidin-4-ol (26): To a solution of compound 25 (1.32 g, 5.30 mmol) in methanol (10 mL) under argon was added palladium hydroxide (20%) on activated charcoal (132 mg, 10% w/w). The solution was purged three times with hydrogen and stirred under hydrogen atmosphere at 60° C. for 4 hrs. The resulting solution was then filtered on celite plug to give desired compound 26 (790 mg, 94%) which was used as such for the next step.

4-[4-Hydroxy-4-(2-hydroxy-ethyl)-piperidin-1-yl]-2-trifluoromethyl-benzonitrile (27a): To a solution of compound 26 (517 mg, 3.25 mmol) in anhydrous dimethylformamide (15 mL) under argon were added triethylamine (1.32 g, 13.0 mmol) and 4-fluoro-2-trifluoromethylbenzonitrile (1.80 g, 9.52 mmol). The solution was stirred at 80° C. for 4 hrs. The solution was cooled at room temperature and poured in water (100 mL), extracted with diethyl ether (3×25 mL), washed with brine and finally dried over magnesium sulphate. Purification of the resulting crude product by flash chromatography using ethyl acetate/hexane (7:3) as an eluant gave the desired compound 27a (687 mg, 68%). $^1$H NMR (400 MHz, Acetone-$d_6$) δ: 1.74 (m, 6H), 3.45 (m, 2H), 3.85 (m, 4H), 7.24 (dd, 1H, $J_1$=6.4 Hz, $J_2$=2.5 Hz), 7.32 (d, 1H, J=2.4 Hz), 7.72 (d, 1H, J=8.8 Hz).

4-[4-(2-Bromo-ethyl)-4-hydroxy-piperidin-1-yl]-2-trifluoromethyl-benzonitrile (28a): To a solution of compound 27a (687 mg, 2.09 mmol) in anhydrous dichloromethane (10 mL) at 0° C. under argon were added potassium carbonate (1.16 g, 8.39 mmol), triphenylphosphine (1.1 g, 4.19 mmol) and carbon tetrabromide (1.39 g, 4.19 mmol). The solution was allowed to return to room temperature and stirred for 1 hr. The resulting solution was diluted with dichloromethane (50 mL) and filtered on a cotton plug. Purification of the resulting crude product by flash chromatography using ethyl acetate/hexane (2:8) gave the desired compound 28a (470 mg, 57%). $^1$H NMR (400 MHz, MeOD) δ: 1.72 (m, 4H), 2.11 (m, 2H), 3.37 (m, 2H), 3.54 (m, 2H), 3.77 (m, 2H), 7.18 (dd, 1H, $J_1$=6.26 Hz, $J_2$=2.62 Hz), 7.27 (d, 1H, J=2.07 Hz), 7.69 (d, 1H, J=8.83 Hz).

General procedure for the synthesis of compounds 29a: To a solution of appropriate phenol (0.116 mmol) in dimethylformamide (3 mL) was added cesium carbonate (0.190 mmol). The solution was heated at 70° C. under argon and stirred for 30 min, before the addition of compound 28a (30 mg, 0.079 mmol). The resulting solution was stirred for an additional 4 hrs. The solution was then poured in water (50 mL), extracted with diethyl ether (3×20 mL), washed with a brine solution, dried with magnesium sulphate and finally evaporated under reduce pressure. Purification of the resulting crude product by flash chromatography using ethyl acetate (100%) as an eluant gave the desired compounds 29a in moderate to good yields (40-70%).

4-{4-[2-(4-Cyclohexylaminomethyl-phenoxy)-ethyl]-4-hydroxy-piperidin-1-yl}-2-trifluoromethyl-benzonitrile (EM-7332): $^1$H NMR (400 MHz, Acetone-$d_6$) δ: 1.20 (broad s, 8H), 1.81 (m, 4H), 2.00 (m, 4H), 2.60 (m, 1H), 3.48 (m, 2H), 3.79 (s, 2H), 3.86 (m, 2H), 4.22 (t, 2H, J=6.64 Hz), 6.88 (d, 2H, J=8.44 Hz), 7.29 (m, 4H), 7.73 (d, 1H, J=8.85 Hz).

4-{4-Hydroxy-4-[2-(2-methyl-4-morpholin-4-ylmethyl-phenoxy)-ethyl]-piperidin-1-yl}-2-trifluoromethyl-benzonitrile (EM-7363): $^1$H NMR (400 MHz, Acetone-$d_6$) δ: 1.85 (m, 4H), 2.07 (m, 2H), 2.17 (s, 3H), 2.36 (broad s, 4H), 3.37 (s, 2H), 3.55 (m, 2H), 3.60 (t, 4H, J=4.61 Hz), 3.77 (s, 1H), 3.89 (m, 2H), 4.24 (t, 2H, J=6.43 Hz), 6.88 (d, 1H, J=8.40 Hz), 7.09 (m, 2H), 7.26 (dd, 1H, $J_1$=6.26 Hz, $J_2$=2.61 Hz), 7.35 (d, 1H, J=2.5 Hz), 7.74 (d, 1H, J=8.85 Hz).

4-(4-{2-[4-(2,6-Dimethyl-piperidin-1-yl-methyl)-phenoxy]-ethyl}-4-hydroxy-piperidin-1-yl)-2-trifluoromethyl-benzonitrile (EM-7421):
$^1$H NMR (400 MHz, Acetone-$d_6$) δ: 1.01 (broad s, 6H), 1.31 (broad s, 4H), 1.62 (broad d, 4H, J=17.36 Hz), 1.82 (m, 4H), 3.48 (m, 2H), 3.78 (s, 1H), 3.87 (m, 2H), 4.22 (m, 2H), 6.89 (m, 2H), 7.27 (dd, 1H, $J_1$=6.26 Hz, $J_2$=2.62 Hz), 7.35 (m, 3H), 7.74 (d, 1H, J=8.95 Hz).

4-(4-{2-[4-(1-propyl-3-aminopentyl)-phenoxy]-ethyl}-4-hydroxy-piperidin-1-yl)-2-trifluoromethyl-benzonitrile (EM-7892): $^1$H NMR (400 MHz, Acetone-$d_6$) δ: 0.79 (m, 9H), 1.20-1.65 (m, 7H), 1.82 (m, 4H), 2.02 (m, 3H), 2.17 (m, 1H), 3.55 (m, 3H), 3.85 (m, 2H), 4.22 (t, 2H, J=6.63 Hz), 6.87 (d, 2H, J=8.65 Hz), 7.23 (d, 2H, J=8.54 Hz), 7.27 (d, 1H, J=2.57 Hz), 7.34 (d, 1H, J=2.45 Hz), 7.73 (d, 1H, J=8.87 Hz).

4-(4-{2-[4-(1-propyl-pyrolidine)-phenoxy]-ethyl}-4-hydroxy-piperidin-1-yl)-2-trifluoromethyl-benzonitrile (EM-7893): $^1$H NMR (400 MHz, Acetone-$d_6$) δ: 0.64 (t, 3H, J=7.41 Hz), 1.67 (broad s, 5H), 1.82 (m, 4H), 1.88 (m, 1H), 2.02 (t, 2H, J=6.65 Hz), 2.31 (broad dd, 4H, J$_1$=61.6 Hz, J$_2$=5.36 Hz), 2.93 (m, 1H), 3.47 (m, 2H), 3.86 (m, 2H), 4.22 (t, 2H, J=6.63 Hz), 6.87 (d, 2H, J=8.65 Hz), 7.19 (d, 2H, J=8.55 Hz), 7.26 (dd, 1H, J$_1$ 6.29=Hz, J$_2$=2.57 Hz), 7.34 (d, 1H, J=2.46 Hz), 7.73 (d, 1H, J=8.86 Hz).

Note: The piperidine derivatives of type 29b could be obtained by the same synthetic pathway, as were used for compounds 29a.

Preparation of Piperazine Derivatives (Table 3)

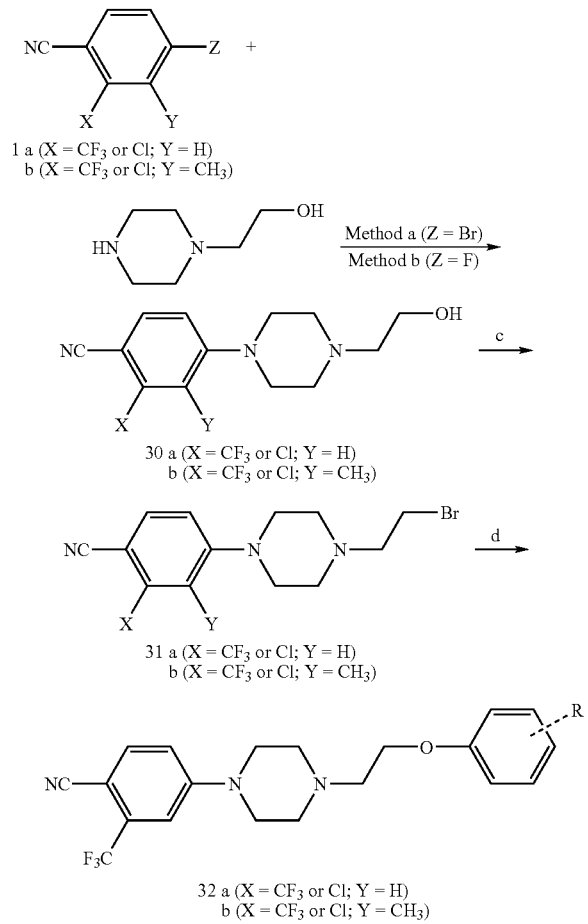

Scheme 5

Reagents and conditions: (a) Pd$_2$(dba)$_3$, Cs$_2$CO$_3$, BINAP, Toluene, 100° C.; (b) DMF, TEA, 80° C.; (c) PPh$_3$, CBr$_4$, K$_2$CO$_3$, CH$_2$Cl$_2$, rt; (d) phenol-R, Cs$_2$CO$_3$, DMF, 70° C.

4-[4-(2-Hydroxy-ethyl)-piperazin-1-yl]-2-trifluoromethyl-benzonitrile (30a):

Method a:

In a Schlenk tube purged with argon were added Pd(dba)$_3$ (13 mg, 0.015 mmol), BINAP (13 mg, 0.02 mmol) and cesium carbonate (627 mg, 1.92 mmol). The 4-bromo-2-trifluoromethyl-benzonitrile (500 mg, 2.0 mmol) and the 1-(2-hydroxyethyl)piperidine in anhydrous toluene (1.5 mL) was added to the Schlenk tube and the solution was then heated at 100° C. overnight. The resulting solution was diluted with ethyl acetate (25 mL), filtered on celite, and evaporated under reduce pressure. Purification of the resulting crude product by flash chromatography using ethyl acetate (100%) as eluant gave the desired compound 21 (60 mg, 10%). $^1$H NMR (400 MHz, Acetone-d$_6$) δ: 2.55 (t, 2H, J=5.82 Hz), 2.65 (t, 4H, J=5.09 Hz), 3.52 (t, 4H, J=5.11 Hz), 3.65 (t, 2H, J=5.79 Hz), 7.24 (dd, 1H, J$_1$=6.38 Hz, J$_2$=2.50 Hz), 7.33 (d, 1H, J=2.43 Hz), 7.76 (d, 1H, J=8.83 Hz).

Method B: See Experimental Procedure for Compound 27a.

4-[4-(2-Bromo-ethyl)-piperazin-1-yl]-2-trifluoromethyl-benzonitrile (31a):

To a solution of alcohol 30a (35 mg, 0.12 mmol) in dichloromethane (4 mL) at 0° C. were added potassium carbonate (71 mg, 0.51 mmol), triphenylphosphine (88 mg, 0.34 mmol), and carbon tetrabromide (112 mg, 0.35 mmol). The solution was allowed to return at room temperature and was stirred for 90 min. The resulting solution was diluted with dichloromethane (25 mL), washed with a 10% sodium bicarbonate solution and filtered over a cotton plug. Purification of the resulting crude product by flash chromatography using ethyl acetate/hexane (7:3) as an eluant gave the desired compound 31a (22 mg, 60%). $^1$H NMR (400 MHz, Acetone-d$_6$) δ: 2.71 (t, 4H, J=5.12 Hz), 2.82 (m, 2H), 3.56 (m, 6H), 7.27 (dd, 1H, J$_1$=6.23 Hz, J$_2$=2.61 Hz), 7.35 (d, 1H, J=2.53 Hz), 7.78 (d, 1H, J=8.84 Hz).

General Procedure for the Synthesis of Compounds 32a:

To a solution of appropriate phenol (0.09 mmol) in dimethylformamide (1.5 mL) was added cesium carbonate (0.150 mmol). The solution was heated at 70° C. under argon and stirred for 30 min, before the addition of compound 31a (22 mg, 0.06 mmol). The resulting solution was stirred for an additional 4 hrs. The solution was then poured in water (30 mL), extracted with diethyl ether (3×15 mL), washed with a brine solution, and finally dried with magnesium sulphate. Purification of the resulting crude product by flash chromatography using dichloromethane/acetone (95:5) as an eluant gave the desired compound 32a in moderate yield (25%).

4-{4-[2-(3,5-Difluoro-phenoxy)-ethyl]-piperazin-1-yl}-2-(trifluoromethyl)-benzonitrile (EM-7263): $^1$H NMR (400 MHz, Acetone-d$_6$) δ: 2.76 (t, 4H, J=5.16 Hz), 2.89 (t, 2H, J=5.38 Hz), 3.50 (t, 4H, J=5.17 Hz), 4.19 (t, 2H, J=5.37 Hz), 6.57 (m, 3H), 7.20 (dd, 1H, J$_1$=6.28 Hz, J$_2$=2.58 Hz), 7.30 (d, 1H, J=2.44 Hz), 7.73 (d, 1H, J=8.83 Hz).

4-{4-[2-(2-methyl-4-(morpholinomethyl)-phenoxy)-ethyl]-piperazin-1-yl}-2-(trifluoromethyl)-benzonitrile (EM-7547): $^1$H NMR (400 MHz, Acetone-d$_6$) δ: 2.19 (s, 3H), 2.35 (broad s, 4H), 2.77 (t, 4H, J=5.12 Hz), 2.88 (t, 2H, J=5.59 Hz), 3.37 (s, 2H), 3.54 (t, 4H, J=5.12 Hz), 3.59 (t, 4H, J=4.62 Hz), 4.17 (t, 2H, J=5.59 Hz), 6.87 (d, 1H, J=7.96 Hz), 7.09 (m, 2H), 7.26 (dd, 1H, J$_1$=6.26 Hz, J$_2$=2.60 Hz), 7.35 (d, 1H, J=2.49 Hz), 7.76 (d, 1H, J=8.84 Hz).

Note: The piperazine derivatives of type 32b could be obtained by the same synthetic pathway, as were used for compounds 32a.

PHARMACEUTICAL COMPOSITION EXAMPLES

Set forth below, by way of example and not of limitation, are several pharmaceutical compositions utilizing a preferred active compound EM-7148 for systemic use. Other compounds of the invention or combination thereof, may be used in place of (or in addition to) EM-7148. The concentration of active ingredient may be varied over a wide range as discussed herein. The amounts and types of other ingredients that may be included are well known in the art.

Example A

Composition suitable for injection

| Ingredient | Weight % (by weight of total composition) |
|---|---|
| EM-7148 | 5.0 |
| Ethanol | 6.4 |
| NaCl | 0.8 |
| Water | 86.9 |
| Benzyl alcohol | 0.9 |

Example B

Tablet

| Ingredient | Weight % (by weight of total composition) |
|---|---|
| EM-7148 | 20.0 |
| Gelatin | 5.0 |
| Lactose | 47.5 |
| Starch | 27.5 |

Example C

Gelatin capsule

| Ingredient | Weight % (by weight of total composition) |
|---|---|
| EM-7148 | 20.0 |
| Lactose hydrous | 62.0 |
| Starch | 4.8 |
| Cellulose microcystalline | 12.8 |
| Magnesium stearate | 0.4 |

Other antiandrogens (i.e. EM-7105, EM-7203 or EM-7363) may be substituted for EM-7148 in the above formulations. For combination therapies, 5alpha reductase inhibitors, 17beta-hydroxysteroid dehydrogenase type 5 inhibitors and 17b-hydroxysteroid dehydrogenase inhibitors type 13 could be added at weight % (with prorata reduction of other components).

Example D

Composition suitable for injection

| Ingredient | Weight % (by weight of total composition) |
|---|---|
| EM-7148 | 5.0 |
| Finasteride | 0.4 |
| Ethanol | 6.0 |
| NaCl | 0.8 |
| Water | 86.9 |
| Benzyl alcohol | 0.9 |

Example E

Tablet

| Ingredient | Weight % (by weight of total composition) |
|---|---|
| EM-7148 | 20.0 |
| Finasteride | 1.0 |
| Gelatin | 5.0 |
| Lactose | 46.5 |
| Starch | 27.5 |

Example F

Gelatin capsule

| Ingredient | Weight % (by weight of total composition) |
|---|---|
| EM-7148 | 20.0 |
| Finasteride | 1.0 |
| Lactose hydrous | 61.0 |
| Starch | 4.8 |
| Cellulose microcystalline | 12.8 |
| Magnesium stearate | 0.4 |

Example G

Composition suitable for injection

| Ingredient | Weight % (by weight of total composition) |
|---|---|
| EM-7148 | 5.0 |
| EM-1404 | 5.0 |
| Ethanol | 6.0 |
| NaCl | 0.8 |
| Water | 82.3 |
| Benzyl alcohol | 0.9 |

Example H

Tablet

| Ingredient | Weight % (by weight of total composition) |
|---|---|
| EM-7148 | 20.0 |
| EM-1404 | 20.0 |
| Gelatin | 5.0 |
| Lactose | 27.5 |
| Starch | 27.5 |

Example I

Gelatin capsule

| Ingredient | Weight % (by weight of total composition) |
|---|---|
| EM-7148 | 20.0 |
| EM-1404 | 20.0 |
| Lactose hydrous | 42.0 |
| Starch | 4.8 |
| Cellulose microcystalline | 12.8 |
| Magnesium stearate | 0.4 |

Example J

| Composition suitable for injection | |
|---|---|
| Ingredient | Weight % (by weight of total composition) |
| EM-7148 | 5.0 |
| EM-1791 | 0.4 |
| Ethanol | 6.0 |
| NaCl | 0.8 |
| Water | 86.9 |
| Benzyl alcohol | 0.9 |

Example K

| Tablet | |
|---|---|
| Ingredient | Weight % (by weight of total composition) |
| EM-7148 | 20.0 |
| EM-1791 | 20.0 |
| Starch | 27.5 |
| Gelatin | 5.0 |
| Lactose | 27.5 |

Example L

| Gelatin capsule | |
|---|---|
| Ingredient | Weight % (by weight of total composition) |
| EM-7148 | 20.0 |
| EM-1791 | 20.0 |
| Lactose hydrous | 42.0 |
| Cellulose microcrystalline | 12.8 |
| Magnesium stearate | 0.4 |
| Starch | 4.8 |

The invention has been described in terms of preferred embodiments and examples, but is not limited thereby. Those of skill in the art will readily recognize the broader applicability and scope of the invention which is limited only by the patent claims that issue from this application or any patent application claiming priority (directly or indirectly) hereto.

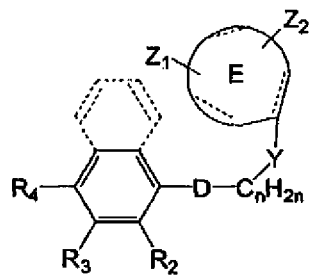

What is claimed is:

1. A method of treating prostate cancer, comprising administering to a patient in need of such treatment a therapeutically effective amount of a compound of the formula

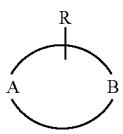

wherein the compound

has the following structure:

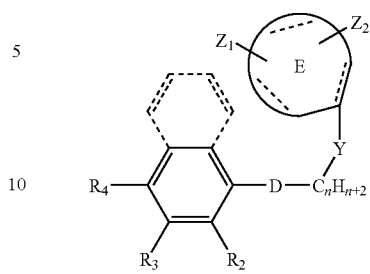

wherein n is an integer selected from 0 to 3;
wherein dotted lines represent optional bonds;
wherein $R_2$ is selected from the group consisting of hydrogen and lower ($C_1$-$C_3$) alkyl;
wherein $R_3$ and $R_4$ are independently selected from the group consisting of hydrogen, halogen, nitrile, —$COCH_3$, —$SO_2CH_3$, $NO_2$, $OCH_3$, $SCH_3$, alkylsulfoxide, alkylsulfone, alkyl, methyl, and halogenated methyl; wherein at least one of $R_3$ and $R_4$ is not hydrogen;
wherein D is selected from the group consisting of

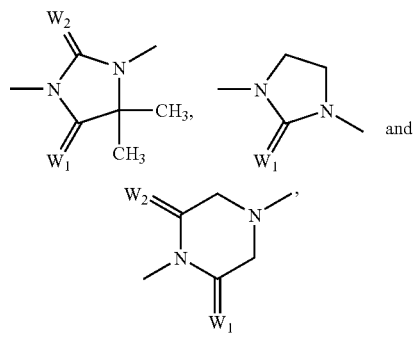

wherein $W_1$ and $W_2$ are independently selected from the group consisting of —$CH_2$—, oxygen and sulphur;
wherein Y is selected from the group consisting of -$MCH_2CH_2$—, —$CH_2MCH_2$—, and —$CH_2CH_2M$-;
wherein M is selected from the group consisting of —O—, —S—, —$SO_2$—, and —$CH_2$—;
wherein E is selected from the group consisting of phenylene and mono-substituted pyridyl;
wherein $Z_1$ is a hydrocarbon moiety additionally having at least one carbonyl, sulfone or sulfoxide group or nitrogen atom separated from E by none to four intervening atoms, and said nitrogen atom being an amine, an amide, an N-oxide, or a quaternary ammonium salt, $Z_1$ optionally, having other oxygen, sulphur, or nitrogen atoms; and
wherein $Z_2$ is selected from the group consisting of hydrogen, fluorine, chlorine, bromine, iodine, cyano, nitro, trifluoromethyl, alkoxy, $C_1$-$C_5$ straight or branched alkyl, $C_2$-$C_5$ straight or branched alkenyl, and $C_2$-$C_5$ straight or branched alkynyl; or
a pharmaceutically acceptable salt thereof.

2. A method of treating prostate cancer according to claim 1 comprising administering to a patient in need of such treatment a therapeutically effective amount of a compound selected from the group consisting of a) a compound of the formula

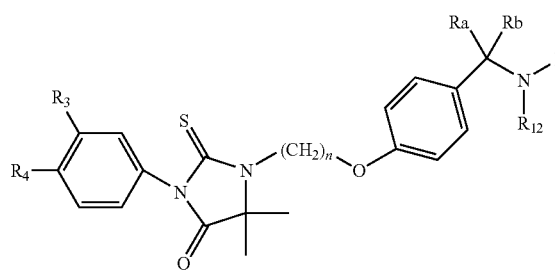

wherein n is an integer from 1 to 3;
wherein Ra and Rb are independently selected from the group consisting of hydrogen, $C_1$-$C_6$ alkyl and $C_2$-$C_6$ alkenyl; wherein Ra and Rb together may form a ring;
wherein $R_3$ is selected from the group consisting of hydrogen, halogen, $OCH_3$, $SCH_3$, alkylsulfoxide, alkylsulfone, nitrile, $NO_2$, alkyl, methyl, and trifluoromethyl;
wherein $R_4$ is selected from the group consisting of halogen, nitrile, —$COCH_3$, —$SO_2CH_3$, and —$NO_2$;
wherein $R_{11}$ and $R_{12}$ are independently selected from the group consisting of hydrogen and $C_1$-$C_6$ lower alkyl or $R_{11}$ and $R_{12}$ together form a heterocycle optionally having another heteroatom selected from the group consisting of nitrogen, oxygen, selenium, silicium and sulphur or a pharmaceutically acceptable salt thereof; and
b) a compound of the formula

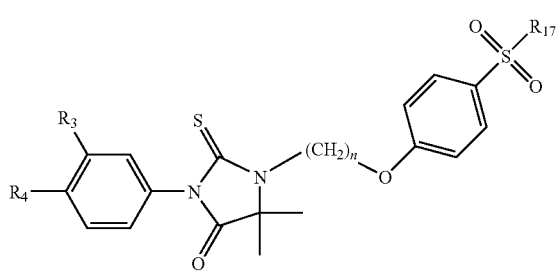

wherein n is an integer from 1 to 3;
$R_3$ is selected from the group consisting of hydrogen, halogen, $OCH_3$, $SCH_3$, alkylsulfoxide, alkylsulfone, nitrile, $NO_2$, alkyl, methyl, and trifluoromethyl;
$R_4$ is selected from the group consisting of halogen, nitrile, —$COCH_3$, —$SO_2CH_3$, and —$NO_2$; and
$R_{17}$ is $C_1$-$C_6$ lower alkyl.

3. A method of treating prostate cancer according to claim 1 comprising administering to a patient in need of such treatment a therapeutically effective amount of a compound selected from the group consisting of:

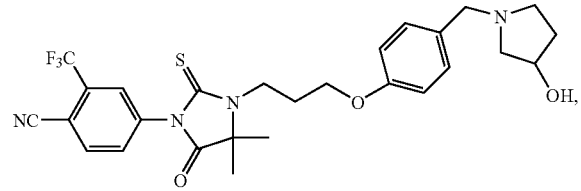

-continued

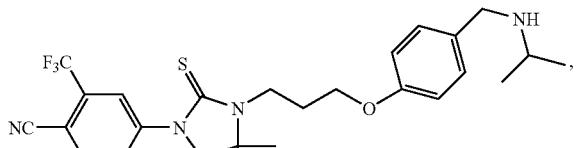

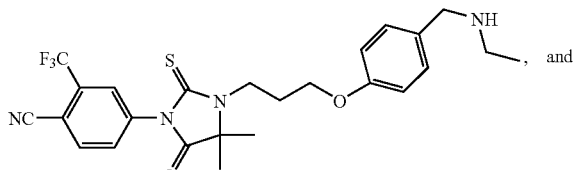

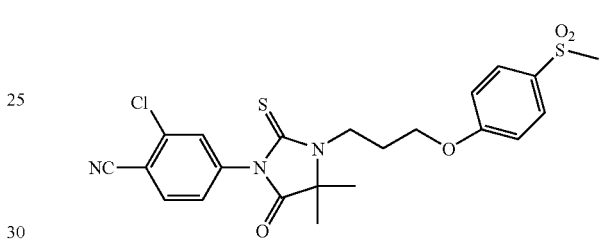

or a pharmaceutically acceptable salt thereof.

4. The method of claim 1, further comprising administering to said patient a therapeutically effective amount of at least one inhibitor selected from the group consisting of an inhibitor of type 13 17β-hydroxysteroid dehydrogenase, an inhibitor of type 5 17β-hydroxysteroid dehydrogenase, an inhibitor of 5α-reductase and an inhibitor of androgen-synthesizing enzymes.

5. The method of claim 4, wherein an inhibitor of 5α-reductase and an inhibitor of type 13 17β-hydroxysteroid dehydrogenase are administered.

6. The method of claim 1, further comprising orchiectomy or administering an LHRH agonist or antagonist.

7. A method of treating benign prostatic hyperplasia comprising administering to a patient in need of such treatment a therapeutically effective amount of a compound of the formula

wherein the compound

has the following structure:

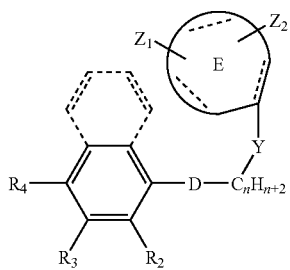

wherein n is an integer selected from 0 to 3;
wherein dotted lines represent optional bonds;
wherein $R_2$ is selected from the group consisting of hydrogen and lower ($C_1$-$C_3$) alkyl;
wherein $R_3$ and $R_4$ are independently selected from the group consisting of hydrogen, halogen, nitrile, —COCH$_3$, —SO$_2$CH$_3$, NO$_2$, OCH$_3$, SCH$_3$, alkylsulfoxide, alkylsulfone, alkyl, methyl, and halogenated methyl; wherein at least one of $R_3$ and $R_4$ is not hydrogen;
wherein D is selected from the group consisting of

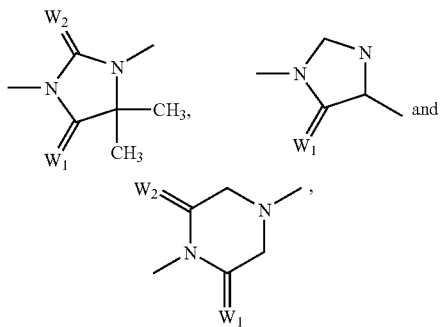

wherein $W_1$ and $W_2$ are independently selected from the group consisting of —CH$_2$—, oxygen and sulphur;
wherein Y is selected from the group consisting of -MCH$_2$CH$_2$—, —CH$_2$MCH$_2$—, and —CH$_2$CH$_2$M-;
wherein M is selected from the group consisting of —O—, —S—, —SO$_2$—, and —CH$_2$—;
wherein E is selected from the group consisting of phenylene and mono-substituted pyridyl;
wherein $Z_1$ is a hydrocarbon moiety additionally having at least one carbonyl, sulfone or sulfoxide group or nitrogen atom separated from E by none to four intervening atoms, and said nitrogen atom being an amine, an amide, an N-oxide, or a quaternary ammonium salt, $Z_1$, optionally, having other oxygen, sulphur, or nitrogen atoms; and
wherein $Z_2$ is selected from the group consisting of hydrogen, fluorine, chlorine, bromine, iodine, cyano, nitro, trifluoromethyl, alkoxy, $C_1$-$C_5$ straight or branched alkyl, $C_2$-$C_5$ straight or branched alkenyl, and $C_2$-$C_5$ straight or branched alkynyl; or
a pharmaceutically acceptable salt thereof.

8. The method of claim 7, further comprising administering to said patient a therapeutically effective amount of at least one inhibitor selected from the group consisting of an antiestrogen, an inhibitor of aromatase, an inhibitor of type 13 17β-hydroxysteroid dehydrogenase, and an inhibitor of 5α-reductase.

9. The method of claim 8, wherein an inhibitor of 5α-reductase and an inhibitor of type 13 17β-hydroxysteroid dehydrogenase are administered 10. The method of claim 4 further comprising orchiectomy or administering an LHRH agonist or antagonist.

11. The method of claim 5 further comprising orchiectomy or administering an LHRH agonist or antagonist.

12. A method according to any one of claims 1 and 7 wherein E is phenylene.

13. A method according to any one of claims 1 and 7 wherein Y is —CH$_2$CH$_2$O—.

14. A method according to claim 12 wherein Y is —CH$_2$CH$_2$O—.

15. A method according to any one of claims 1 and 7 wherein $Z_1$ is located in the para position with respect to the group Y and the nitrogen or sulfur atom of $Z_1$ is separated from the phenylene or mono-substituted pyridyl ring by none to four intervening atoms, wherein $Z_1$ is selected from the group consisting of

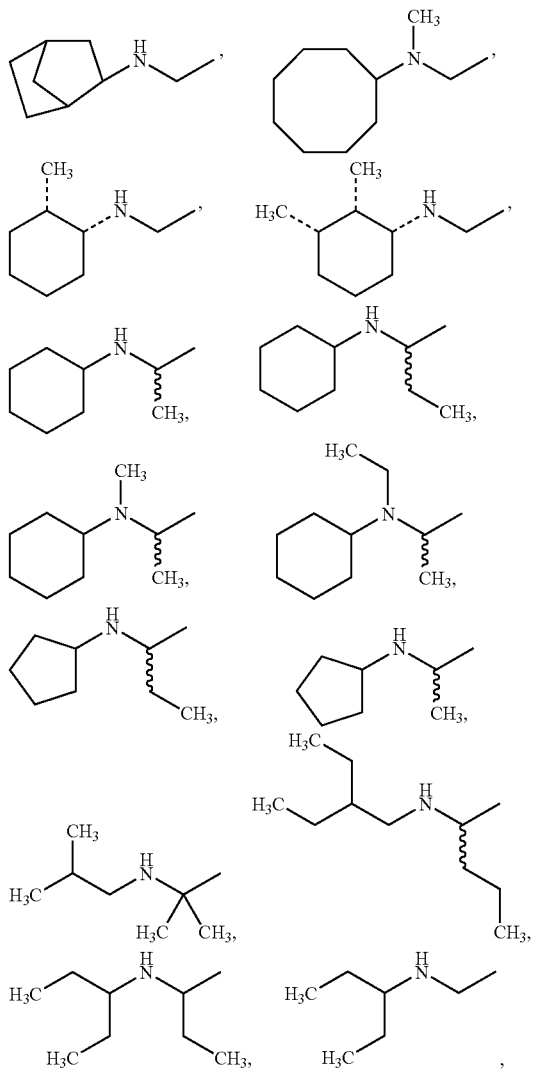

-continued

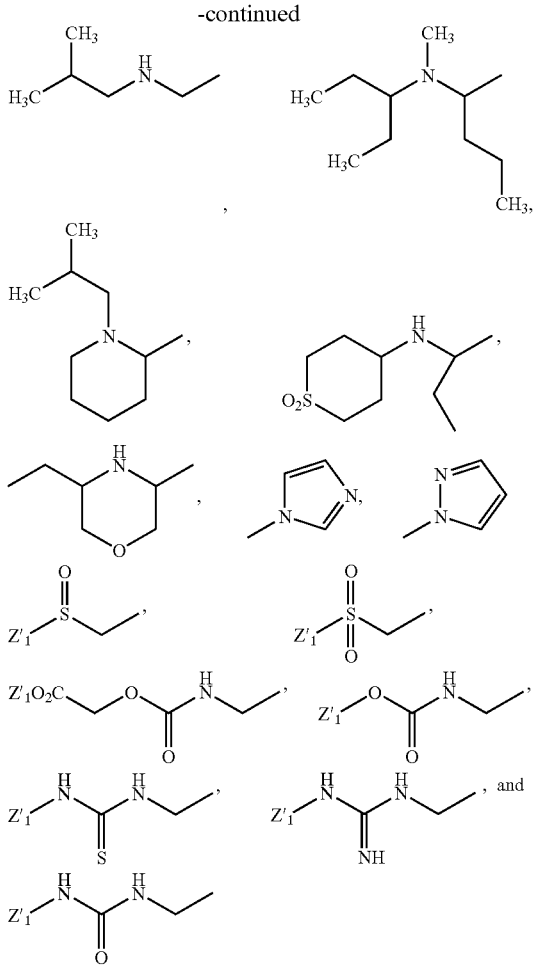

wherein Z'$_1$ is hydrogen, lower C$_1$-C$_6$ alkyl, alkylene or aryl, or Z'$_1$ fusioned with the group E forms a bicyclic moiety selected from the group consisting of:

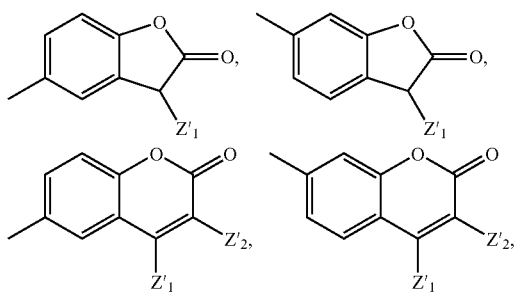

wherein Z'$_1$ and Z'$_2$ are independently hydrogen, lower C$_1$-C$_6$ alkyl, alkylene or aryl.

16. A method according to claim 15 wherein E is phenylene.

17. A method according to claim 15 wherein Y is —CH$_2$CH$_2$O—.

18. The method of claim 2, further comprising administering to said patient a therapeutically effective amount of at least one inhibitor selected from the group consisting of an inhibitor of type 13 17β-hydroxysteroid dehydrogenase, an inhibitor of type 5 17β-hydroxysteroid dehydrogenase, an inhibitor of 5α-reductase and an inhibitor of androgen-synthesizing enzymes.

19. The method of claim 18, wherein an inhibitor of 5α-reductase and an inhibitor of type 13 17β-hydroxysteroid dehydrogenase are administered.

20. The method of claim 2, further comprising orchiectomy or administering an LHRH agonist or antagonist.

21. The method of claim 3, further comprising administering to said patient a therapeutically effective amount of at least one inhibitor selected from the group consisting of an inhibitor of type 13 17β-hydroxysteroid dehydrogenase, an inhibitor of type 5 17β-hydroxysteroid dehydrogenase, an inhibitor of 5α-reductase and an inhibitor of androgen-synthesizing enzymes.

22. The method of claim 21, wherein an inhibitor of 5α-reductase and an inhibitor of type 13 17β-hydroxysteroid dehydrogenase are administered.

23. The method of claim 3, further comprising orchiectomy or administering an LHRH agonist or antagonist.

24. A method of treating benign prostatic hyperplasia according to claim 7 comprising administering to a patient in need of such a therapeutically effective amount of a compound selected from the group consisting of
a) a compound of the formula

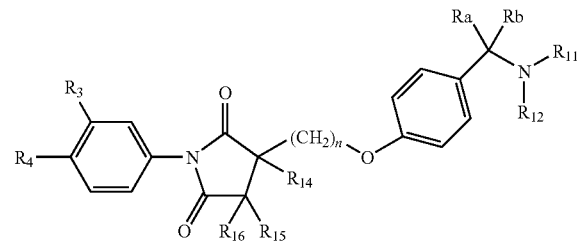

wherein n is an integer from 1 to 3;
wherein Ra and Rb are independently selected from the group consisting of hydrogen, C$_1$-C$_6$ alkyl and C$_2$-C$_6$ alkenyl; wherein Ra and Rb together may form a ring;
wherein R$_3$ is selected from the group consisting of hydrogen, halogen, OCH$_3$, SCH$_3$ alkylsulfoxide, alkylsulfone, nitrile, NO$_2$, alkyl, methyl, and trifluoromethyl;
wherein R$_4$ is selected from the group consisting of halogen, nitrile, —COCH$_3$, —SO$_2$CH$_3$, and —NO$_2$;
wherein R$_{11}$ and R$_{12}$ are independently selected from the group consisting of hydrogen and C$_1$-C$_6$ lower alkyl or R$_{11}$ and R$_{12}$ together form a heterocycle optionally having another heteroatom selected from the group consisting of nitrogen, oxygen, selenium, silicium and sulphur or a pharmaceutically acceptable salt thereof; and
b) a compound of the formula

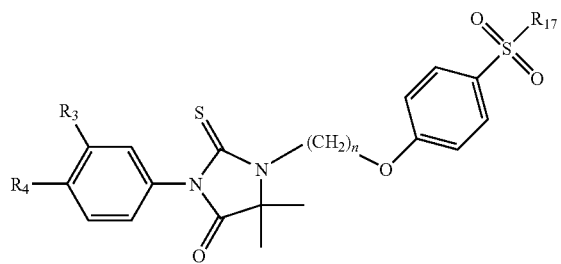

wherein n is an integer from 1 to 3;
R$_3$ is selected from the group consisting of hydrogen, halogen, OCH$_3$, SCH$_3$, alkylsulfoxide, alkylsulfone, nitrile, NO$_2$, alkyl, methyl, and trifluoromethyl;
R$_4$ is selected from the group consisting of halogen, nitrile, —COCH$_3$, —SO$_2$CH$_3$, and —NO$_2$; and
R$_{17}$ is C$_1$-C$_6$ lower alkyl.

25. The method of claim 24, further comprising administering to said patient a therapeutically effective amount of at least one inhibitor selected from the group consisting of an antiestrogen, an inhibitor of aromatase, an inhibitor of type 13 17β-hydroxysteroid dehydrogenase, and an inhibitor of 5α-reductase.

26. The method of claim 25, wherein an inhibitor of 5α-reductase and an inhibitor of type 13 17β-hydroxysteroid dehydrogenase are administered.

27. A method of treating benign prostatic hyperplasia according to claim 7 comprising administering to a patient in need of such treatment a therapeutically effective amount of a compound selected from the group consisting of:

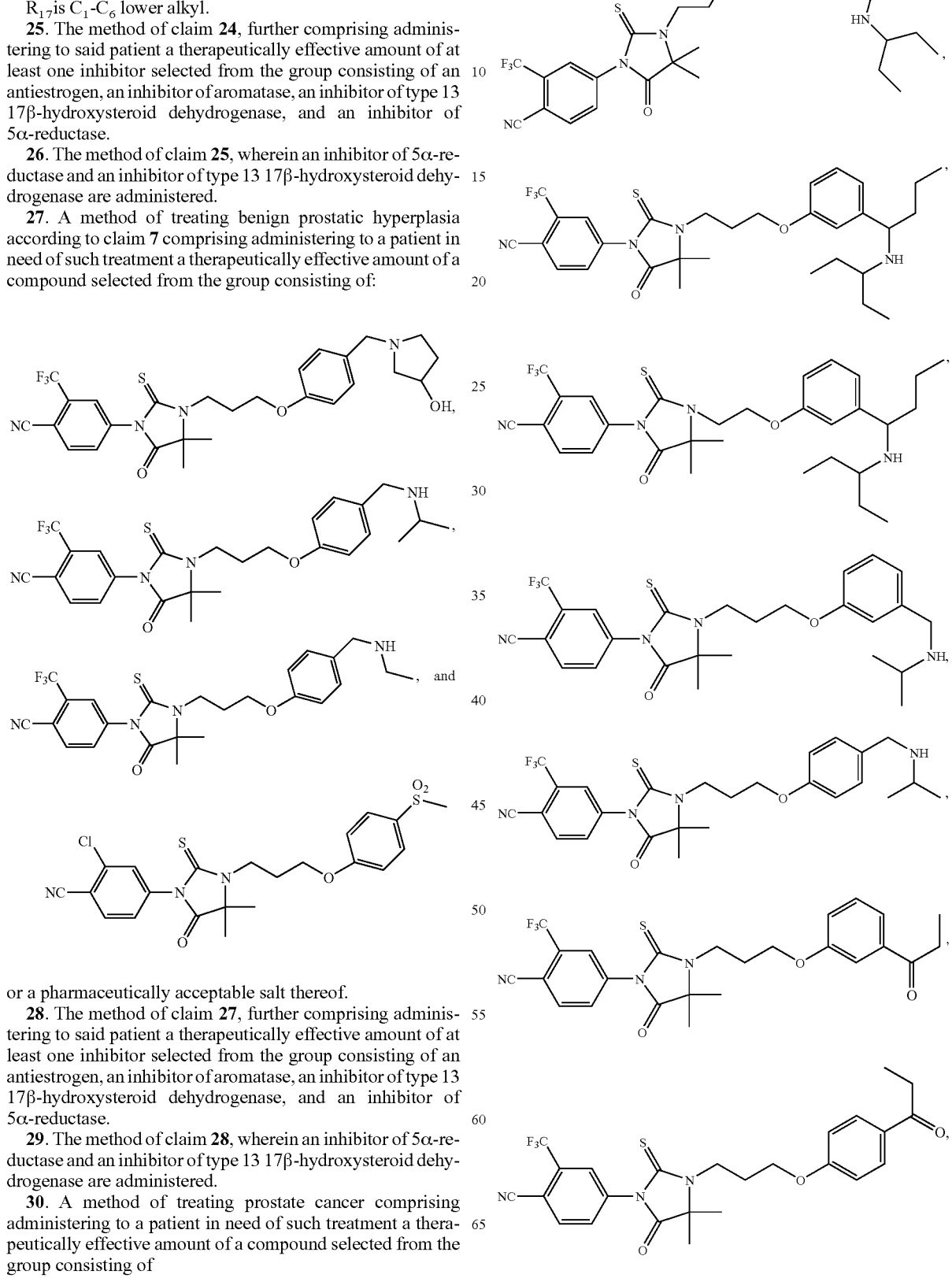

or a pharmaceutically acceptable salt thereof.

28. The method of claim 27, further comprising administering to said patient a therapeutically effective amount of at least one inhibitor selected from the group consisting of an antiestrogen, an inhibitor of aromatase, an inhibitor of type 13 17β-hydroxysteroid dehydrogenase, and an inhibitor of 5α-reductase.

29. The method of claim 28, wherein an inhibitor of 5α-reductase and an inhibitor of type 13 17β-hydroxysteroid dehydrogenase are administered.

30. A method of treating prostate cancer comprising administering to a patient in need of such treatment a therapeutically effective amount of a compound selected from the group consisting of 123
-continued
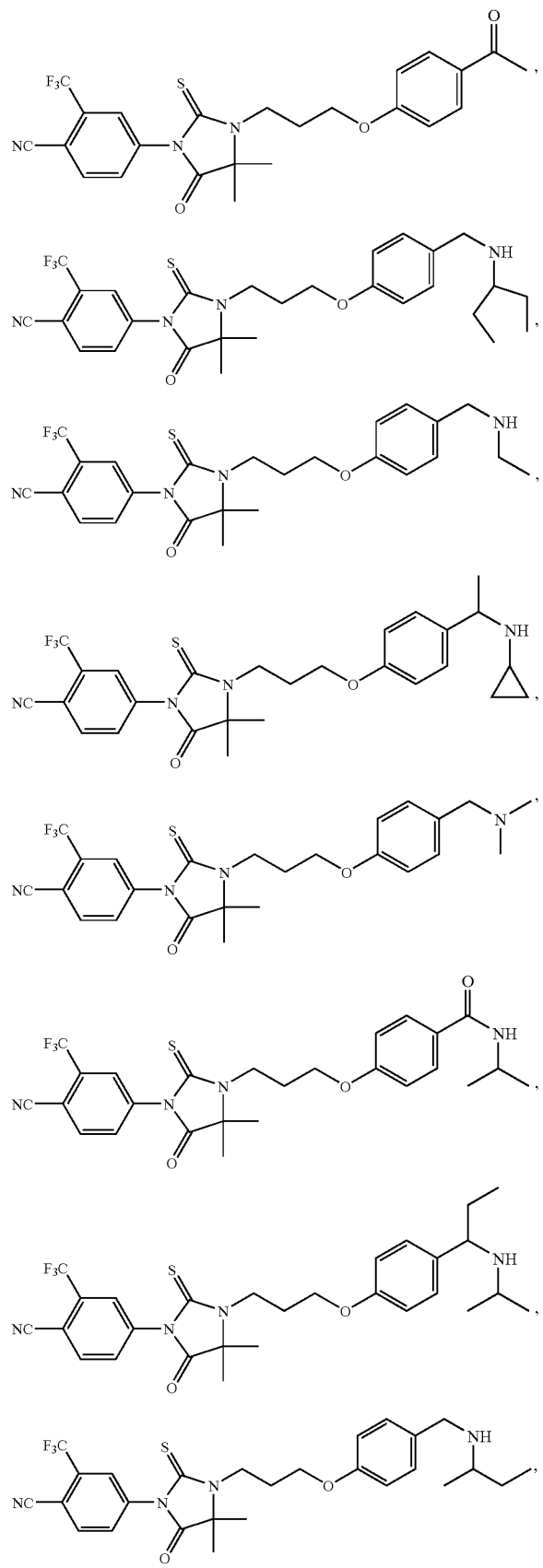
124
-continued
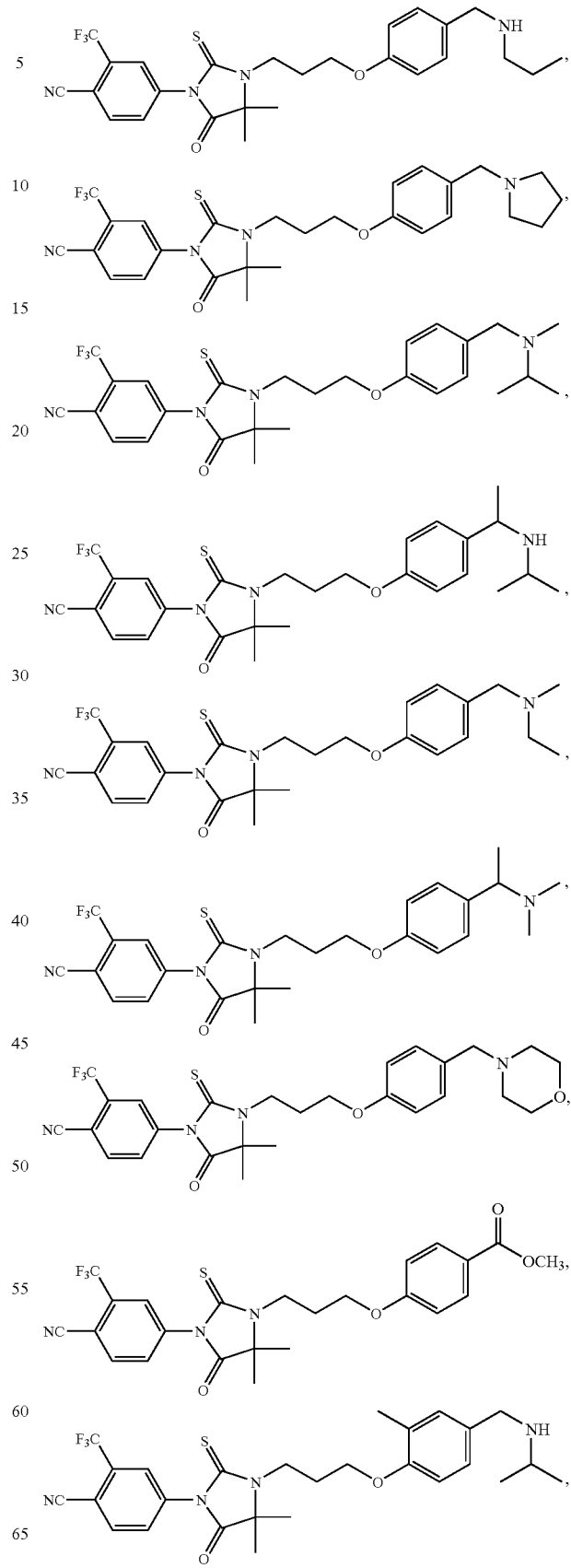

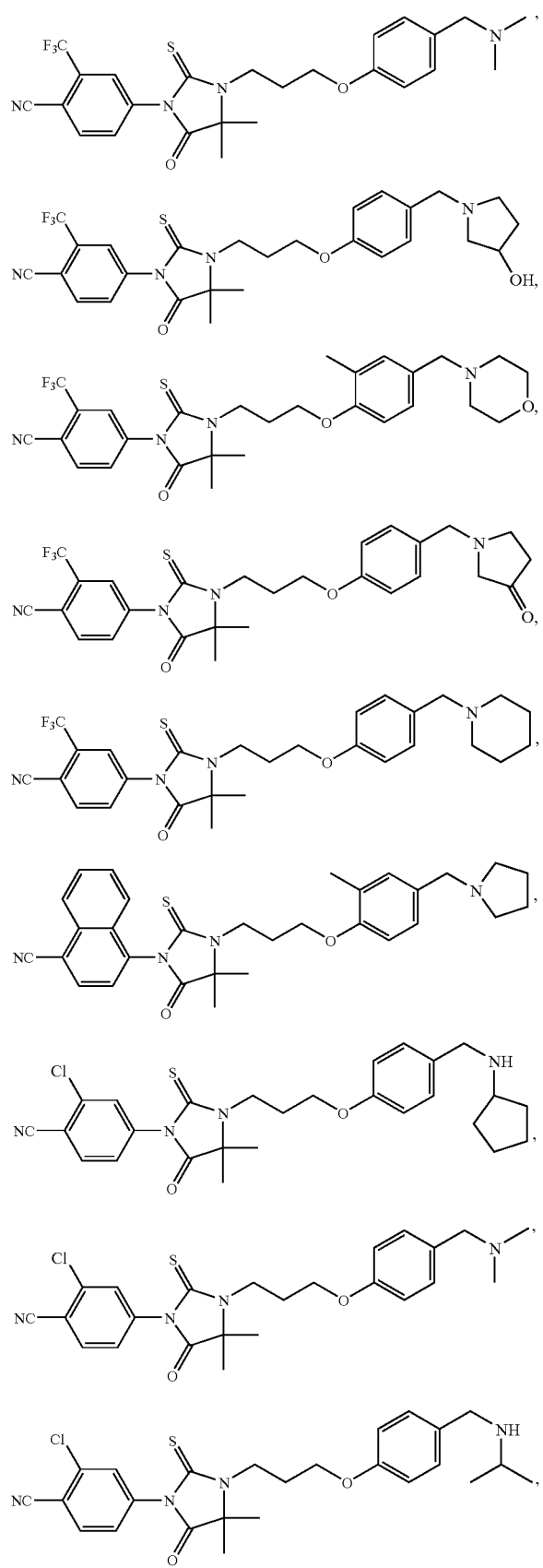
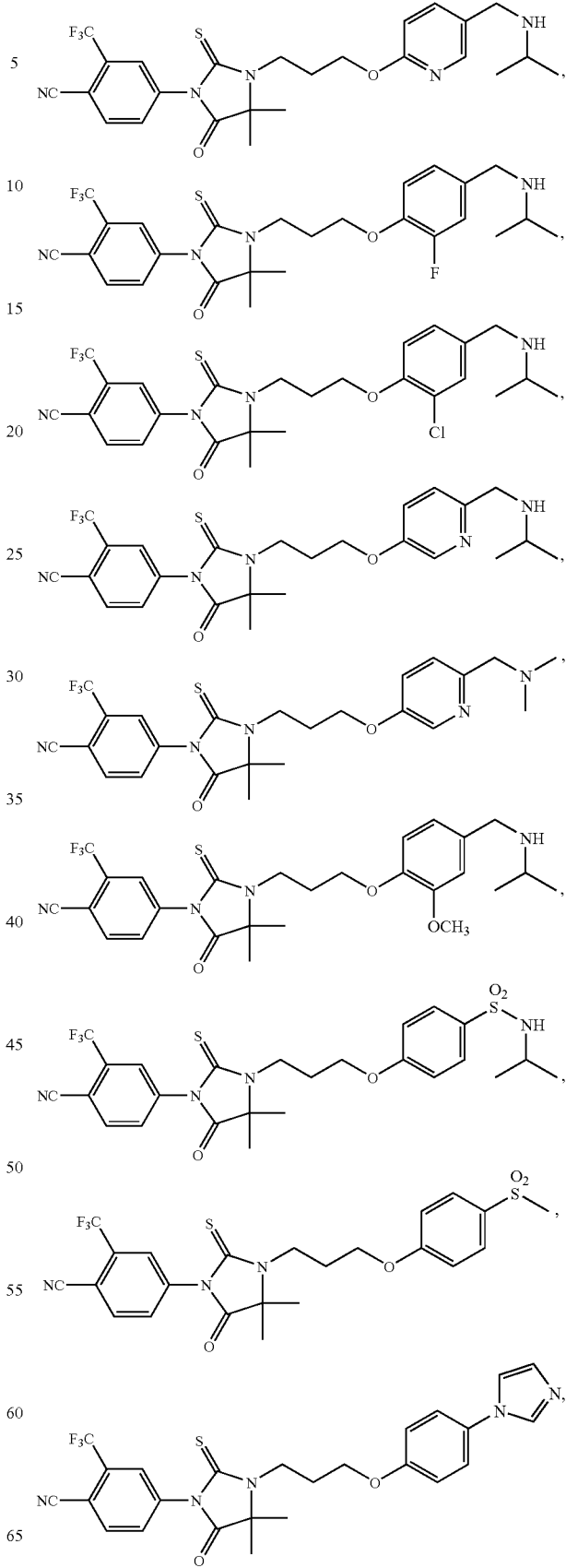

-continued

-continued
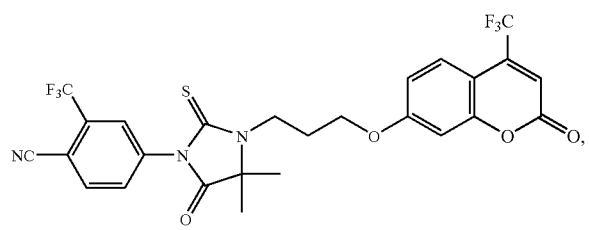
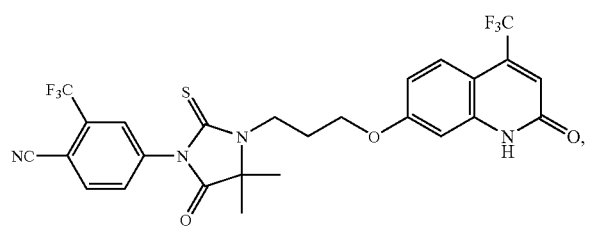
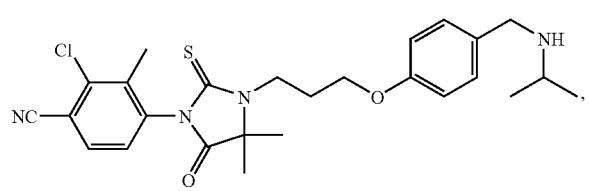
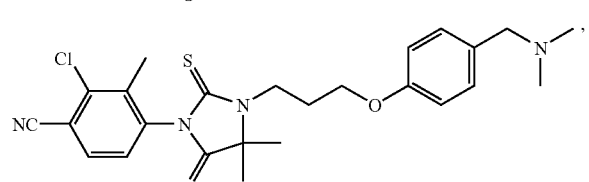
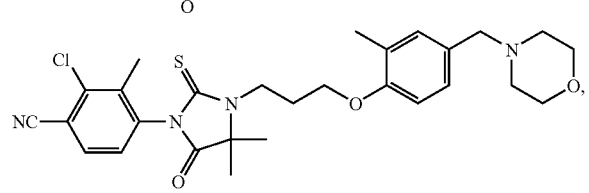
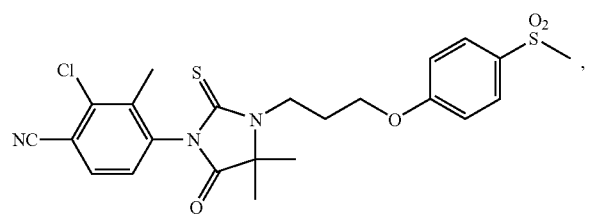
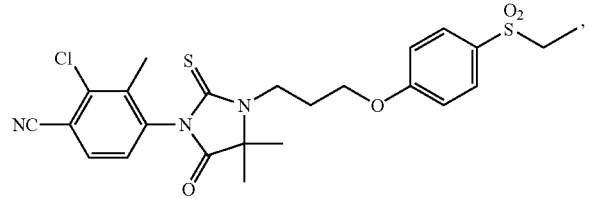
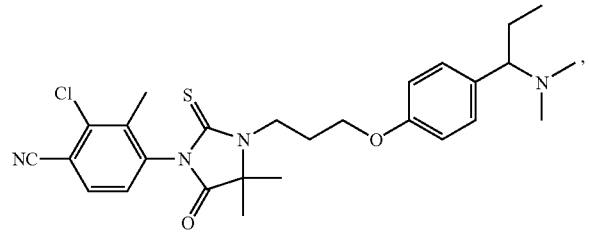
-continued
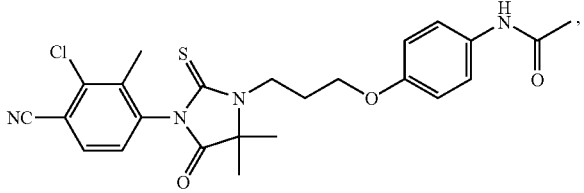
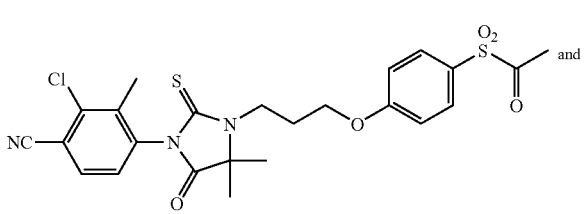
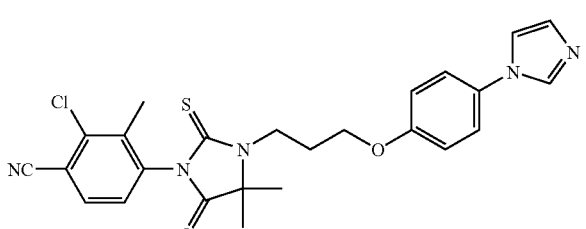
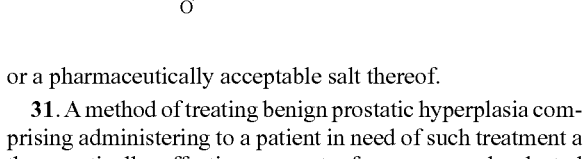
or a pharmaceutically acceptable salt thereof.
31. A method of treating benign prostatic hyperplasia comprising administering to a patient in need of such treatment a therapeutically effective amount of a compound selected from the group consisting of
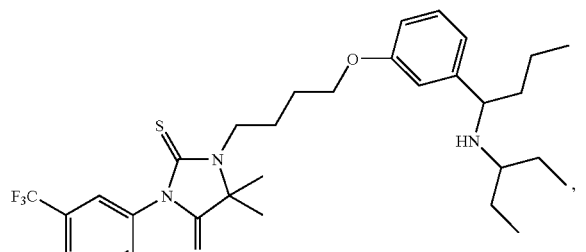
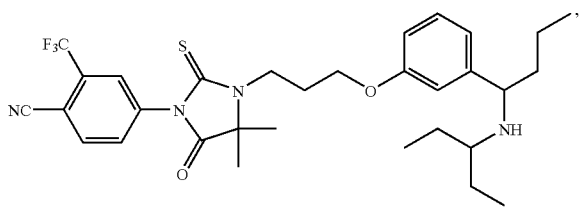
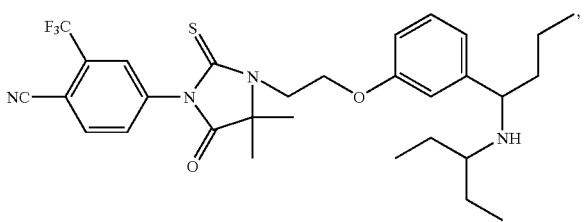

-continued

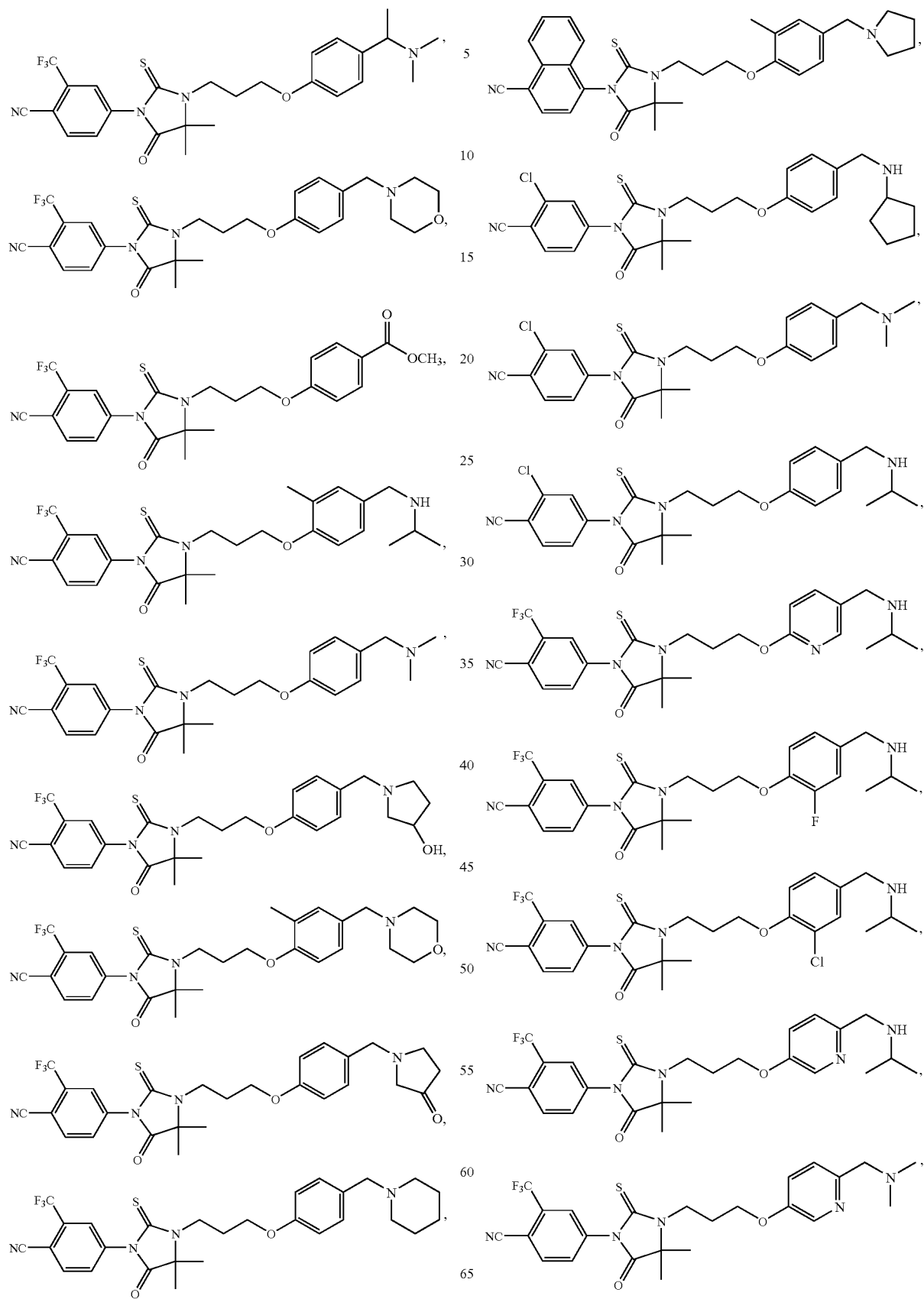

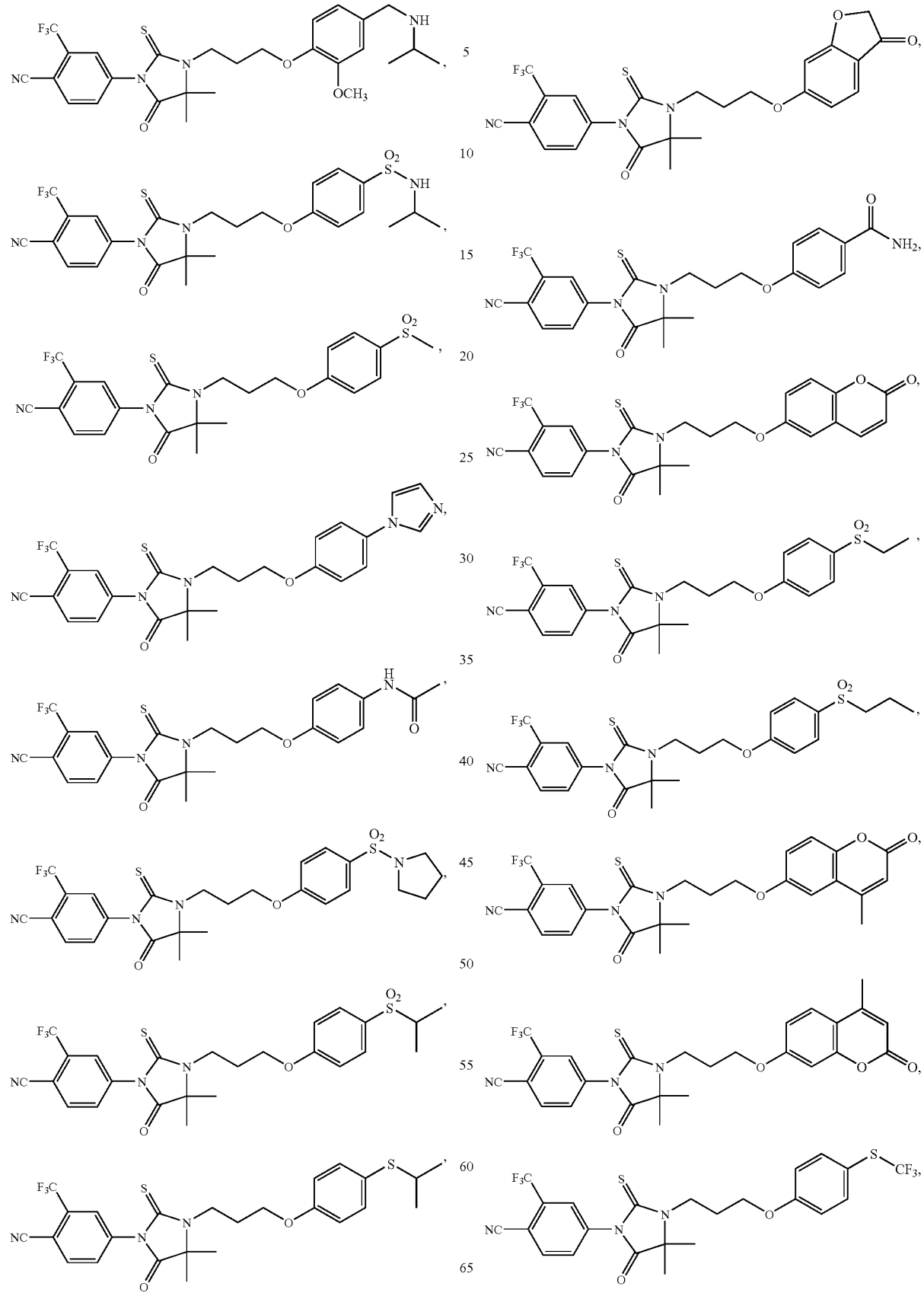

-continued

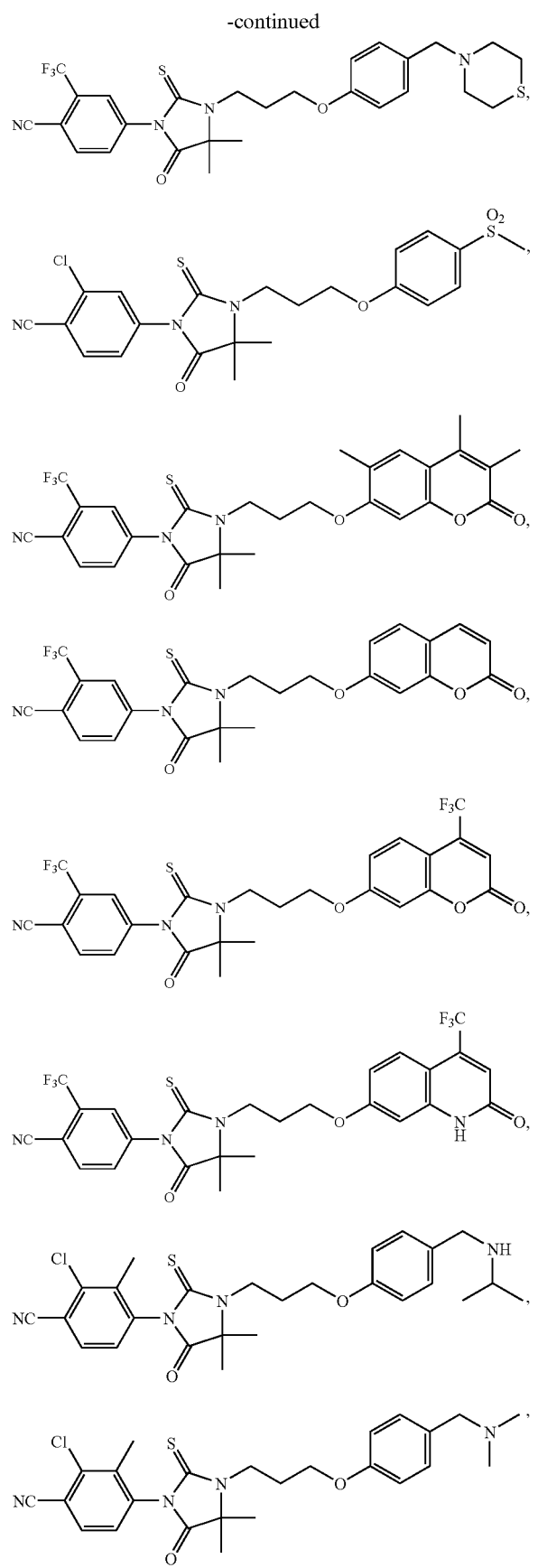

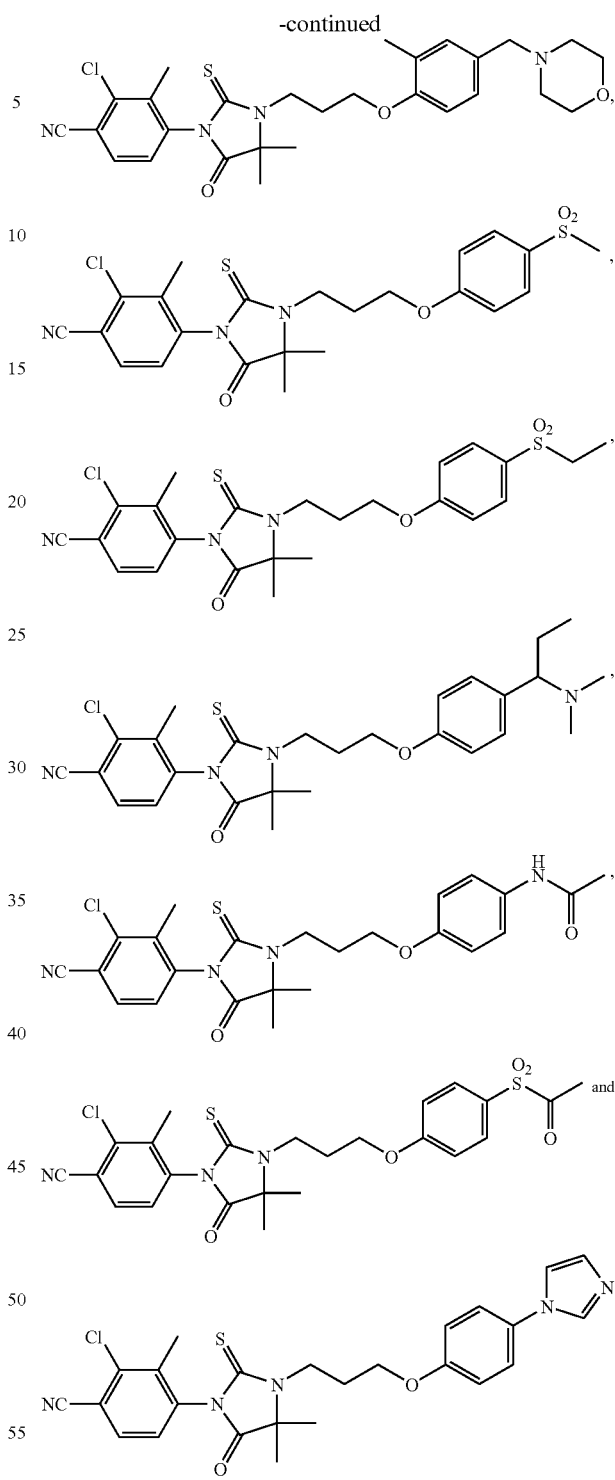

or a pharmaceutically acceptable salt thereof.

32. The method of claim 30, further comprising administering to said patient a therapeutically effective amount of at least one inhibitor selected from the group consisting of an inhibitor of type 13 17β-hydroxysteroid dehydrogenase, an inhibitor of type 5 17β-hydroxysteroid dehydrogenase, an inhibitor of 5α-reductase and an inhibitor of androgen-synthesizing enzymes.

33. The method of claim 32, wherein an inhibitor of 5α-reductase and an inhibitor of type 13 17β-hydroxysteroid dehydrogenase are administered.

34. The method of claim 30, further comprising orchiectomy or administering an LHRH agonist or antagonist.

35. The method of claim 31, further comprising administering to said patient a therapeutically effective amount of at least one inhibitor selected from the group consisting of an antiestrogen, an inhibitor of aromatase, an inhibitor of type 13 17β-hydroxysteroid dehydrogenase, and an inhibitor of 5α-reductase.

36. The method of claim 35, wherein an inhibitor of 5α-reductase and an inhibitor of type 13 17β-hydroxysteroid dehydrogenase are administered.

37. The method of claim 19, further comprising orchiectomy or administering an LHRH agonist or antagonist.

38. The method of claim 18, further comprising orchiectomy or administering an LHRH agonist or antagonist.

39. The method of claim 22, further comprising orchiectomy or administering an LHRH agonist or antagonist.

40. The method of claim 21, further comprising orchiectomy or administering an LHRH agonist or antagonist.

41. The method of claim 33, further comprising orchiectomy or administering an LHRH agonist or antagonist.

42. The method of claim 32, further comprising orchiectomy or administering an LHRH agonist or antagonist.

* * * * *

UNITED STATES PATENT AND TRADEMARK OFFICE
CERTIFICATE OF CORRECTION

| | | |
|---|---|---|
| PATENT NO. | : 7,709,516 B2 | Page 1 of 2 |
| APPLICATION NO. | : 11/452545 | |
| DATED | : May 4, 2010 | |
| INVENTOR(S) | : Fernand Labrie et al. | |

It is certified that error appears in the above-identified patent and that said Letters Patent is hereby corrected as shown below:

In the Abstract:
The structure in the Abstract should appear as follows:

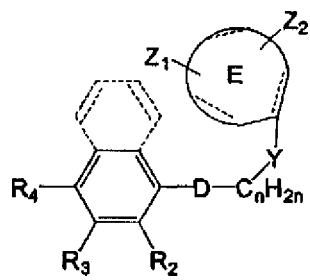

In the Specification:
Column 4, line 60, the structure should appear as follows:

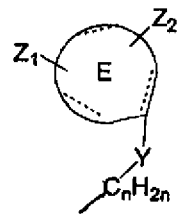

Column 5, line 25, the structure should appear as follows:

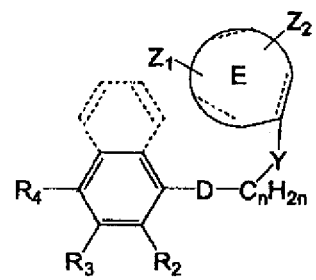

Signed and Sealed this
Eleventh Day of September, 2012

David J. Kappos
*Director of the United States Patent and Trademark Office*

CERTIFICATE OF CORRECTION (continued)
U.S. Pat. No. 7,709,516 B2

In the Claims:

Column 114, line 10, the structure that is a part of Claim 1 should appear as follows:

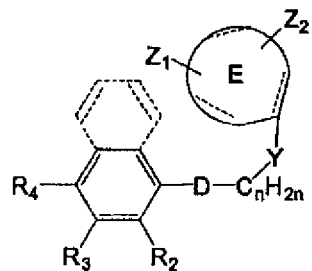

Column 117, line 10, the structure that is a part of Claim 7 should appear as follows: